US011116646B2

(12) United States Patent
Greenhalgh et al.

(10) Patent No.: US 11,116,646 B2
(45) Date of Patent: Sep. 14, 2021

(54) BONE GRAFT DELIVERY SYSTEM AND METHOD FOR USING SAME

(71) Applicant: SurGenTec, LLC, Boca Raton, FL (US)

(72) Inventors: Travis Greenhalgh, Boca Raton, FL (US); Ryan Lewis, Waxhaw, NC (US); Kraig Kooiman, Winters, CA (US); Andrew Shoup, Boca Raton, FL (US); Brad Caldeira, Margate, FL (US)

(73) Assignee: SurGenTec, LLC, Boca Raton, FL (US)

( * ) Notice: Subject to any disclaimer, the term of this patent is extended or adjusted under 35 U.S.C. 154(b) by 102 days.

(21) Appl. No.: 16/256,923

(22) Filed: Jan. 24, 2019

(65) Prior Publication Data

US 2019/0247201 A1   Aug. 15, 2019

Related U.S. Application Data

(63) Continuation of application No. 14/992,954, filed on Jan. 11, 2016, now Pat. No. 10,238,507.
(Continued)

(51) Int. Cl.
*A61F 2/46* (2006.01)
*A61F 2/44* (2006.01)
(Continued)

(52) U.S. Cl.
CPC ........ *A61F 2/4601* (2013.01); *A61B 17/1659* (2013.01); *A61B 17/1671* (2013.01);
(Continued)

(58) Field of Classification Search
CPC ............ A61B 17/8802; A61B 17/8805; A61B 17/8833; A61B 2017/8838; A61F 2/4601
See application file for complete search history.

(56) References Cited

U.S. PATENT DOCUMENTS

| 2,316,095 A | 4/1943 | Mead, Jr. |
| 4,277,184 A | 7/1981 | Solomon |
| (Continued) | | |

FOREIGN PATENT DOCUMENTS

| CA | 2656050 | 2/2015 |
| CN | 1654543 | 8/2005 |
| (Continued) | | |

OTHER PUBLICATIONS

Berkeley Advanced Biomaterials, Inc., 2014, Cem-Ostetic®, catalog, 3 pp.
(Continued)

*Primary Examiner* — Andrew Yang
(74) *Attorney, Agent, or Firm* — Knobbe Martens Olson & Bear, LLP

(57) ABSTRACT

A bone graft delivery system can include an elongate tube and a handle having a trigger and a ratcheting mechanism. The trigger is actuated to deliver bone graft material through the tube. The bone graft delivery system can further include a distal tip at a distal end of the tube. The tip has one or more openings to deliver the bone graft material to a desired location and includes a surface suitable to act as a rasp for decorticating bone. A method for delivering bone graft material to a desired surgical location includes providing a bone graft delivery device, positioning the device adjacent the surgical location, decorticating bone, and delivering bone graft material to the surgical location.

24 Claims, 76 Drawing Sheets

Related U.S. Application Data

(60) Provisional application No. 62/102,471, filed on Jan. 12, 2015.

(51) Int. Cl.
| | |
|---|---|
| *A61B 17/16* | (2006.01) |
| *A61F 2/28* | (2006.01) |
| *A61B 90/00* | (2016.01) |
| *A61B 17/00* | (2006.01) |
| *A61B 17/88* | (2006.01) |
| *A61F 2/30* | (2006.01) |

(52) U.S. Cl.
CPC ............ *A61F 2/447* (2013.01); *A61F 2/4455* (2013.01); *A61F 2/4611* (2013.01); *A61B 17/8825* (2013.01); *A61B 90/361* (2016.02); *A61B 2017/00407* (2013.01); *A61B 2017/00544* (2013.01); *A61B 2017/00734* (2013.01); *A61B 2090/3966* (2016.02); *A61F 2002/2835* (2013.01); *A61F 2002/30538* (2013.01); *A61F 2002/30556* (2013.01); *A61F 2002/30593* (2013.01); *A61F 2002/30784* (2013.01); *A61F 2002/30904* (2013.01); *A61F 2002/4629* (2013.01)

(56) References Cited

U.S. PATENT DOCUMENTS

| | | | |
|---|---|---|---|
| 4,338,925 A | 7/1982 | Miller | |
| 4,801,263 A * | 1/1989 | Clark | A61C 5/62 433/90 |
| 5,531,749 A | 7/1996 | Michelson | |
| 5,733,288 A | 3/1998 | Allen | |
| 5,861,176 A | 1/1999 | Ducheyne et al. | |
| 6,187,047 B1 | 2/2001 | Kwan et al. | |
| 6,224,607 B1 | 5/2001 | Michelson | |
| 6,331,312 B1 | 12/2001 | Lee et al. | |
| 6,439,439 B1 | 8/2002 | Rickard et al. | |
| 6,676,664 B1 * | 1/2004 | Al-Assir | A61B 17/8822 606/94 |
| 6,696,073 B2 | 2/2004 | Boyce et al. | |
| 6,767,550 B1 | 7/2004 | Génin et al. | |
| 6,793,660 B2 | 9/2004 | Kerr et al. | |
| 6,814,736 B2 | 11/2004 | Reiley et al. | |
| 7,141,054 B2 | 11/2006 | Vandewalle | |
| 7,150,879 B1 | 12/2006 | Lee et al. | |
| 7,214,635 B2 | 5/2007 | Gonda et al. | |
| 7,306,603 B2 | 12/2007 | Boehm, Jr. et al. | |
| 7,513,901 B2 | 4/2009 | Scifert et al. | |
| 7,517,539 B1 | 4/2009 | Lee et al. | |
| 7,718,616 B2 | 5/2010 | Thorne | |
| 7,799,033 B2 | 9/2010 | Assell et al. | |
| 7,811,291 B2 | 10/2010 | Liu et al. | |
| 7,887,543 B2 | 2/2011 | Sand et al. | |
| 7,909,833 B2 | 3/2011 | Voellmicke | |
| 7,964,206 B2 | 6/2011 | Suokas et al. | |
| 8,287,915 B2 | 10/2012 | Clineff et al. | |
| 8,303,967 B2 | 11/2012 | Clineff et al. | |
| 8,308,805 B2 | 11/2012 | Lynn et al. | |
| 8,460,686 B2 | 6/2013 | Clineff et al. | |
| 8,551,525 B2 | 10/2013 | Cook et al. | |
| 8,613,938 B2 | 12/2013 | Akella et al. | |
| 8,623,089 B2 | 1/2014 | Sharkey et al. | |
| 8,628,536 B2 | 1/2014 | Walker et al. | |
| 8,696,679 B2 * | 4/2014 | Shadduck | A61B 17/8836 606/94 |
| 8,778,378 B2 | 7/2014 | Clineff et al. | |
| 8,932,295 B1 | 1/2015 | Greenhalgh | |
| 8,945,137 B1 | 2/2015 | Greenhalgh et al. | |
| 9,005,286 B2 | 4/2015 | Giorno | |
| 9,119,646 B2 | 9/2015 | Sharkey et al. | |
| 9,138,187 B2 | 9/2015 | Sharkey et al. | |
| 9,173,694 B2 | 11/2015 | Kleiner | |
| 9,668,881 B1 | 6/2017 | Greenhalgh et al. | |
| 10,123,849 B2 | 11/2018 | Greenhalgh | |
| 10,238,507 B2 | 3/2019 | Greenhalgh et al. | |
| 10,292,747 B2 | 5/2019 | Greenhalgh et al. | |
| 10,405,905 B2 | 9/2019 | Greenhalgh | |
| 10,543,105 B2 | 1/2020 | Greenhalgh | |
| 2002/0155167 A1 | 10/2002 | Lee et al. | |
| 2003/0049328 A1 | 3/2003 | Dalal et al. | |
| 2003/0049329 A1 | 3/2003 | Lee et al. | |
| 2003/0055512 A1 | 3/2003 | Genin et al. | |
| 2003/0129748 A1 | 7/2003 | Flake et al. | |
| 2003/0158602 A1 | 8/2003 | Ting | |
| 2003/0216777 A1 | 11/2003 | Tien et al. | |
| 2004/0024409 A1 | 2/2004 | Sand et al. | |
| 2004/0071668 A1 | 4/2004 | Bays et al. | |
| 2004/0133211 A1 | 7/2004 | Raskin et al. | |
| 2004/0215201 A1 | 10/2004 | Lieberman | |
| 2005/0098915 A1 | 5/2005 | Long et al. | |
| 2005/0107800 A1 | 5/2005 | Frankel et al. | |
| 2005/0137604 A1 | 6/2005 | Assell et al. | |
| 2005/0142164 A1 | 6/2005 | Lindholm et al. | |
| 2005/0171549 A1 | 8/2005 | Boehm, Jr. et al. | |
| 2005/0203523 A1 | 9/2005 | Wenstrom, Jr. et al. | |
| 2006/0025861 A1 | 2/2006 | McKay | |
| 2006/0293687 A1 | 12/2006 | Bogert | |
| 2007/0005072 A1 | 1/2007 | Castillo et al. | |
| 2007/0016163 A1 | 1/2007 | Santini et al. | |
| 2007/0026030 A1 | 2/2007 | Gill et al. | |
| 2007/0026069 A1 | 2/2007 | Shastri et al. | |
| 2007/0040478 A1 | 2/2007 | Tofail et al. | |
| 2007/0043376 A1 | 2/2007 | Leatherbury et al. | |
| 2007/0190102 A1 | 8/2007 | Luo | |
| 2007/0224245 A1 | 9/2007 | Ameer et al. | |
| 2007/0276397 A1 | 11/2007 | Pacheco | |
| 2007/0289998 A1 | 12/2007 | Keller | |
| 2008/0033572 A1 | 2/2008 | D'Antonio et al. | |
| 2008/0065082 A1 | 3/2008 | Chang et al. | |
| 2008/0071284 A1 | 3/2008 | Lechmann | |
| 2008/0125856 A1 | 5/2008 | Perez-Cruet et al. | |
| 2008/0300684 A1 | 12/2008 | Shelokov | |
| 2009/0155332 A1 | 6/2009 | Sherry et al. | |
| 2009/0216238 A1 | 8/2009 | Stark | |
| 2009/0276056 A1 | 11/2009 | Bose et al. | |
| 2009/0317447 A1 | 12/2009 | Hsiao et al. | |
| 2009/0318925 A1 | 12/2009 | Campion et al. | |
| 2009/0318982 A1 | 12/2009 | Genin et al. | |
| 2009/0324683 A1 | 12/2009 | Evans et al. | |
| 2009/0325775 A1 | 12/2009 | Yeh | |
| 2010/0021518 A1 | 1/2010 | Scifert | |
| 2010/0036381 A1 | 2/2010 | Vanleeuwen | |
| 2010/0057087 A1 | 3/2010 | Cha | |
| 2010/0114317 A1 | 5/2010 | Lambrecht et al. | |
| 2010/0121459 A1 | 5/2010 | Garigapati et al. | |
| 2010/0174286 A1 | 7/2010 | Truckai et al. | |
| 2010/0178278 A1 | 7/2010 | Luo et al. | |
| 2010/0179556 A1 | 7/2010 | Scribner | |
| 2010/0204702 A1 | 8/2010 | Lechot et al. | |
| 2010/0222750 A1 | 9/2010 | Cheng | |
| 2010/0226959 A1 | 9/2010 | Mckay | |
| 2010/0262146 A1 | 10/2010 | Tulkis | |
| 2010/0297082 A1 | 11/2010 | Guelcher et al. | |
| 2011/0071527 A1 | 3/2011 | Nelson et al. | |
| 2011/0071536 A1 | 3/2011 | Kleiner et al. | |
| 2011/0117165 A1 | 5/2011 | Melican et al. | |
| 2011/0165199 A1 | 7/2011 | Thorne | |
| 2011/0196492 A1 | 8/2011 | Lambrecht et al. | |
| 2011/0218513 A1 | 9/2011 | Walker et al. | |
| 2011/0237704 A1 | 9/2011 | Guelcher et al. | |
| 2011/0243913 A1 | 10/2011 | Antonio | |
| 2011/0276147 A1 | 11/2011 | Cook et al. | |
| 2011/0280924 A1 | 11/2011 | Lin et al. | |
| 2012/0100225 A1 | 4/2012 | McKay | |
| 2012/0107383 A1 | 5/2012 | McKay | |
| 2012/0253316 A1 | 10/2012 | Oktavec et al. | |
| 2013/0090662 A1 | 4/2013 | Hanson et al. | |
| 2013/0122057 A1 | 5/2013 | Garigapati et al. | |
| 2013/0131683 A1 | 5/2013 | Shah et al. | |
| 2013/0236513 A1 | 9/2013 | Guelcher et al. | |
| 2013/0282128 A1 | 10/2013 | McKay | |

(56) References Cited

U.S. PATENT DOCUMENTS

| | | |
|---|---|---|
| 2014/0039454 A1 | 2/2014 | Sharkey |
| 2014/0079753 A1 | 3/2014 | Darby et al. |
| 2014/0121781 A1 | 5/2014 | Tunc et al. |
| 2014/0200676 A1 | 7/2014 | Shimko et al. |
| 2014/0248372 A1 | 9/2014 | Boden et al. |
| 2014/0251438 A1 | 9/2014 | Gettings et al. |
| 2014/0252044 A1 | 9/2014 | Greter et al. |
| 2014/0255334 A1 | 9/2014 | Raynor et al. |
| 2014/0271779 A1 | 9/2014 | Bagga et al. |
| 2014/0271785 A1 | 9/2014 | Bagga et al. |
| 2014/0271786 A1 | 9/2014 | Bagga et al. |
| 2014/0271914 A1 | 9/2014 | Wagner |
| 2014/0277569 A1 | 9/2014 | Lange |
| 2014/0358188 A1 | 12/2014 | Larson et al. |
| 2015/0054195 A1 | 2/2015 | Greyf |
| 2015/0071983 A1 | 3/2015 | Bagga et al. |
| 2015/0079146 A1 | 3/2015 | Pomrink et al. |
| 2015/0105748 A1 | 4/2015 | McBride et al. |
| 2015/0148292 A1 | 5/2015 | Boden et al. |
| 2015/0165092 A1 | 6/2015 | Kaplan et al. |
| 2015/0190148 A1 | 7/2015 | Greenhalgh |
| 2015/0209156 A1 | 7/2015 | Greenhalgh et al. |
| 2015/0283298 A1 | 10/2015 | Kaplan et al. |
| 2015/0283300 A1 | 10/2015 | Pomrink et al. |
| 2017/0354515 A1 | 12/2017 | Greenhalgh |

FOREIGN PATENT DOCUMENTS

| | | |
|---|---|---|
| CN | 101007183 | 8/2007 |
| CN | 101401966 | 4/2009 |
| CN | 101461963 | 6/2009 |
| CN | 101618230 | 1/2010 |
| CN | 104876439 | 9/2015 |
| DE | 10338634 | 3/2005 |
| EP | 0 287 584 | 3/1992 |
| EP | 0 891 421 | 1/1999 |
| EP | 0 741 785 | 11/1999 |
| EP | 1 018 978 | 7/2000 |
| EP | 1 051 205 | 11/2000 |
| EP | 1 121 072 | 8/2001 |
| EP | 1 263 353 | 12/2002 |
| EP | 1 311 656 | 5/2003 |
| EP | 1 233 794 | 9/2003 |
| EP | 1 344 538 | 9/2003 |
| EP | 1 348 453 | 10/2003 |
| EP | 1 359 951 | 11/2003 |
| EP | 1 363 551 | 11/2003 |
| EP | 1 365 792 | 12/2003 |
| EP | 1 377 236 | 1/2004 |
| EP | 1 383 509 | 1/2004 |
| EP | 1 410 810 | 4/2004 |
| EP | 1 140 239 | 7/2004 |
| EP | 0 883 410 | 8/2004 |
| EP | 1 194 518 | 9/2004 |
| EP | 1 464 345 | 10/2004 |
| EP | 1 250 163 | 12/2004 |
| EP | 1 137 448 | 1/2006 |
| EP | 1 085 842 | 3/2006 |
| EP | 1 152 777 | 5/2006 |
| EP | 1 624 904 | 1/2007 |
| EP | 1 094 851 | 2/2007 |
| EP | 1 753 396 | 2/2007 |
| EP | 0 874 601 | 3/2007 |
| EP | 1 778 760 | 5/2007 |
| EP | 1 781 319 | 5/2007 |
| EP | 1 804 814 | 7/2007 |
| EP | 1 824 530 | 8/2007 |
| EP | 1 909 860 | 4/2008 |
| EP | 1 976 459 | 10/2008 |
| EP | 1 981 440 | 10/2008 |
| EP | 1 988 940 | 11/2008 |
| EP | 1 996 114 | 12/2008 |
| EP | 2 007 317 | 12/2008 |
| EP | 2 010 104 | 1/2009 |
| EP | 2 037 973 | 3/2009 |
| EP | 1 210 092 | 4/2009 |
| EP | 2 127 689 | 12/2009 |
| EP | 2 131 851 | 12/2009 |
| EP | 1 399 199 | 2/2010 |
| EP | 2 182 886 | 5/2010 |
| EP | 2 271 378 | 1/2011 |
| EP | 2 272 470 | 1/2011 |
| EP | 1 778 306 | 6/2011 |
| EP | 2 358 408 | 8/2011 |
| EP | 2 448 607 | 5/2012 |
| EP | 2 456 389 | 5/2012 |
| EP | 2 344 081 | 1/2013 |
| EP | 2 542 187 | 1/2013 |
| EP | 2 588 154 | 5/2013 |
| EP | 2 600 912 | 6/2013 |
| EP | 2 585 124 | 1/2014 |
| EP | 2 678 050 | 1/2014 |
| EP | 2 678 052 | 1/2014 |
| EP | 1 677 846 | 8/2014 |
| EP | 2 771 041 | 9/2014 |
| EP | 2 793 915 | 10/2014 |
| EP | 1 945 132 | 12/2014 |
| EP | 2 823 829 | 1/2015 |
| EP | 2 826 495 | 1/2015 |
| EP | 1 528 894 | 6/2015 |
| EP | 2 897 560 | 7/2015 |
| EP | 2 512 537 | 8/2015 |
| EP | 2 903 657 | 8/2015 |
| EP | 2 904 094 | 8/2015 |
| EP | 2 934 394 | 10/2015 |
| EP | 1 986 712 | 12/2015 |
| EP | 1 404 346 | 3/2016 |
| EP | 1 638 621 | 3/2016 |
| EP | 1 148 847 | 7/2016 |
| EP | 2 605 804 | 3/2017 |
| EP | 2 381 970 | 4/2017 |
| GB | 2513599 | 6/2013 |
| IN | 2011DE01996 | 1/2013 |
| KR | 101427305 | 8/2014 |
| WO | WO 98/016267 | 4/1998 |
| WO | WO 00/027316 | 5/2000 |
| WO | WO 10/115138 | 10/2000 |
| WO | WO 05/102281 | 11/2005 |
| WO | WO 07/011172 | 1/2007 |
| WO | WO 08/049242 | 5/2008 |
| WO | WO 08/102985 | 8/2008 |
| WO | WO 09/101228 | 8/2009 |
| WO | WO 11/58443 | 5/2011 |
| WO | WO 11/084731 | 7/2011 |
| WO | WO 12/134540 | 10/2012 |
| WO | WO 14/32099 | 3/2014 |
| WO | WO 14/110284 | 7/2014 |
| WO | WO 14/124496 | 8/2014 |
| WO | WO 14/147622 | 9/2014 |
| WO | WO 14/152113 | 9/2014 |
| WO | WO 14/099967 | 6/2015 |
| WO | WO 15/123733 | 8/2015 |
| WO | WO 15/123734 | 8/2015 |
| WO | WO 15/147834 | 10/2015 |

OTHER PUBLICATIONS

Bioventus Surgical, 2017, OsteoPlus, product brochure, 5 pp.
Globus Medical Allocate product, http://www.globusmedical.com/portfolio/allocate/, 2014, 2 pp.
IFGL Bio Ceramics Ltd, Nov. 20, 2008, Bone regenerative solutions for advanced dental surgeries, 3 pp.
Kumar et al., Jun. 2013, Bone grafts in dentistry, J. Pharm Bioallied Sci, 5(Suppl1):S125-S127.
Maxigen Biotech Inc., 2010, Formagraft® Bone Graft Substitute, product brochure, 1 p.
Medtronic, 2005, Mastergraft®, product brochure, 12 pp.
RTI Surgical, Inc., 2017 NanOss® Loaded Advanced Bone Graft Substitute, product brochure, 3 pp.
Straumann AG, Maxresorb® inject, product brochure, 2 pp.
Stryker Corporation 1998, Vitoss Bone Graft Substitute, product brochure, 2 pp.

(56) References Cited

OTHER PUBLICATIONS

Zimmer Biomet, 2017, CopiOs® Bone Void Filler, product brochure, 7 pp.
Third Party Submission Under 37 CFR 1.290 dated Apr. 4, 2017 in U.S. Appl. No. 14/992,954.

* cited by examiner

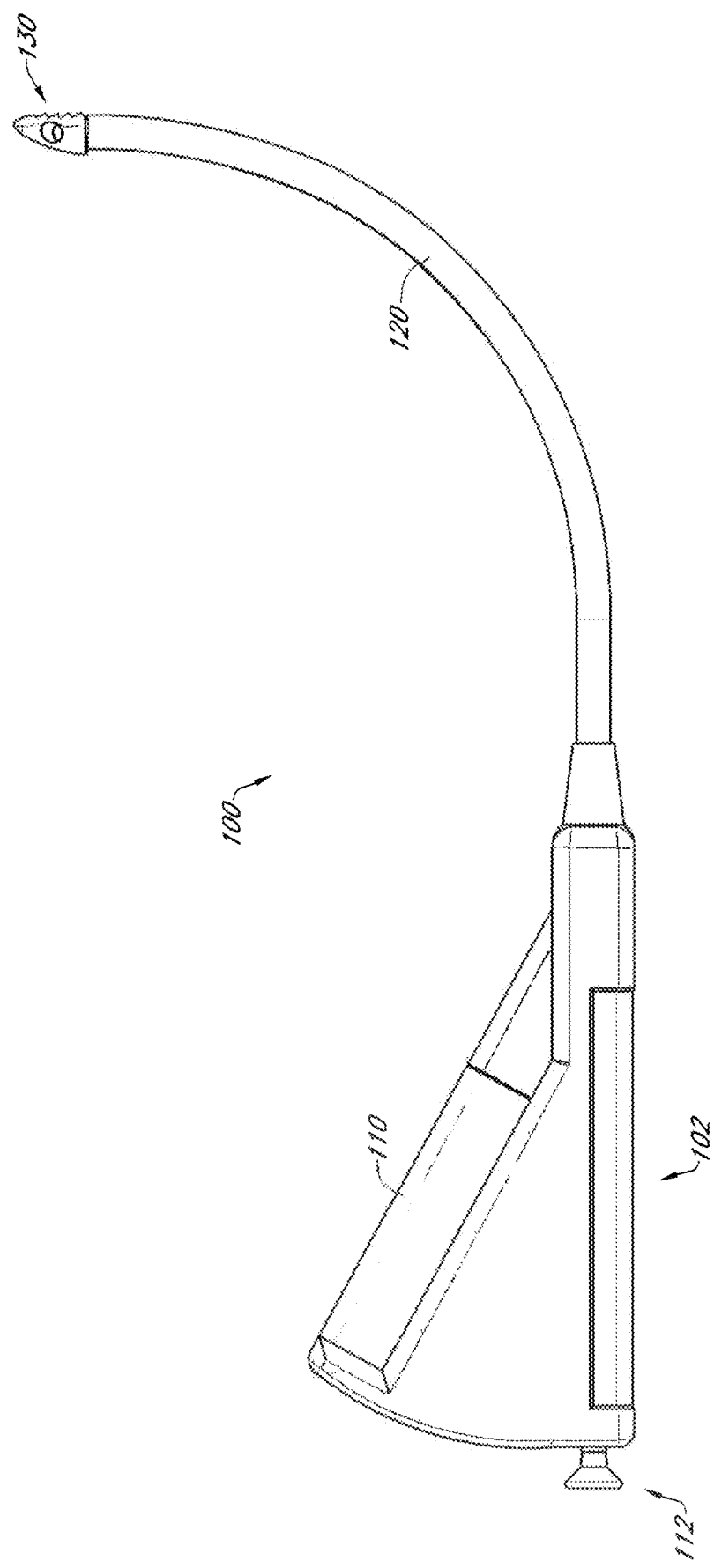

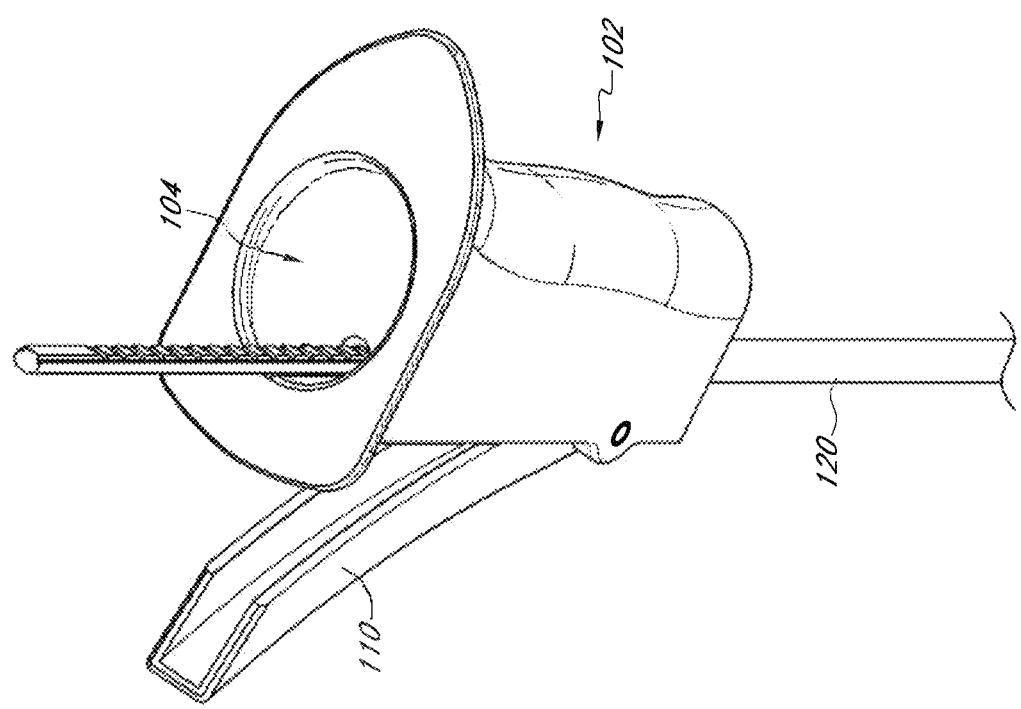

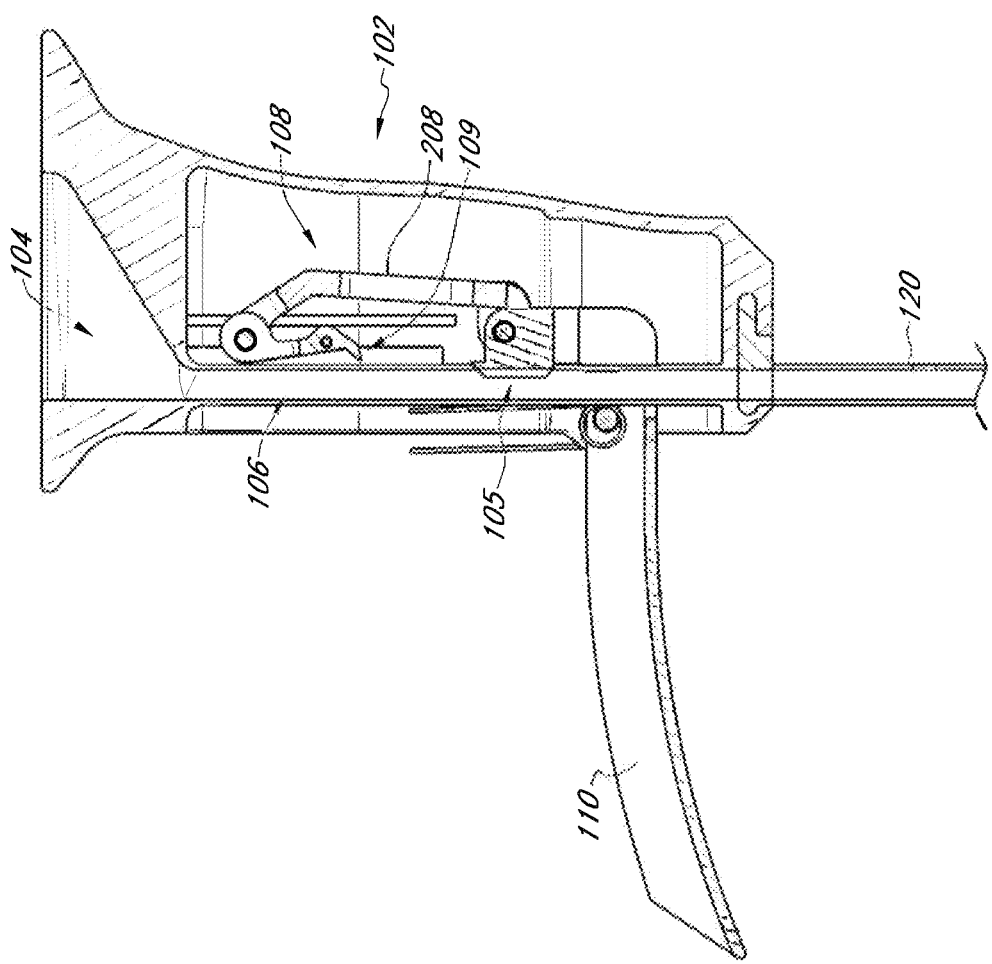

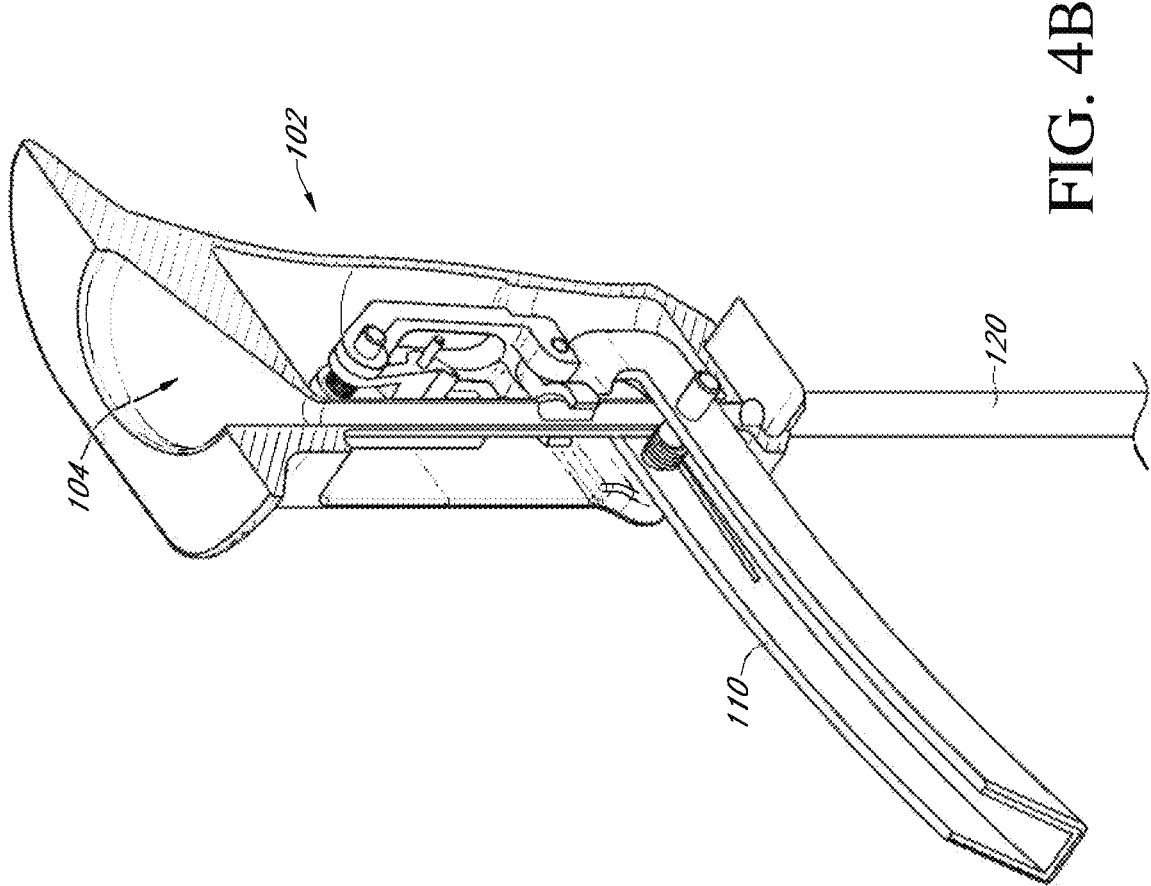

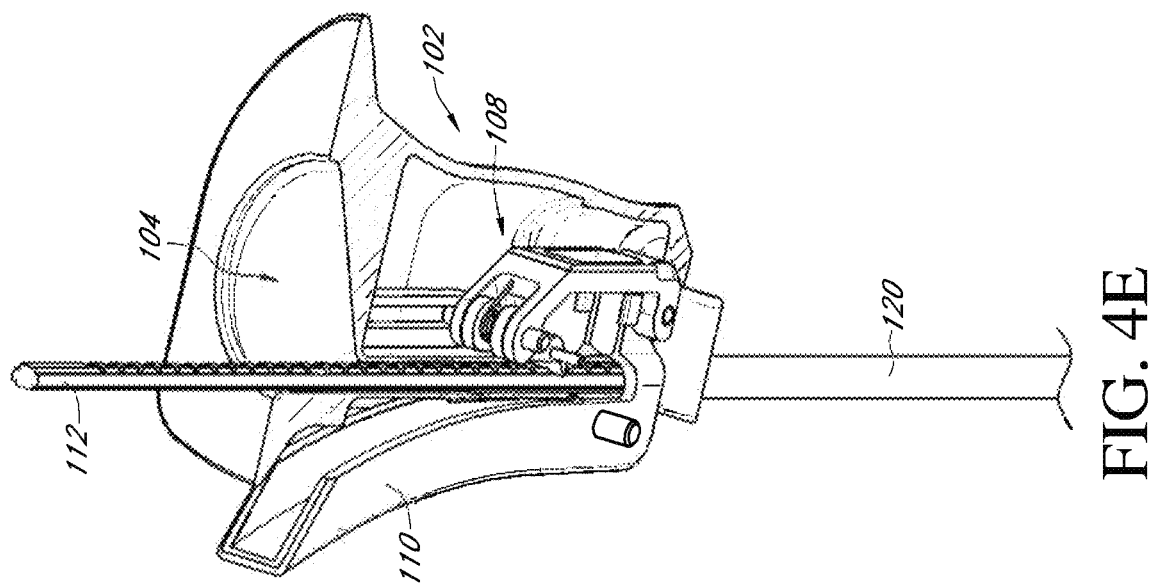

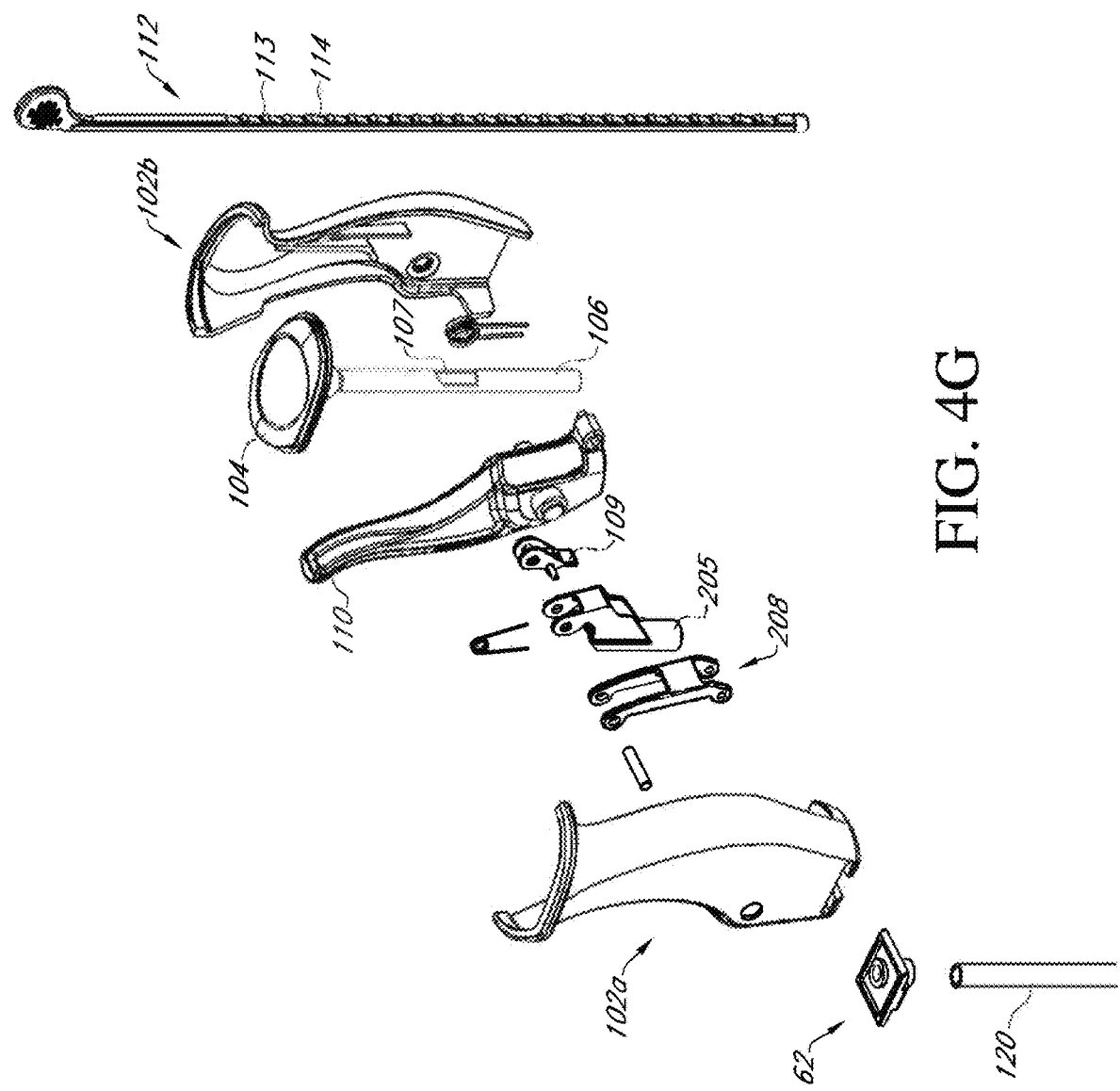

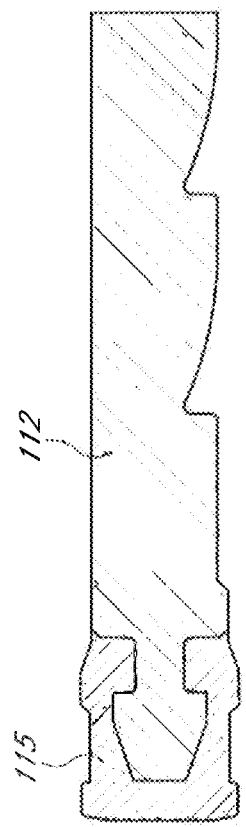
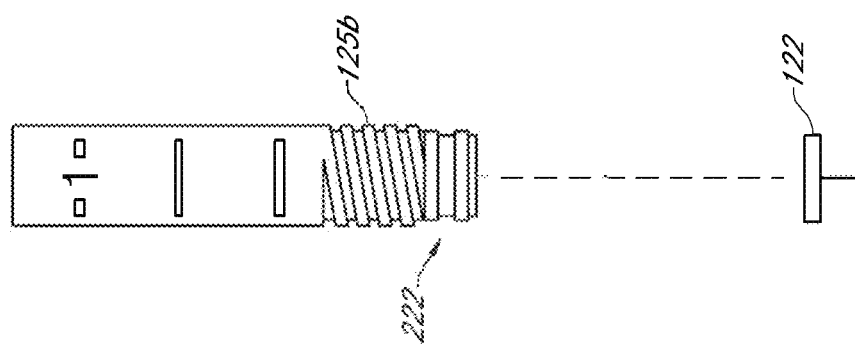

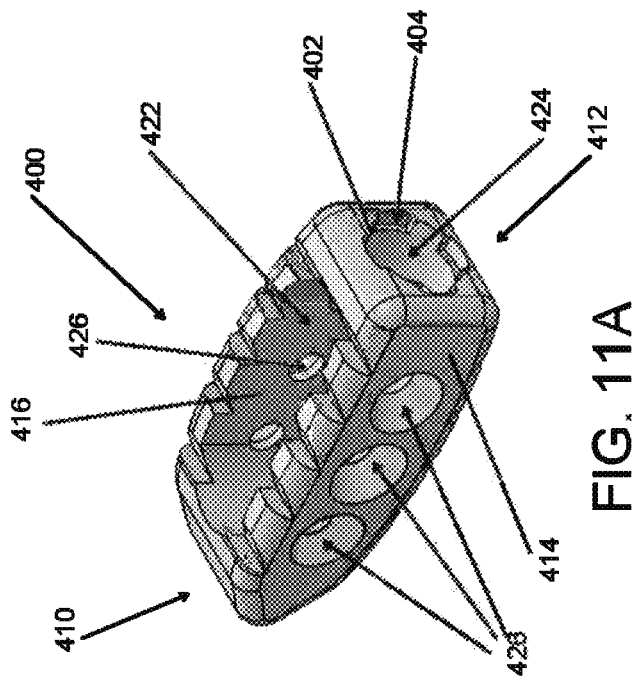
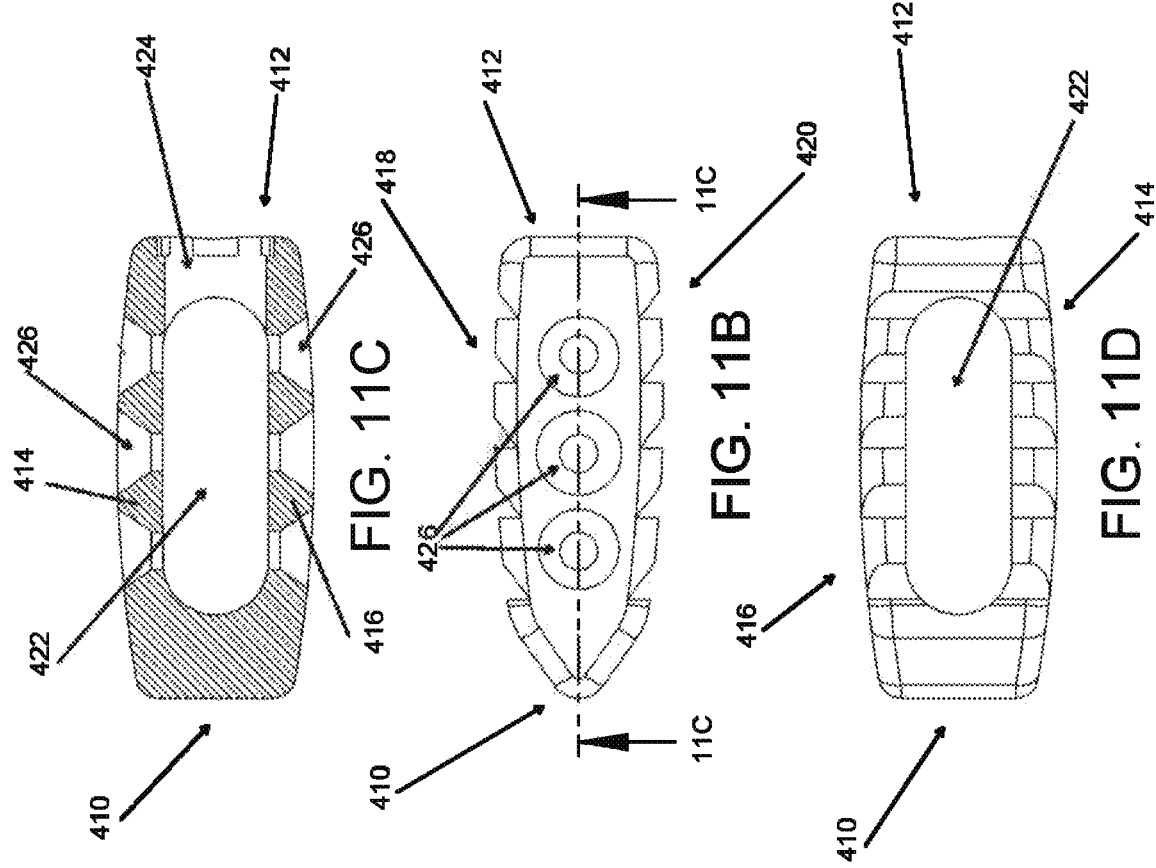

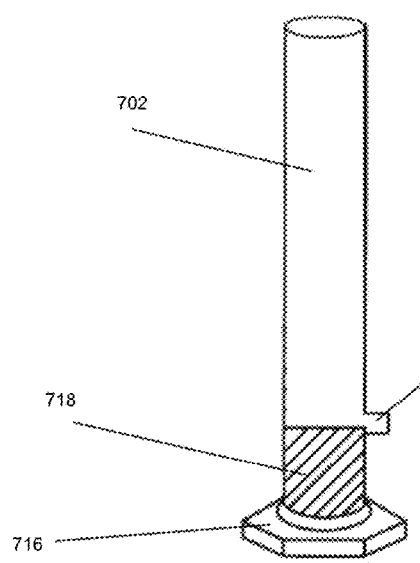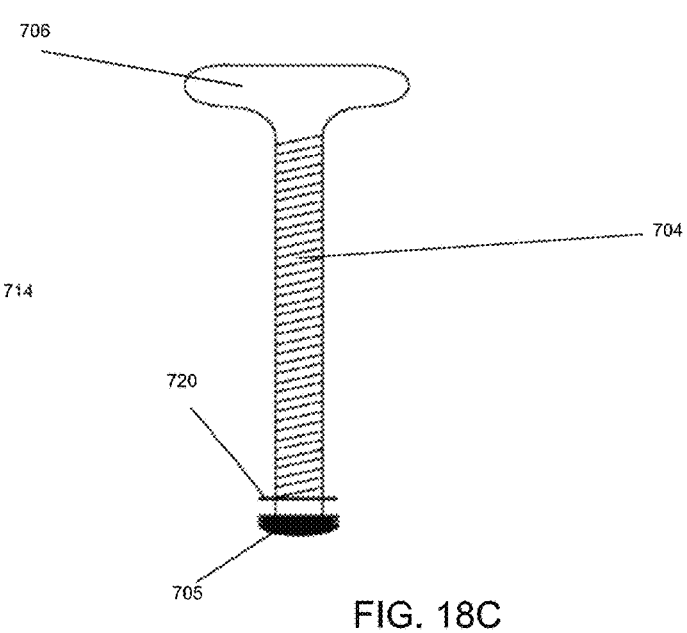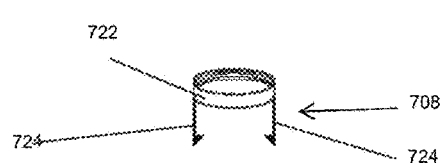
FIG. 18B
FIG. 18C
FIG. 18D

BONE GRAFT DELIVERY SYSTEM AND METHOD FOR USING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the priority benefit of U.S. Provisional Application No. 62/102,471, filed Jan. 12, 2015, the entirety of which is hereby incorporated by reference herein.

BACKGROUND

Field

The present application relates to orthopedic surgery in general, and more particularly, to bone graft delivery systems and methods.

Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can also be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

SUMMARY

The devices, systems, and methods described herein allow for minimally invasive delivery of bone graft material to a desired location in a patient's body. In some embodiments, the devices, systems, and methods described herein allow for delivery of bone graft material to a desired location in an open or mini-open procedure. In some embodiments, the devices, systems, and methods described herein also provide for bone decortication.

In some embodiments, a bone graft delivery system includes an elongated tube, a handle at a proximal end of the tube, and a tip at a distal end of the tube. The handle is configured to be actuated to deliver bone graft material through the tube. The tip includes one or more openings configured to deliver the bone graft material to a desired location and a surface suitable to serve as a rasp for scraping bone.

In some embodiments, the rasping surface of the tip includes jagged edges. The tip can be made of a metal, a radiopaque material, a durable medical plastic, a composite material, or another material or combination of materials. In some embodiments, the tip includes one or more radiopaque markers. The tip can have a sharp or blunt end. The tip can be removably attachable to the distal end of the tube. Alternatively, the tip can be integrally formed or permanently coupled to the distal end of the tube. In some embodiments the tube is rigid. In other embodiments the tube is at least somewhat bendable. In some embodiments the tube is straight, while in other embodiments the tube includes a permanent bend. The handle can include a trigger configured to be actuated to deliver the bone graft material through the tube. In some embodiments, the bone graft delivery system includes an endoscopic camera positioned adjacent the tip.

In some embodiments, a method for delivering bone graft material to a surgical location includes providing a bone graft delivery device and positioning the device adjacent the surgical location. The bone graft delivery device comprises an elongate tube and a distal tip. The distal tip includes at least one opening for delivering the bone graft material to the surgical location. The method further includes decorticating bone with the distal tip and delivering bone graft material through the tube and out the at least one opening of the tip.

The bone graft material can be one or more autogenous, allogenic, cadaveric, and/or synthetic materials. In some embodiments, the bone graft delivery device is positioned at the surgical location through a minimally invasive opening in a patient's skin. In some embodiments, the surgical location is a portion of the patient's spine, so the bone graft delivery device is positioned adjacent to the spine and the distal tip decorticates a portion of the spine. In some embodiments, decorticating bone with the distal tip is accomplished by rasping bone with jagged edges of the distal tip. In some embodiments, bone is decorticated with the distal tip by actuating the distal tip with mechanical, battery powered, electric, pneumatic, or other means of force.

In some embodiments, a bone graft delivery system includes an elongate tube and a handle at a proximal end of the tube configured to be actuated to deliver bone graft material through the tube. The tube can be removably coupled to the handle. In some embodiments, a distal end of the tube can be configured to couple to an interbody device disposed within a disc space to deliver bone graft within the interbody device. In some embodiments, the handle includes a trigger configured to be actuated to deliver bone graft material through the tube. In some embodiments, the handle includes a funnel configured to receive bone graft material, a channel in fluid communication with the funnel and the proximal end of the tube, and a ratcheting mechanism configured to advance bone graft material distally through the tube. The bone graft delivery system can further include a plunger configured to be removably received in the channel and tube.

The channel can include a window along at least one side of the channel, and the handle can further include a sheath movably disposed within the channel and configured to selectively cover the window of the channel. The ratcheting mechanism can include a pawl operatively coupled to the trigger, the plunger can include a series of notches, and the pawl can be configured to engage the notches of the plunger through the window of the channel when the plunger is inserted into the channel and the window is at least partially uncovered.

In some embodiments, a bone graft delivery system kit includes a handle, one or more elongate tubes configured to be coupled to the handle, and one or more plungers configured to be removably received in the handle and tube. The kit can further include one or more tips configured to be coupled to a distal end of the tube and having one or more openings configured to deliver bone graft material to a desired location and a surface configured to decorticate bone.

In some embodiments, a method for delivering bone graft material to a surgical location includes providing a bone graft delivery device. The bone graft delivery device can include an elongate tube and a handle at a proximal end of the tube that includes a ratcheting mechanism, a trigger operatively coupled to the ratcheting mechanism, a proximal opening, and a lumen extending between and in fluid communication with the proximal opening and proximal end of the tube. The method further includes loading bone graft material into the bone graft delivery device, for example into the proximal opening, inserting a plunger into the lumen and tube, and manipulating the trigger so that the ratcheting mechanism engages the plunger. In some embodiments, the method further includes coupling a distal end of the elongate tube to an interbody implant positioned within a disc space and delivering bone graft material within the interbody implant.

In some embodiments, an interbody implant includes a leading end, a trailing end, first and second sidewalls extending between the leading end and the trailing end, and a central opening bounded by the leading end, trailing end, and first and second sidewalls. The trailing end includes a hole in fluid communication with the central opening, and a perimeter of the hole includes engagement features configured to mate with corresponding engagement features on a distal end of a tube of a bone graft delivery device. At least one of the first and second sidewalls can include at least one hold in fluid communication with the central opening. A perimeter of the at least one hole can be tapered outwardly from an inner surface to an outer surface of the at least one of the first and second sidewalls.

BRIEF DESCRIPTION OF THE DRAWINGS

FIG. 1A illustrates a side view of an example embodiment of a bone graft delivery device;
FIG. 3 illustrates a perspective view of a handle of a bone graft delivery device including a funnel for introduction of bone graft;
FIGS. 4A-4E are section views illustrating operation of an example embodiment of a ratcheting mechanism in a handle of a bone graft delivery device;
FIGS. 4F and 4G illustrate exploded views of an example embodiment of a bone graft delivery device including a ratcheting mechanism;
FIG. 4O illustrates an exploded view of the bone graft delivery device of FIG. 4N;
FIG. 4W illustrates a radiopaque ring configured to be placed on a distal end of a tube of a bone graft delivery device;
FIG. 4X illustrates a section view of a distal end of a plunger of a bone graft delivery device;
FIG. 11A illustrates a perspective view of an example embodiment of an interbody device configured to be coupled to a bone graft delivery device;
FIG. 11B illustrates a side view of the interbody device of FIG. 11A;
FIG. 11C illustrates a section view of the interbody device of FIGS. 11A-11B taken along line 11C-11C in FIG. 11B;

FIG. 11D illustrates a top view of the interbody device of FIGS. 11A-11C;

FIG. 18B illustrates a tube body and base of the bone graft loading device of FIG. 18A;

FIG. 18C illustrates a plunger of the bone graft loading device of FIG. 18A; and FIG. 18D illustrates a cap or coupling of the bone graft loading device of FIG. 18A.

DETAILED DESCRIPTION

Figure 1B:
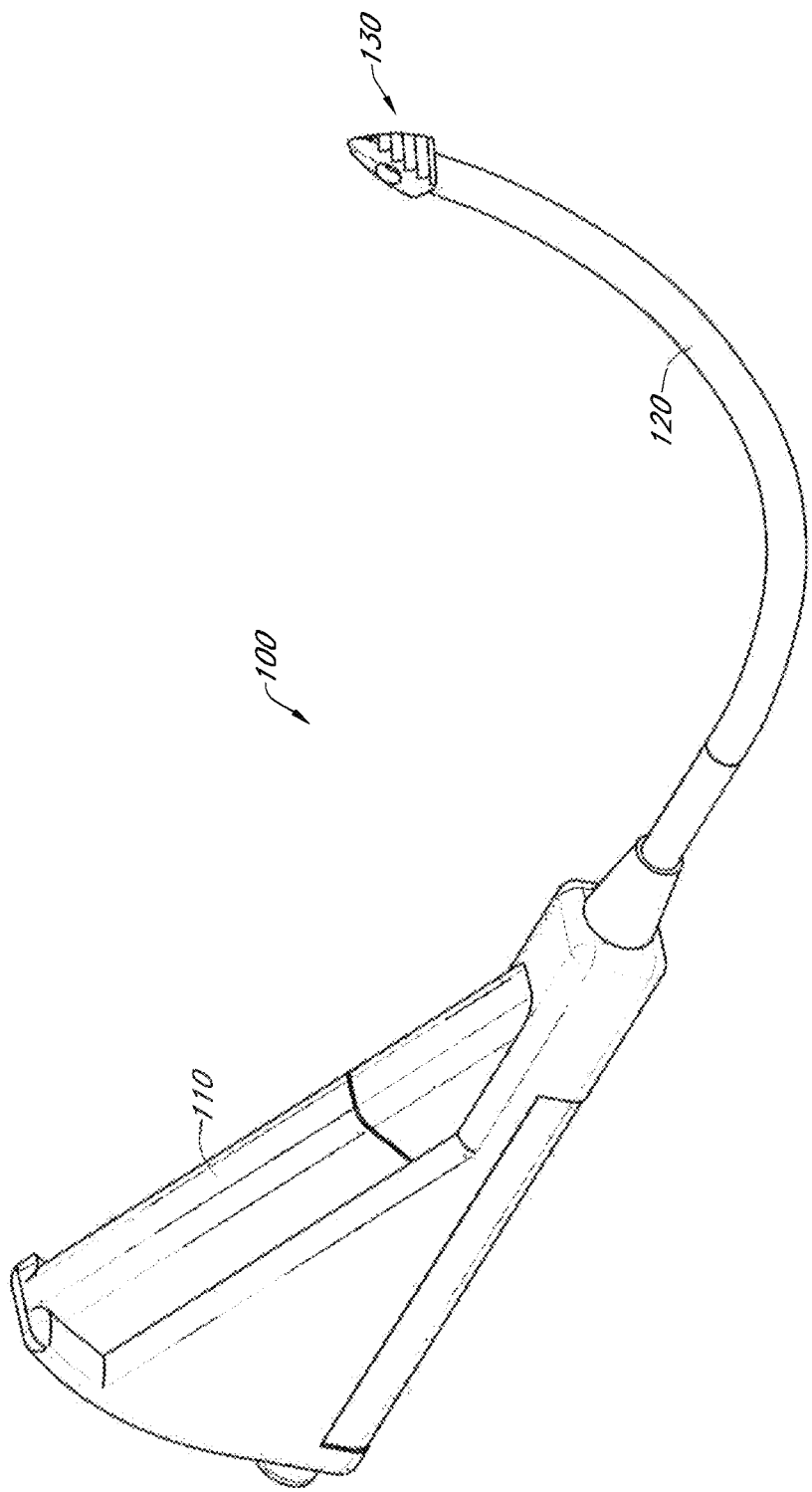
FIG. 1B illustrates a perspective view of the bone graft delivery device of FIG. 1A.

As shown in FIGS. 1A and 1B, an example embodiment of a bone graft delivery device 100 generally includes a handle 102 having a trigger 110 or other actuation mechanism, a tube 120 having a lumen therethrough, and a distal tip 130. In the illustrated embodiment, the bone graft delivery device 100 is similar to a caulking gun. The handle 102 can house a supply of the desired bone graft material. The bone graft material can be pre-loaded in the handle 102 or tube 120 or can be supplied to the handle, for example, via a cartridge that can be removably coupled to the handle 102. In some embodiments, the device 100 can further include a plunger 112 that is retracted proximally to allow the handle to receive a cartridge or pre-loaded volume of bone graft material. In some embodiments, for example as shown in the example embodiment of FIGS. 2A and 2B, the bone graft delivery device 100 does not include a distal tip 130. In some embodiments, the bone graft delivery device does not include a rasping distal tip as described in greater detail herein.

In use, the trigger 110 is actuated to deliver bone graft material through the tube 120 and distal tip 130 to a desired surgical location. In some embodiments, the plunger 112 is simultaneously pushed distally to help deliver bone graft material through the tube 120. In some embodiments, the trigger 110 or other actuation mechanism is configured to deliver a controlled release amount of bone graft material during actuation of the device, for example, ½ cc of bone graft material per complete squeeze of the trigger 110. The trigger 110 or other actuation mechanism may be operated manually or by mechanical, battery powered, electric, pneumatic, or any other means of force.

Figure 2A:
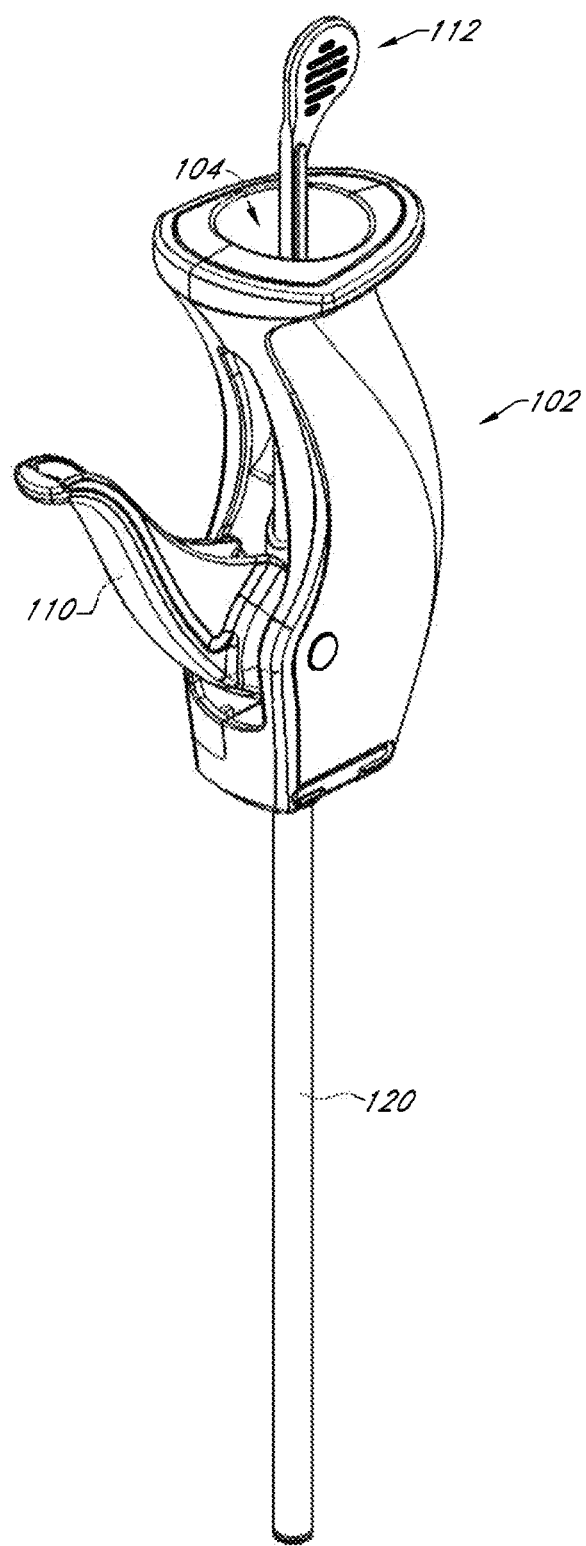
FIGS. 2A and 2B illustrate perspective views of another example embodiment of a bone graft delivery device.
Figure 2B:
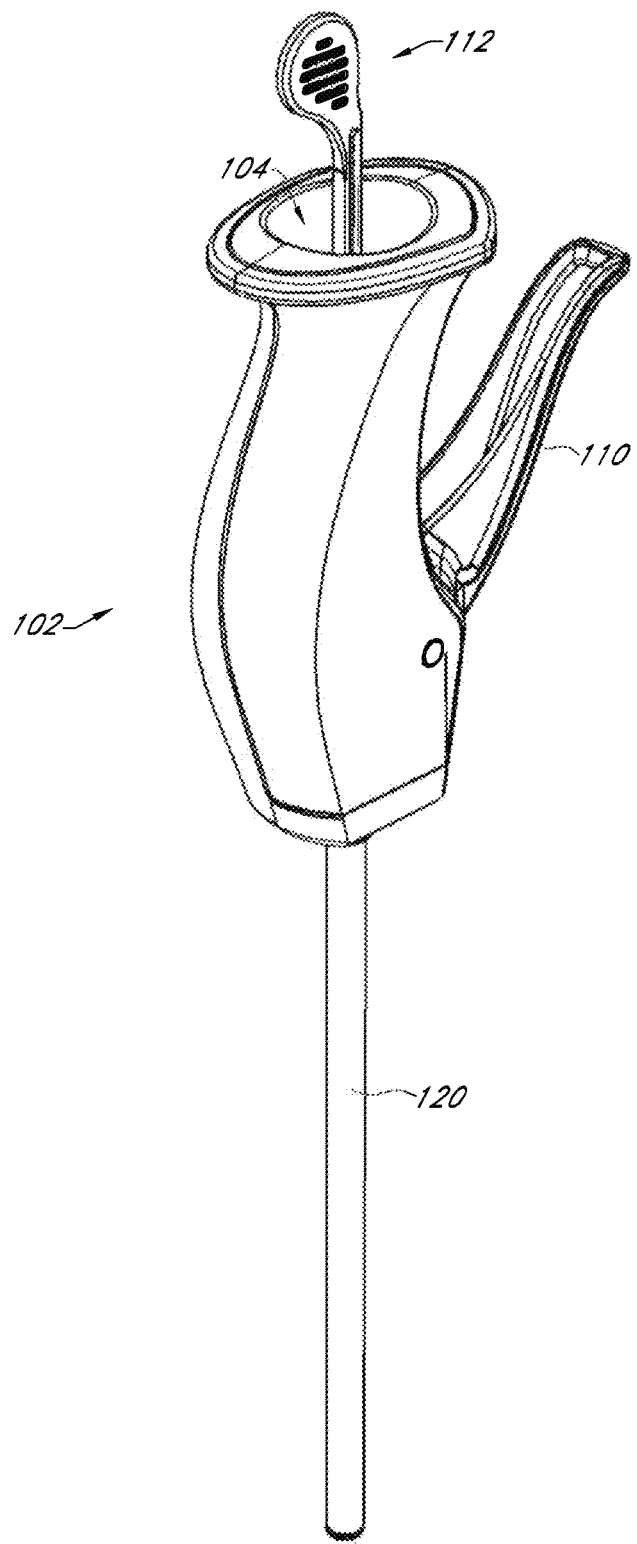

In some embodiments, a portion of the handle 102 can include an opening configured to receive the bone graft material. For example, a base of the handle 102 can include a funnel 104 as shown in FIGS. 2A-2B and 3. In other embodiments, a side or another portion of the handle 102 can include a funnel 104 or other opening configured to receive the bone graft material, for example as shown in FIGS. 2C-2K. Whereas some existing bone graft delivery devices are only compatible with certain, e.g., pre-packaged, bone graft materials, the funnel 104 can be designed to advantageously allow the user to use any bone graft material or combination of bone graft materials he or she wishes or deems appropriate. For example, the user can use synthetic, autologous, stem cell, DMB, cadaveric, and/or any other available bone graft material. The handle 102 can further include a channel or funnel shaft 106 extending therethrough connecting and in fluid communication with the funnel 104 and tube 120. In use, the user can mix the desired bone graft material in the funnel 104, then use the plunger 112 or other means to advance the bone graft material through the channel 106 and into the tube 120 for delivery.

In some embodiments, the handle 102 includes a ratcheting mechanism 108 configured to advance the plunger 112 and bone graft material from the funnel 104 and through the channel 106 and tube 120 for delivery, as shown in FIGS. 4A-4E. The ratcheting mechanism 108 (or any of the ratcheting mechanisms described herein) and plunger 112 can advantageously create pressure on the bone graft material in the tube 120 to improve delivery to the target location. In some embodiments, the plunger 112 fully or substantially seals with the inner diameter of the tube 120. This can create a vacuum within the tube 120 and/or can provide greater pressure on the bone graft material to force the bone graft material through the tube 120 and out of the distal end of the tube 120 or distal tip 130. In some embodiments, the plunger 112 or a portion of the plunger 112 is made of, for example, rubber silicone, which can help improve the seal with the tube 120 and/or can help provide pressure on the bone graft material. In some embodiments, the plunger 112 can be made of a plastic or another material and can include an elastomeric rubber stopper 115 at the distal end, for example as shown in FIG. 4O. The stopper 115 can be dual injection molded or co-molded with the plunger 112 so that the stopper 115 cannot normally be removed from the plunger 112. As shown in FIG. 4X, the stopper 115 can be molded onto or over a barb-shaped distal end of the plunger 112. The plunger 112 and ratcheting mechanism 108 can therefore allow the bone graft delivery device to extrude even highly viscous and/or granular bone graft material.

Figure 4C:
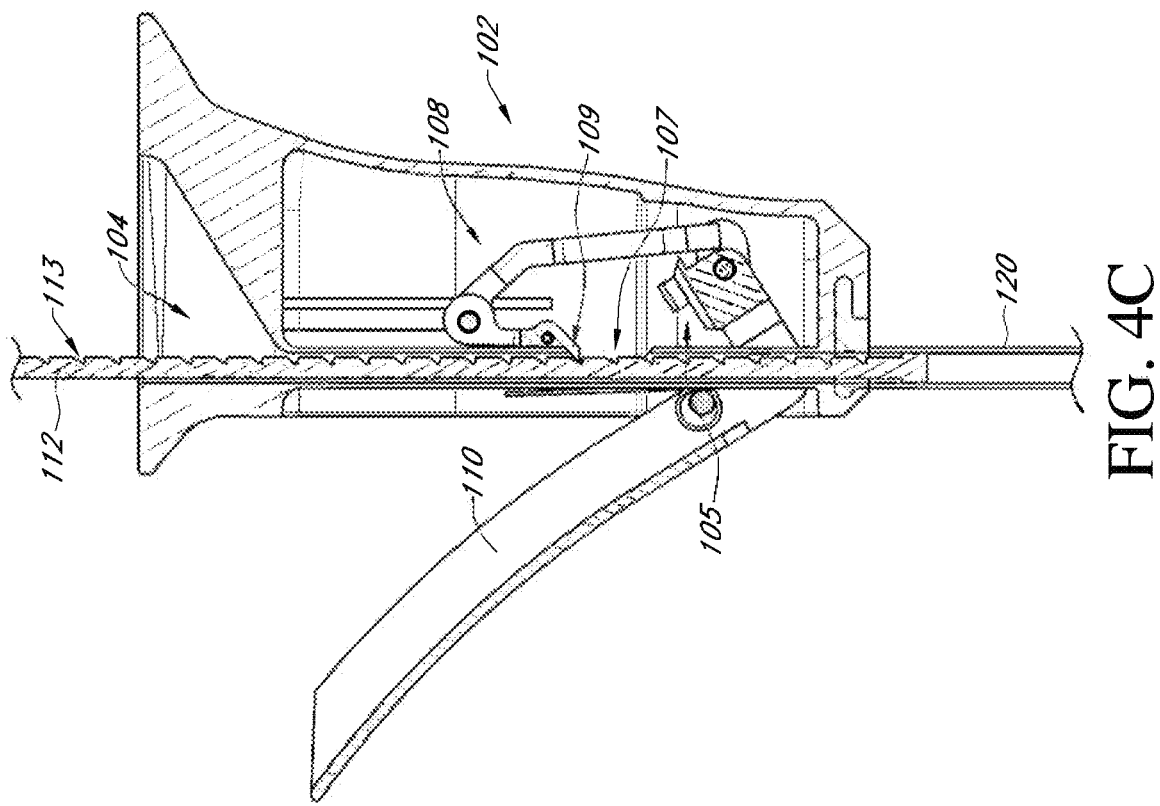
Figure 4D:
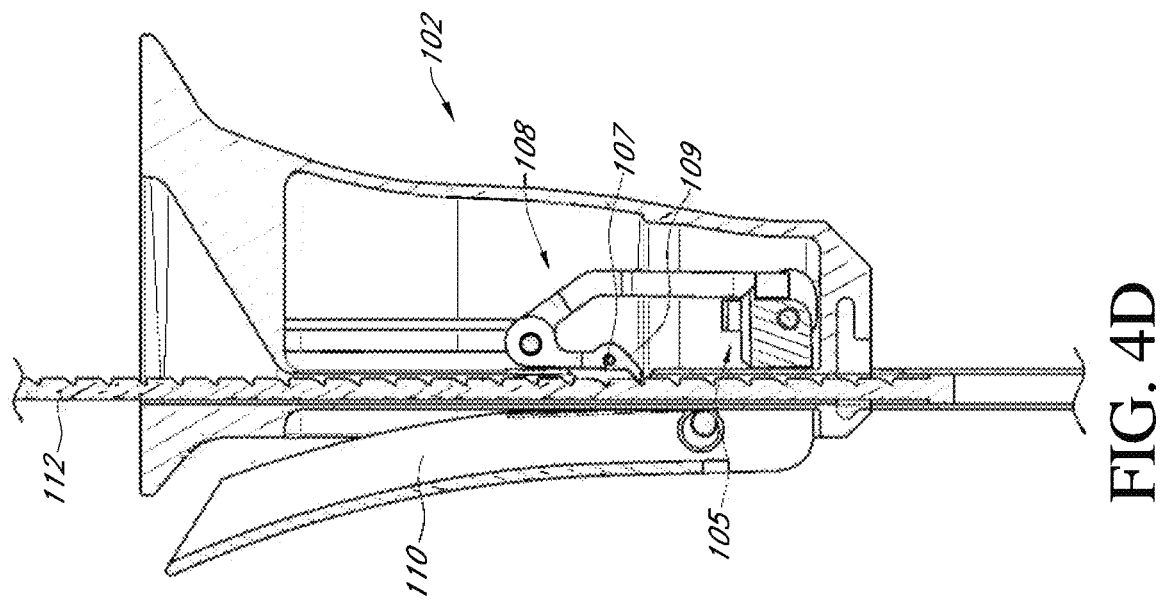
Figure 4F:
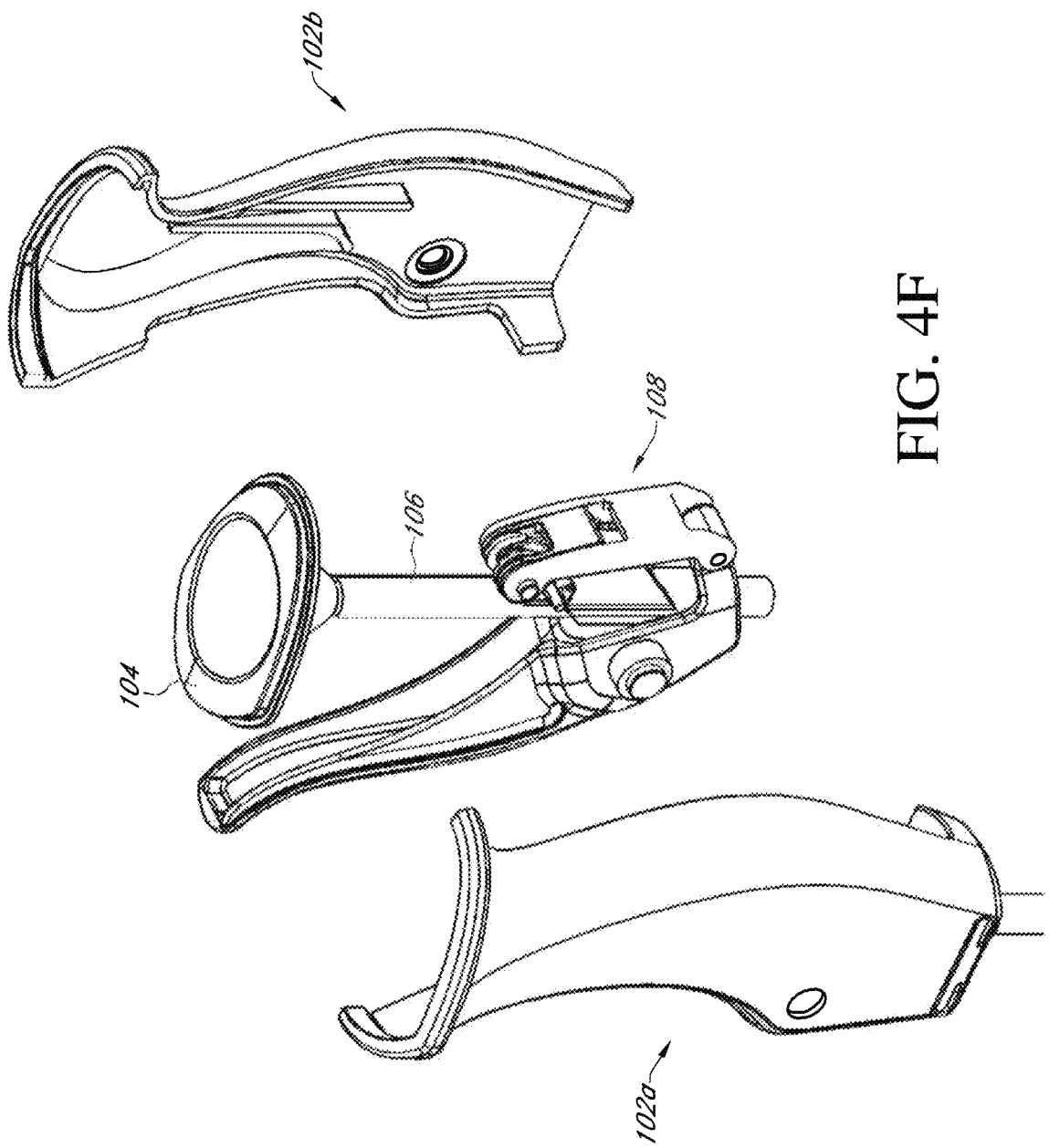

In the illustrated embodiment, the ratcheting mechanism 108 includes a cover 105 and a pawl 109 coupled to the trigger 110 via an arm 208. The funnel shaft 106 includes a window 107 in a portion of the shaft 106 facing the pawl 109. The plunger 112 can be made of a rigid or flexible material. For example, the plunger 112 can be plastic, carbon fiber, metal, or any other suitable material. The plunger 112 includes a series of teeth 114 and notches 113 located between the teeth 114 and configured to receive the pawl 109. The notches 113 can be generally triangular. As shown, distal edges of the teeth 114 slope proximally toward the outer edge of the plunger 112 to allow the pawl 109 to slide along the distal edges in use. In some embodiments, extending the trigger 110 away from the handle 102, for example to a position perpendicular to the handle 102, causes the cover 105 to rest in and close the window 107 of the funnel shaft 106, as illustrated in FIGS. 4A and 4B, to allow for loading of the bone graft material through the funnel 104 into the channel 106. In this position, the pawl 109 rests proximal to the window 107. The plunger 112 can be inserted into the funnel 104 and channel 106 to advance some or all of the bone graft material past the window 107. Once the bone graft material has been loaded, the trigger 110 can be moved toward the handle 102 to an intermediate position, as shown in FIG. 4C. This moves the pawl 109 distally so that the pawl 109 engages one of the notches 113 on the plunger 112 through the window 107. Movement of the trigger 110 to a final position closest the handle 102 causes the pawl 109 to move distally within the window 107 (or away from the funnel 104 and toward the tube 120), thereby advancing the plunger 112 distally within the channel 106 to force the bone graft material distally within the channel 106 and/or tube 120, as shown in FIGS. 4D and 4E. The trigger 110 can be moved back to the intermediate position to cause the pawl 109 to slide proximally along the plunger 112 and over one of the teeth 114 to engage a more proximal notch 113. The trigger 110 can be moved between the intermediate position and final position multiple times until the pawl 109 has reached the proximal end of the plunger 112. The user can re-load the device 100 as needed during a procedure. The ratcheting mechanism 108 and trigger 110 in combination can advantageously provide a mechanical advantage and allow the user to apply a greater force in operating the bone graft delivery device 100 and/or delivering the bone graft material compared to, for example, a standard syringe used to deliver bone graft material.

Figure 4H:
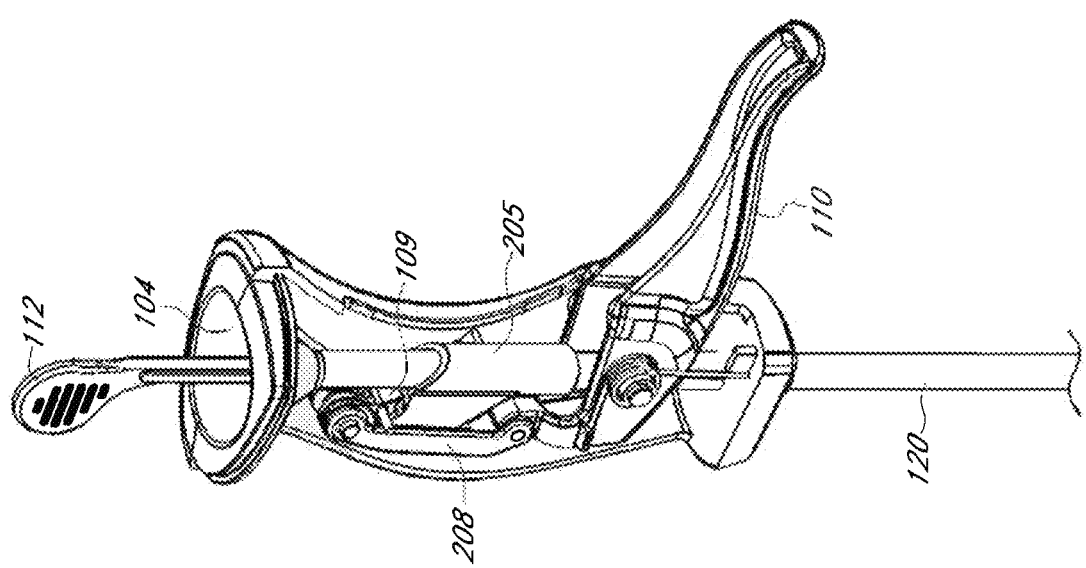
FIGS. 4H-4M illustrate operation of the ratcheting mechanism of the device of FIGS. 4F and 4G.
Figure 4I:
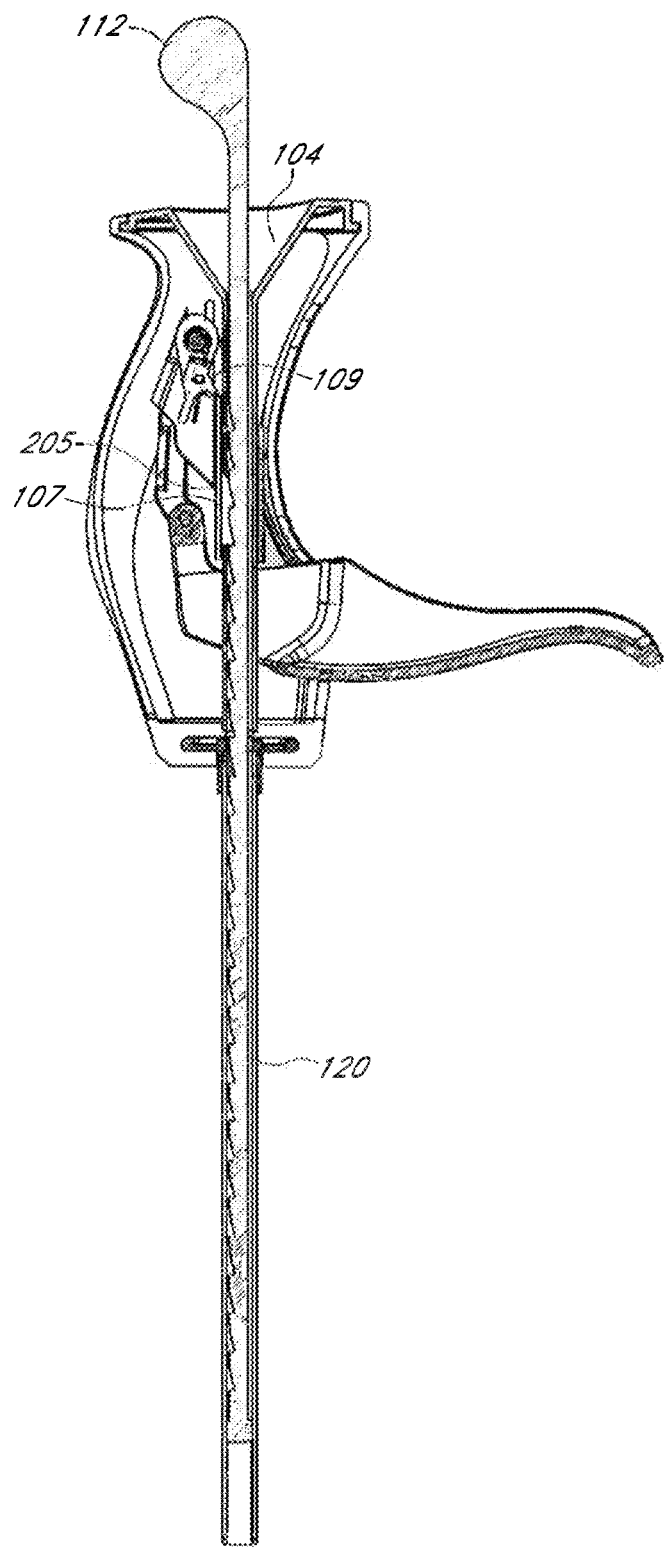
Figure 4J:
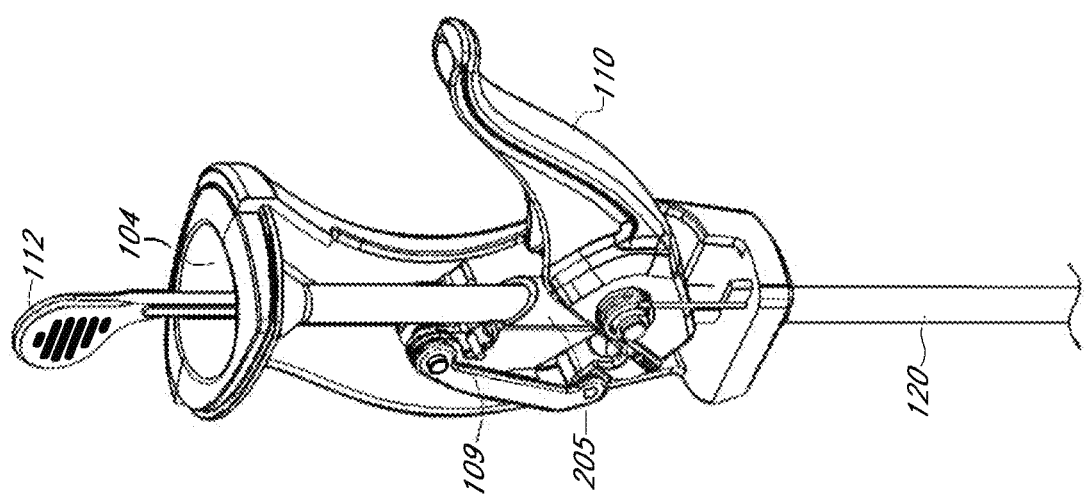
Figure 4K:
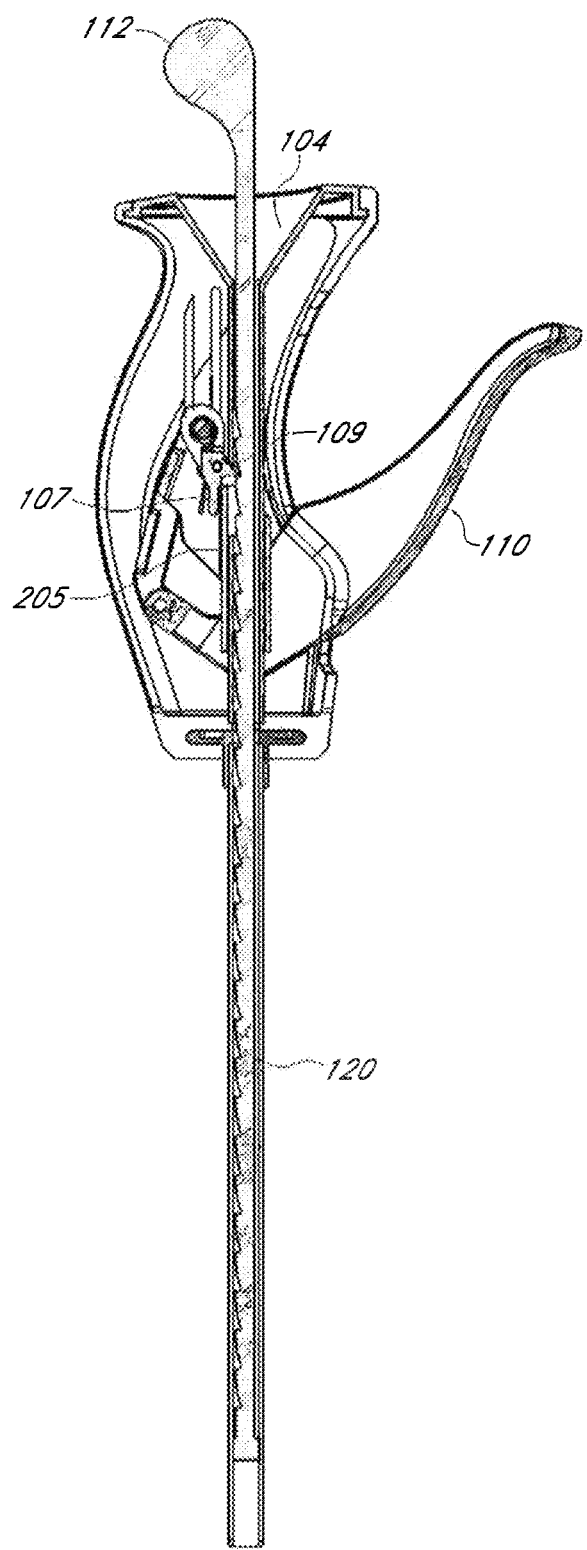
Figure 4L:
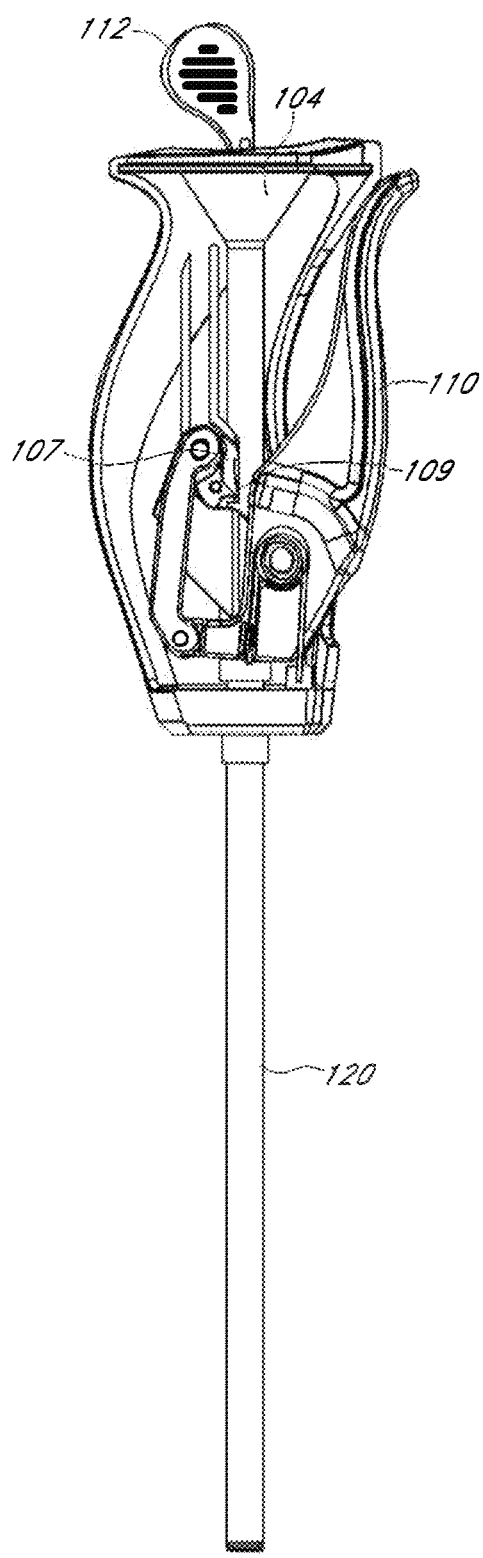
Figure 4M:
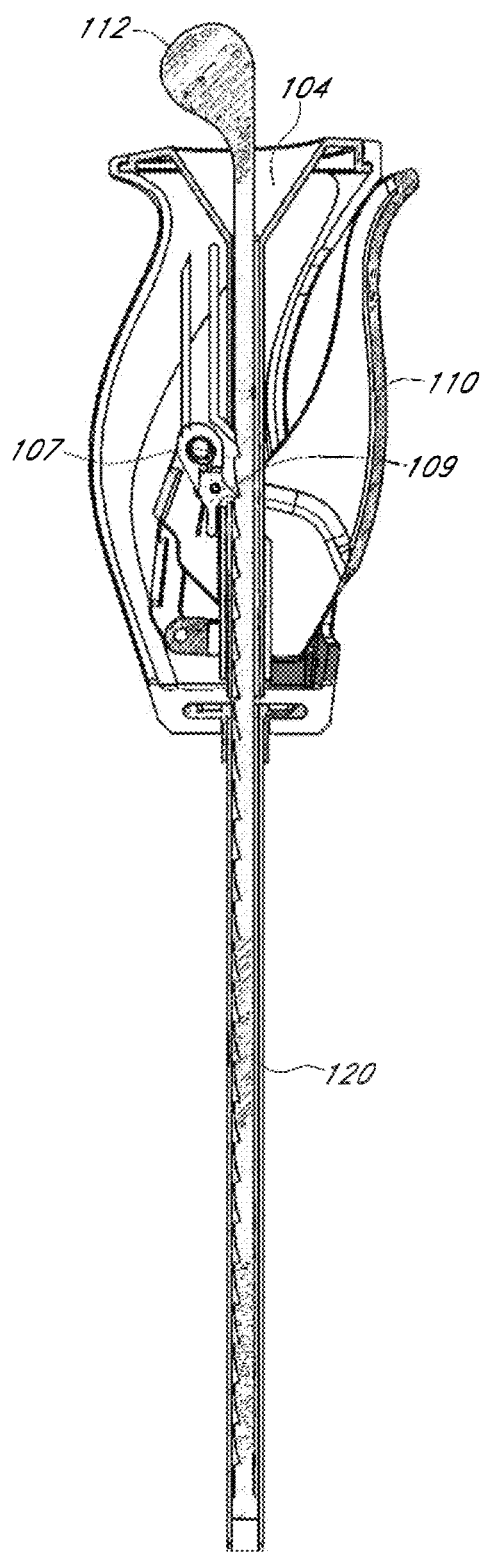

Another example embodiment of a handle 102 and ratcheting mechanism 108 is shown in FIGS. 4F-4M. In this embodiment, the handle 102 includes a two-part clamshell housing 102a, 102b that houses the funnel 104, funnel shaft 106, and ratcheting mechanism 108 assembly as shown in the exploded views of FIGS. 4F and 4G. The ratcheting mechanism 108 includes the pawl 109 and a sheath 205 coupled to the trigger 110 via arm 208. The plunger 112 includes a series of sloped teeth 114 alternating with notches 113 that are configured to receive the pawl 109. When the trigger 110 is in the first position, as shown in FIGS. 4H and 4I, the sheath 205 covers the pawl window 107 and the pawl 109 rests proximal to the window 107. Movement of the trigger 110 to the intermediate position causes the sheath 205 and pawl 109 to move distally, exposing the window 107 and allowing the pawl 109 to engage the plunger 112, as shown in FIGS. 4J and 4K. Movement of the trigger 110 to the final position causes the pawl 109 to move distally, advancing the plunger 112 distally, as shown in FIGS. 4L and 4M.

Yet another example embodiment of a handle 102 and ratcheting mechanism 108 is shown in FIGS. 4N-4T. In this embodiment, the funnel shaft 106 includes an upper shaft portion 106a and a lower shaft portion 106b, and the lower shaft portion 106b has an outer diameter smaller than an outer diameter of the upper shaft portion 106a. As shown in FIGS. 4P-4T, the outer diameter of the lower shaft portion 106b can be approximately the same as an inner diameter of the upper shaft portion 106a, and the shaft 106 can include a step 206 (shown in FIG. 4R) at a transition point between the upper shaft portion 106a and lower shaft portion 106b. In the illustrated embodiment, the upper 106a and lower 106b shaft portions are integrally formed. In other embodiments, the upper 106a and lower 106b shaft portions can be separate pieces, and a proximal end of the lower shaft portion 106b can be coupled to an inner perimeter of a distal end of the upper shaft portion 106a. The upper shaft portion 106a includes a first window 107a for the pawl 109 and a second window 107b on an opposite side of the upper shaft portion 106a from the first window 107a. A sheath 305 is disposed within or inside the upper shaft portion 106a, and in the illustrated embodiment, a lever 308 extends from the trigger 110 and engages the sheath 305 through the second window 107b, as shown in FIGS. 4P-4T.

Figure 4N:
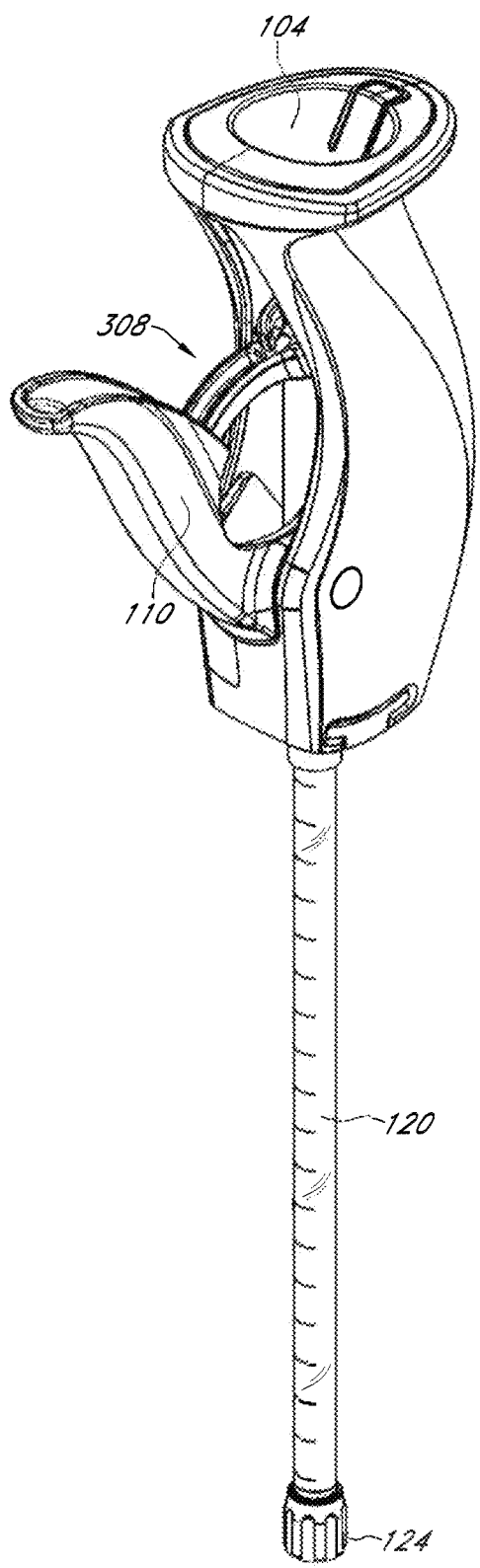
FIG. 4N illustrates a perspective view of an example embodiment of a bone graft delivery device including a ratcheting mechanism.
Figure 40:
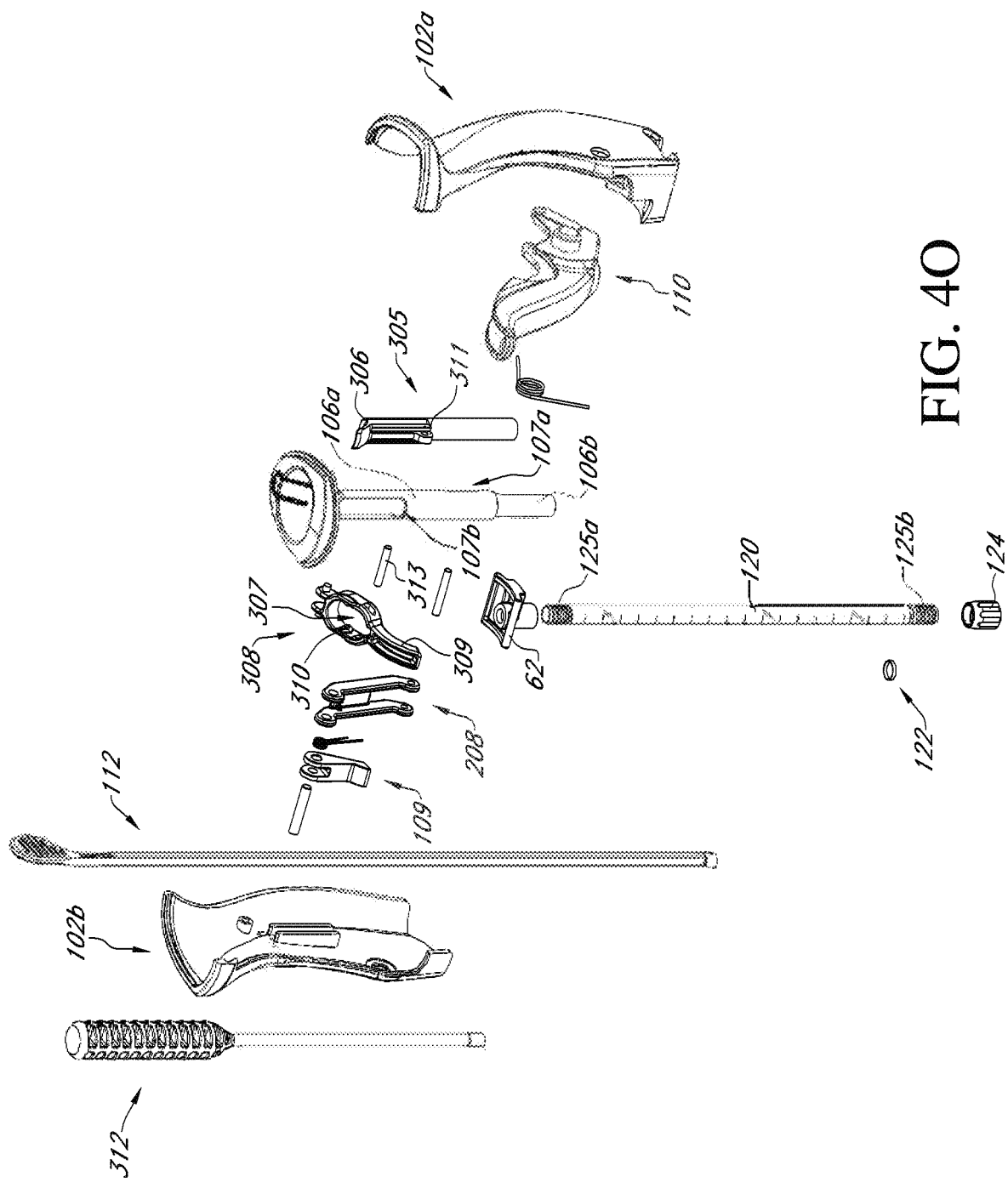
Figure 4P:
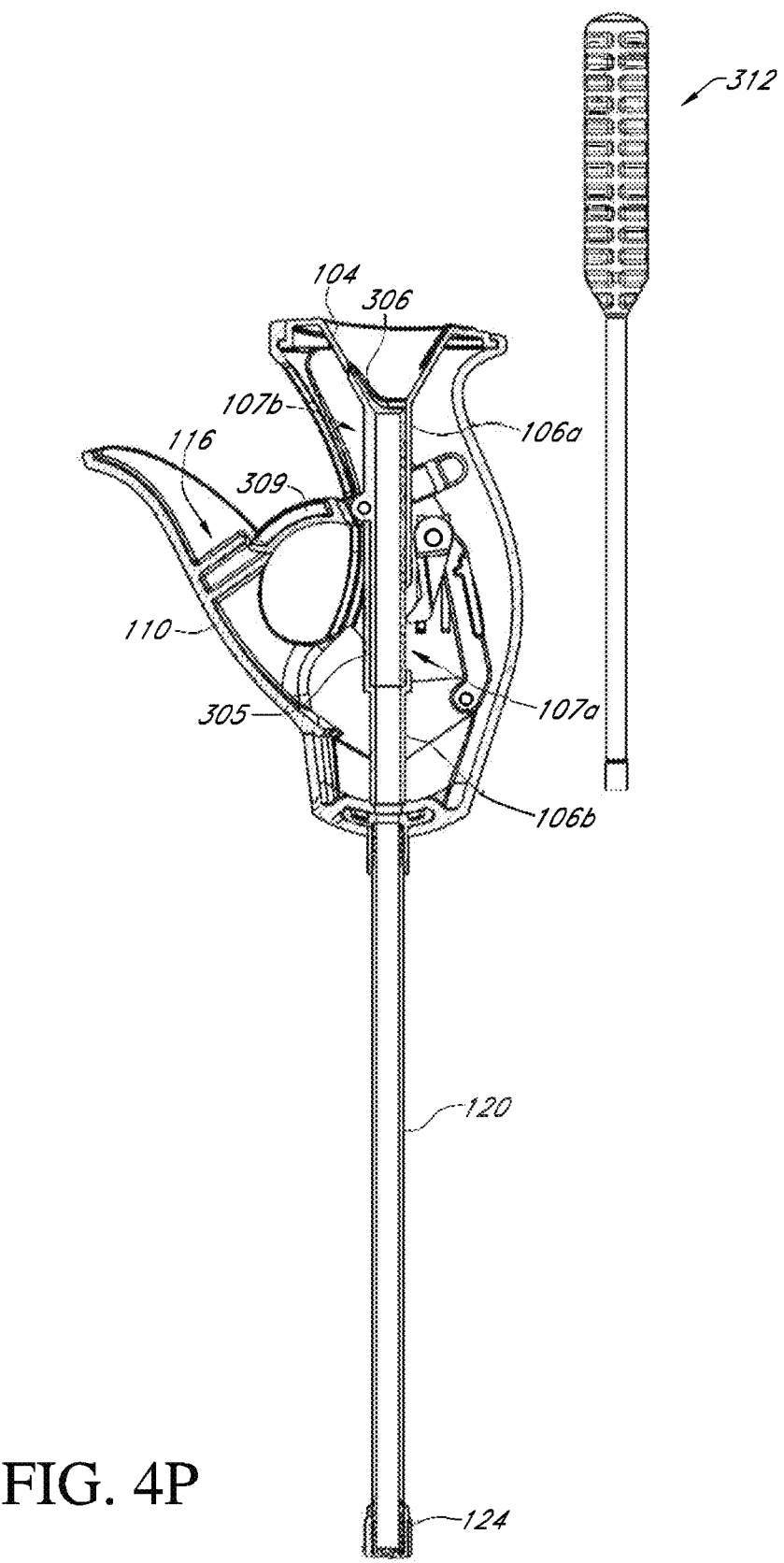
FIGS. 4P-4T are section views illustrating operation of the ratcheting mechanism of the device of FIGS. 4N and 4O.
Figure 4Q:
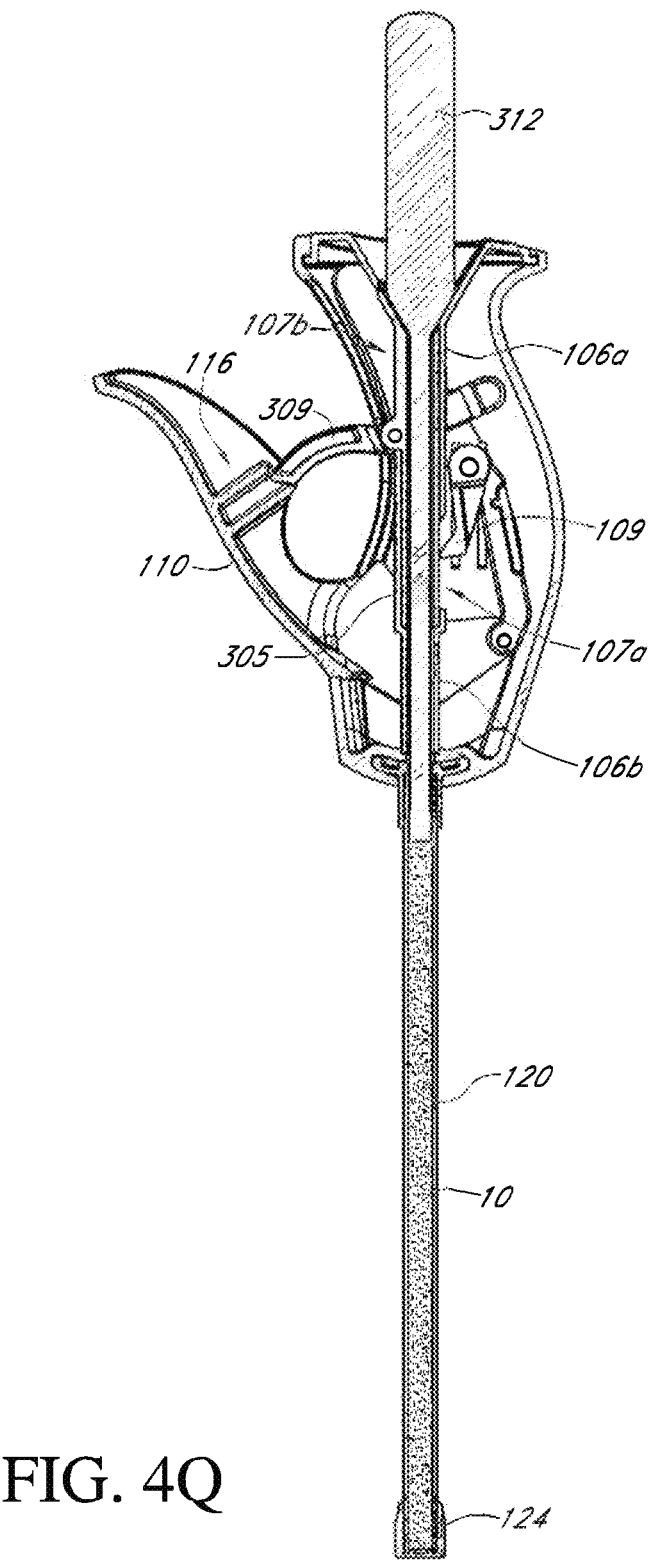

In some embodiments, the lever 308 is integrally formed with the sheath 305. Alternatively, the lever 308 can be coupled to the sheath 305, for example, with a pin 313. In some embodiments, the lever 308 includes a body 310 having a generally circular or ovular aperture 307, and an arm 309 extending from one end of the body 310. The aperture 307 receives the funnel shaft 106 so that the body 310 surrounds the upper shaft portion 106a. The sheath 305 includes a protrusion 311 that can extend through or over the second window 107b when the sheath 305 is disposed in the upper shaft portion 106a. The protrusion 311 is aligned with the lever body 310 with the protrusion 311 disposed in the aperture 307. The pin 313 extends through holes in the body 310 and protrusion 311 to couple the sheath 305 to the lever 308. In some embodiments, the pin 313 is secured to the protrusion 311 and lever body 310 with a weld, glue, or other appropriate means. The free end of the arm 309 of the lever 308 releasably engages the trigger 110. For example, the trigger 110 can include a track 116 configured to releasably receive the arm 309 as shown in FIGS. 4P and 4Q, and the arm 309 can engage the track 116 via, for example, a snap fit. In some embodiments, the trigger 110 is biased or naturally rests at a distance from the handle body that holds the arm 309 in the track 116. The trigger 110 can be flexed or allowed to move slightly away from the handle body to release the arm 309.

In some embodiments, the sheath 305 has an outer diameter about the same and slightly less than the inner diameter of the upper shaft portion 106a and a thickness about the same as a thickness of the lower shaft portion 106b. The sheath 305 can include an upper lip 306, and a length of the sheath 305 can be selected such that in an initial loading position, shown in FIG. 4P, the lip 306 rests against an inner surface of the funnel 104 and a distal end of the sheath 305 rests against the step 206. In the loading position, the sheath 305 covers the first window 107a. The dimensions of the upper shaft portion 106a, lower shaft portion 106b, and sheath 305 advantageously allow the sheath 305 to be substantially flush with an inner surface of the upper shaft portion 106a and step 206 and provide a substantially smooth and constant-diameter inner passageway from the sheath 305 to the lower shaft portion 106b. The bone graft delivery device of FIGS. 4N-4T also includes a pusher rod 312 and a tube end cap 124.

Figure 4R:
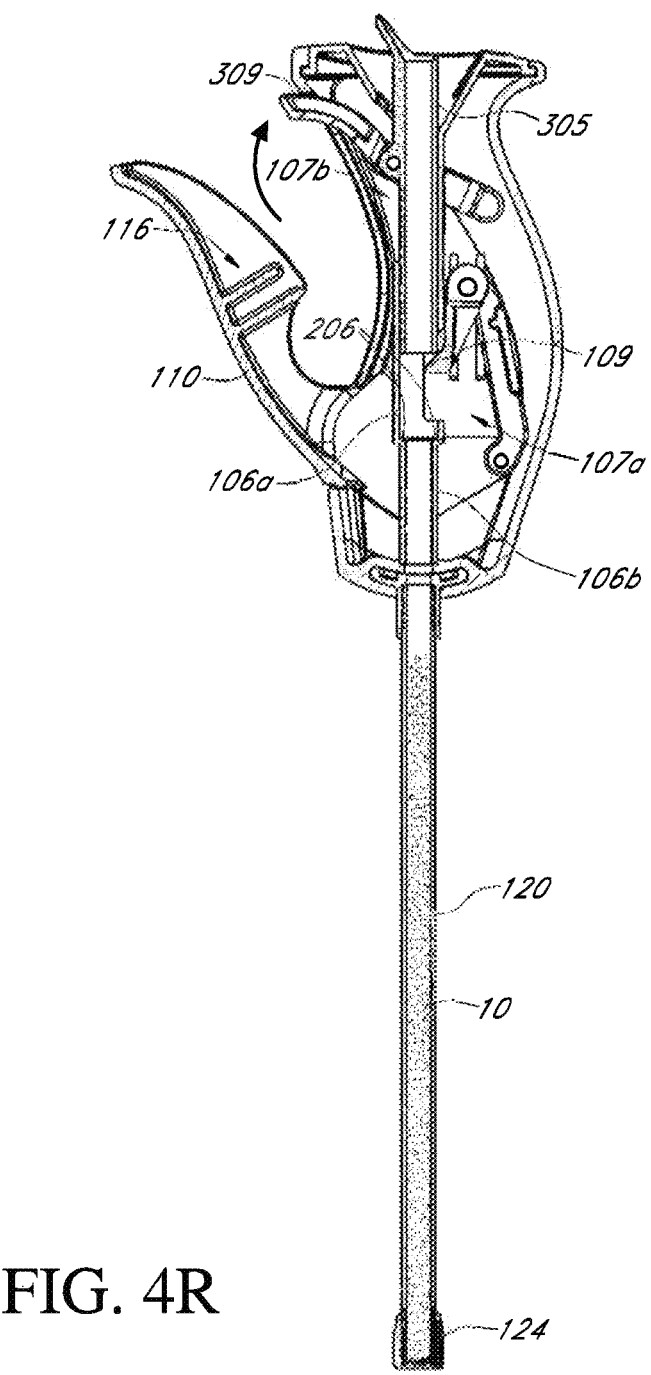
Figure 4S:
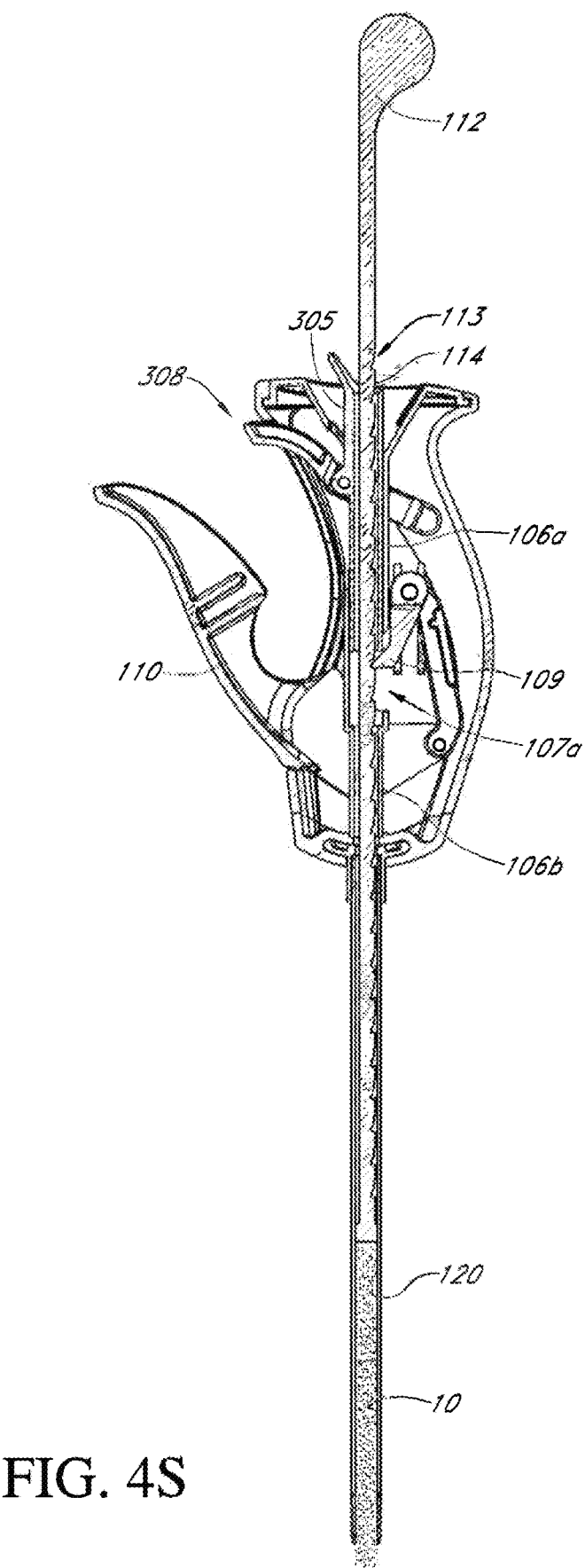
Figure 4T:
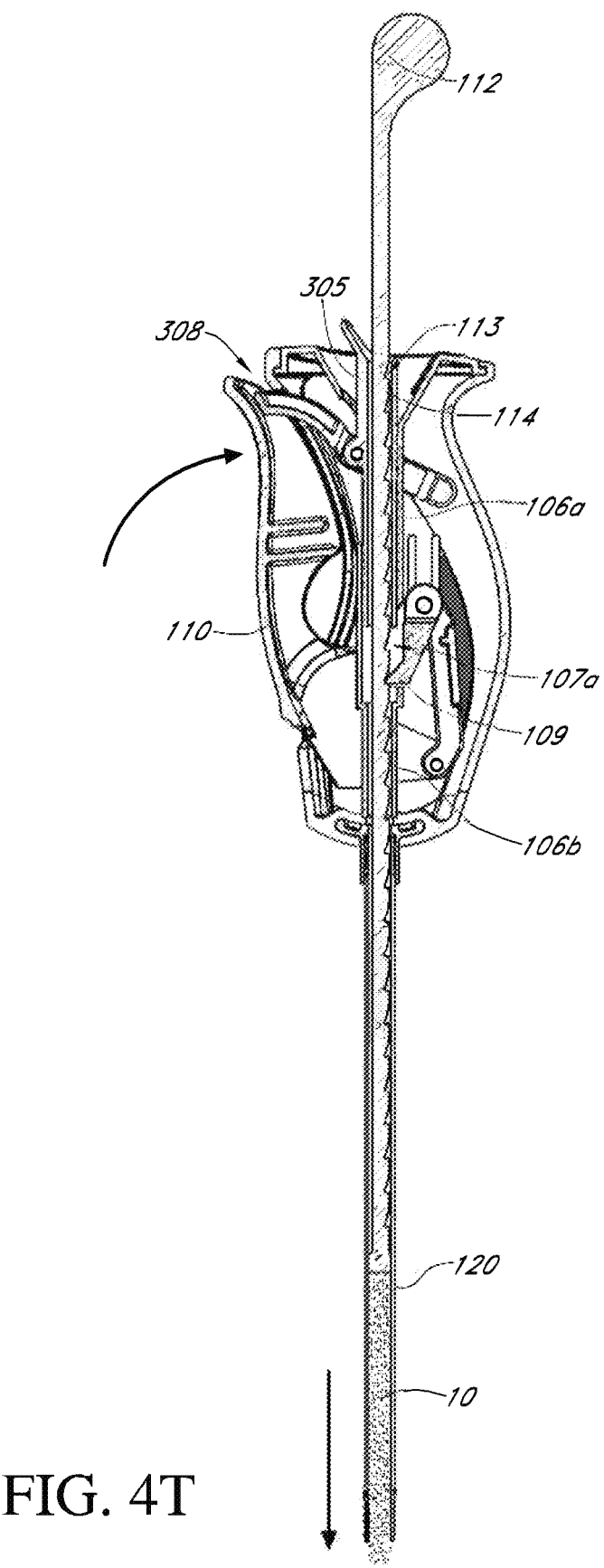
Figure 4U:
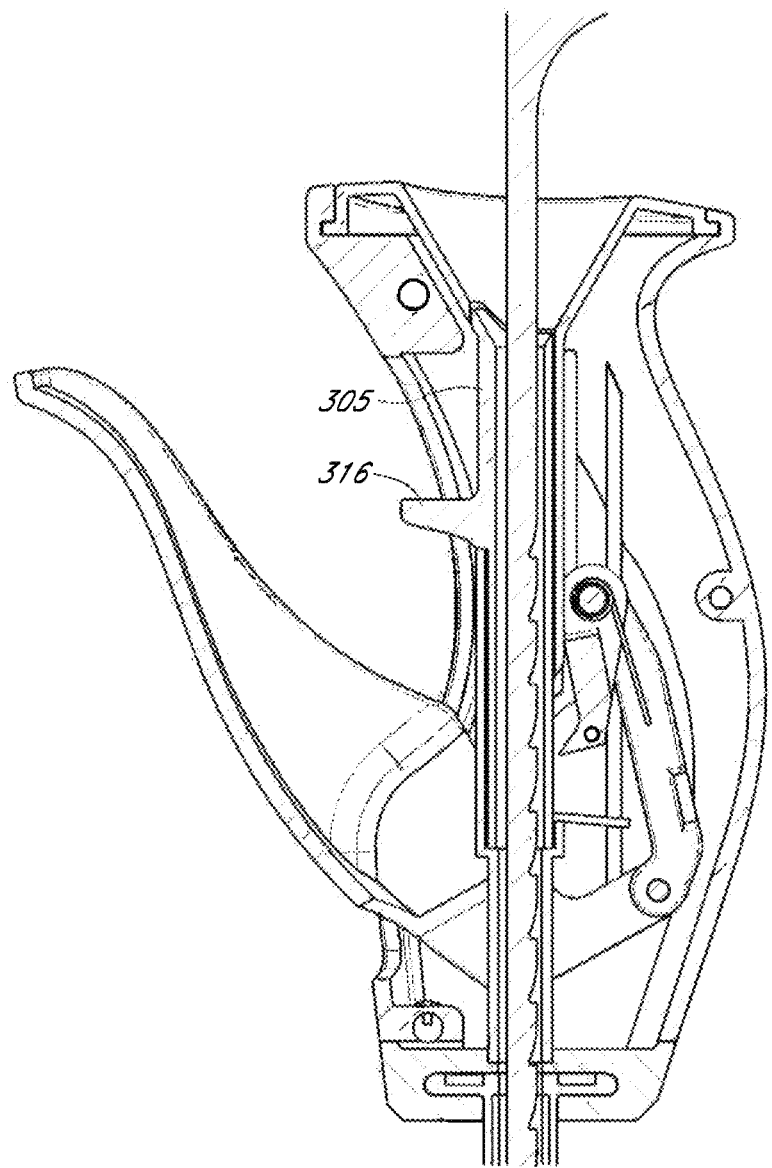
FIGS. 4U and 4V illustrate section views of an example embodiment of a handle of a bone graft delivery device including a ratcheting mechanism.
Figure 4V:
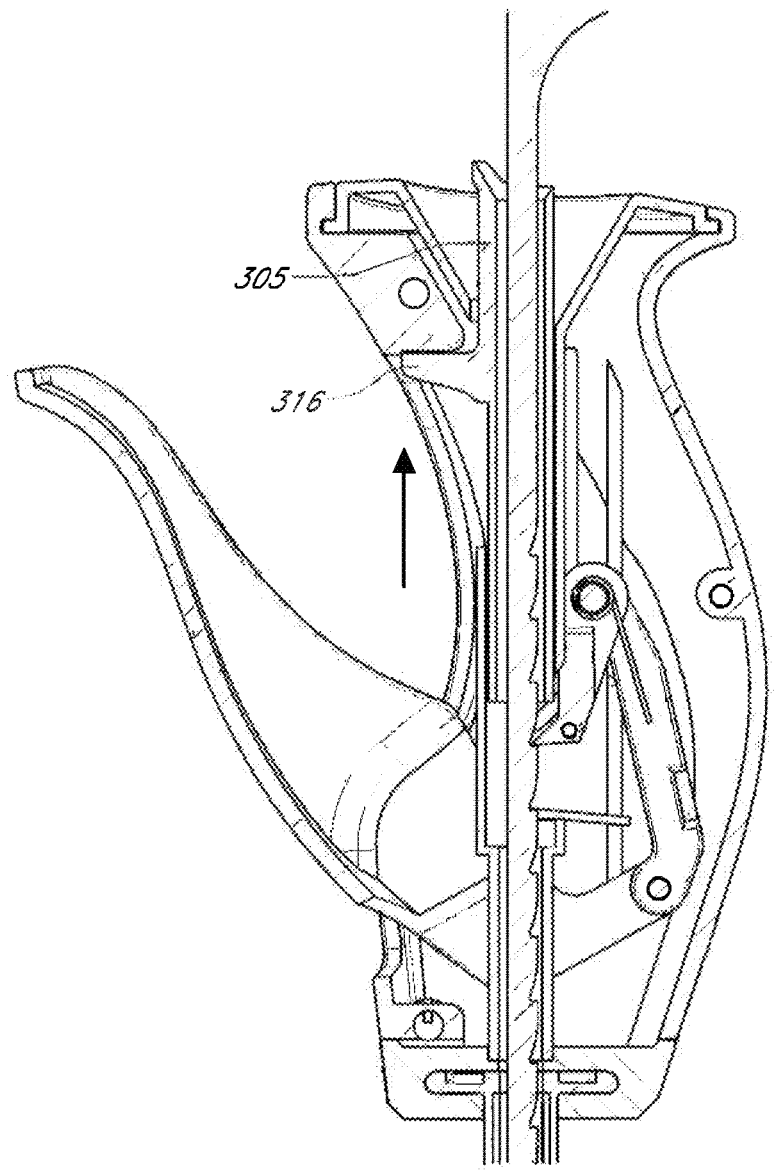

To load bone graft material, the lever 308 is coupled to the trigger 110 so that the sheath 305 sits in the initial loading position shown in FIG. 4P. Bone graft material 10 is loaded into the funnel 104, and the pusher rod 312 can be inserted into the funnel 104 to help urge the bone graft material 10 through the sheath 305 and lower shaft portion 106b and into the tube 120 as shown in FIG. 4Q. In some embodiments, the pusher rod 312 is made of, for example, a glass filled or rigid polymer material. The tube end cap 124 inhibits or prevents the bone graft material 10 from exiting the distal end of the tube 120 during the loading process and until the user wishes to deliver the bone graft material 10. The tube end cap 124 can be attached to the distal end of the tube 120 via a threaded coupling, friction fit, or other suitable means. In the illustrated embodiment, the tube 120 includes external threads 125b at or near the distal end configured to mate with internal threads in the tube end cap 124. Once the bone graft material 10 is loaded, the pusher rod 312 is removed, and the lever 308 is released from the trigger 110 as shown in FIG. 4R. As shown, release of the lever 308 causes or allows the lever to move toward the funnel, thereby also moving the sheath 305 proximally to expose the first window 107a and allow the pawl 109 to enter the shaft 106 through the first window 107a. The plunger 112 can be inserted before or after releasing the lever 308 and extends through the sheath 305, upper shaft portion 106a, and lower shaft portion 106b and into the tube 120 as shown in FIG. 4S. When the plunger 112 is inserted and the lever 308 is released so that the first window 107a is exposed, the pawl 109 engages one of the notches 113 on the plunger 112. The lever 308 can advantageously provide the user with a greater mechanical advantage and/or greater control in moving the sheath 305 proximally to expose the first window 107a. In other embodiments, the sheath includes a protrusion 316 without a lever as shown in FIGS. 4U and 4V. The user can use the protrusion 316 to lift or lower the sheath 305.

The tube end cap 124 is removed when the user wishes to deliver the bone graft material 10 through the tube 120. Movement of the trigger 110 toward the handle causes the pawl 109 to move distally, advancing the plunger 112 distally, as shown in FIG. 4T. The trigger 110 is moved away from and toward the handle to advance the plunger 112 and bone graft material 10 through the tube 120 in discreet increments. Of course, other ratcheting mechanisms and/or other mechanisms for advancing bone graft material through the handle 102 and/or tube 120 are also possible.

In some embodiments, the funnel 104 or other opening for loading of bone graft material can be positioned in the handle 102 in locations other than a proximal end or base of the handle 102. For example, in the example embodiment of FIGS. 2C-2E, the handle 102 is configured such that the trigger 110 and a grip 111 extend from a main body portion 103 of the handle 102. As shown, the funnel 104 is located on an opposite side of the body portion 103 from the grip 111 and trigger 110. A main channel 406 extends through the handle 102 from an opening in a proximal end of the body portion 103 to an opening in a distal end of the body portion 103 and is in fluid communication with the tube 120. The funnel shaft 106 extends from the funnel 104 to intersect the main channel 406 as shown in FIGS. 2D and 2E. In the illustrated embodiment, the funnel 104 and funnel shaft 106 are oriented at an angle 1 relative to the main channel 406. The angle can advantageously help direct bone graft material inserted into the funnel 104 and funnel shaft 106 distally toward the tube 120. The bone graft delivery device can include a pusher rod 312 as shown in FIG. 2E to help urge bone graft material from the funnel 104 through the funnel shaft 106 and into the main channel 406. In some embodiments, the pusher rod 312 can be configured such that when fully inserted into the funnel 104 and funnel shaft 106, a distal end 314 of the pusher rod 312 rests at the intersection of the funnel shaft 106 with the main channel 406 to at least partially or substantially close the main channel 406. The distal end 314 of the pusher rod 312 can be formed at an angle with the angle corresponding to the angle of the funnel shaft 106 so that the distal end 314 is continuous with a wall of the main channel 406 when inserted into the funnel shaft 106. In such embodiments, the pusher rod 312 can be configured to remain in place during delivery of bone graft material.

Figure 2C:
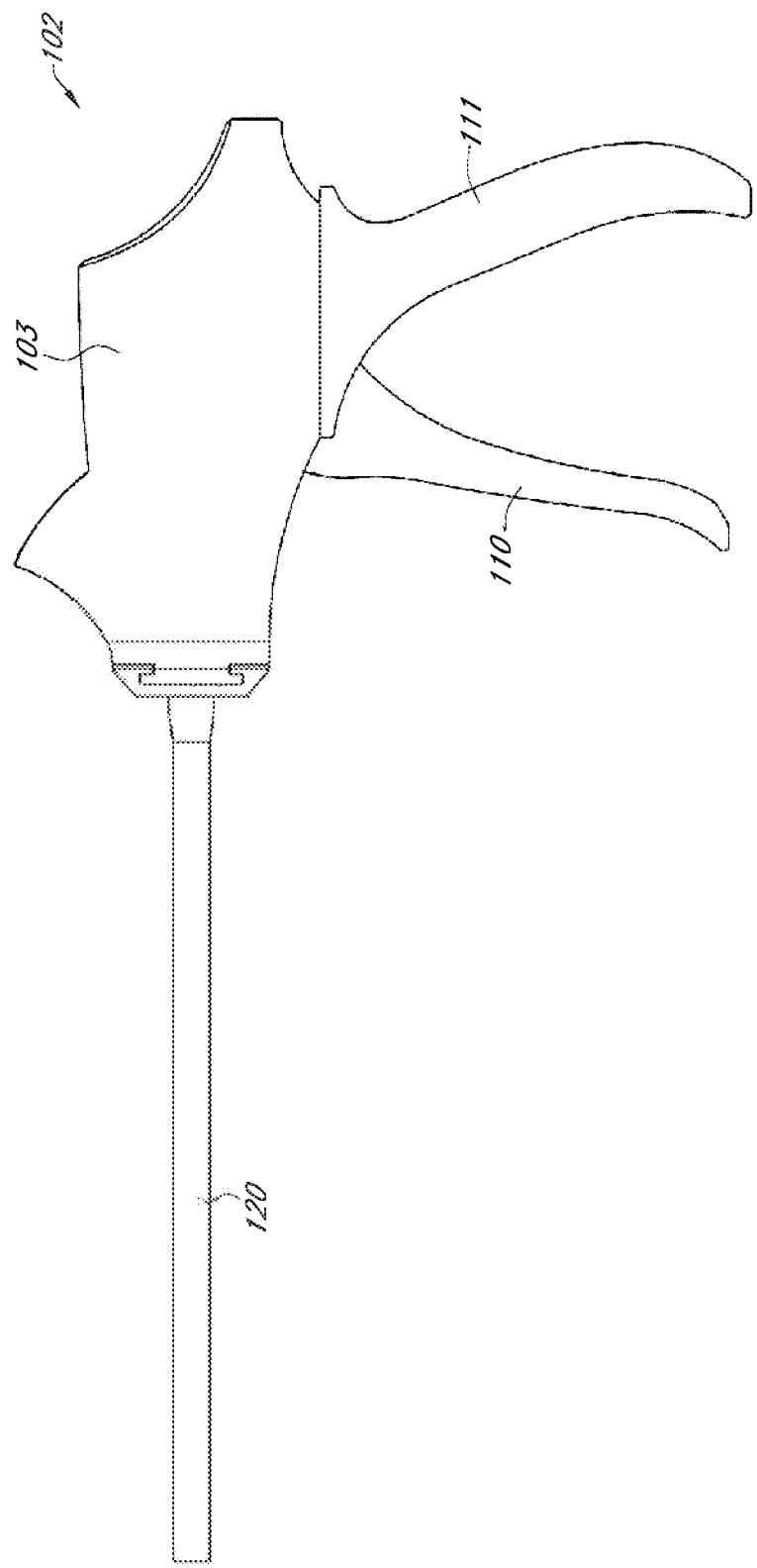
FIG. 2C illustrates a side view of another example embodiment of a bone graft delivery device.
Figure 2D:
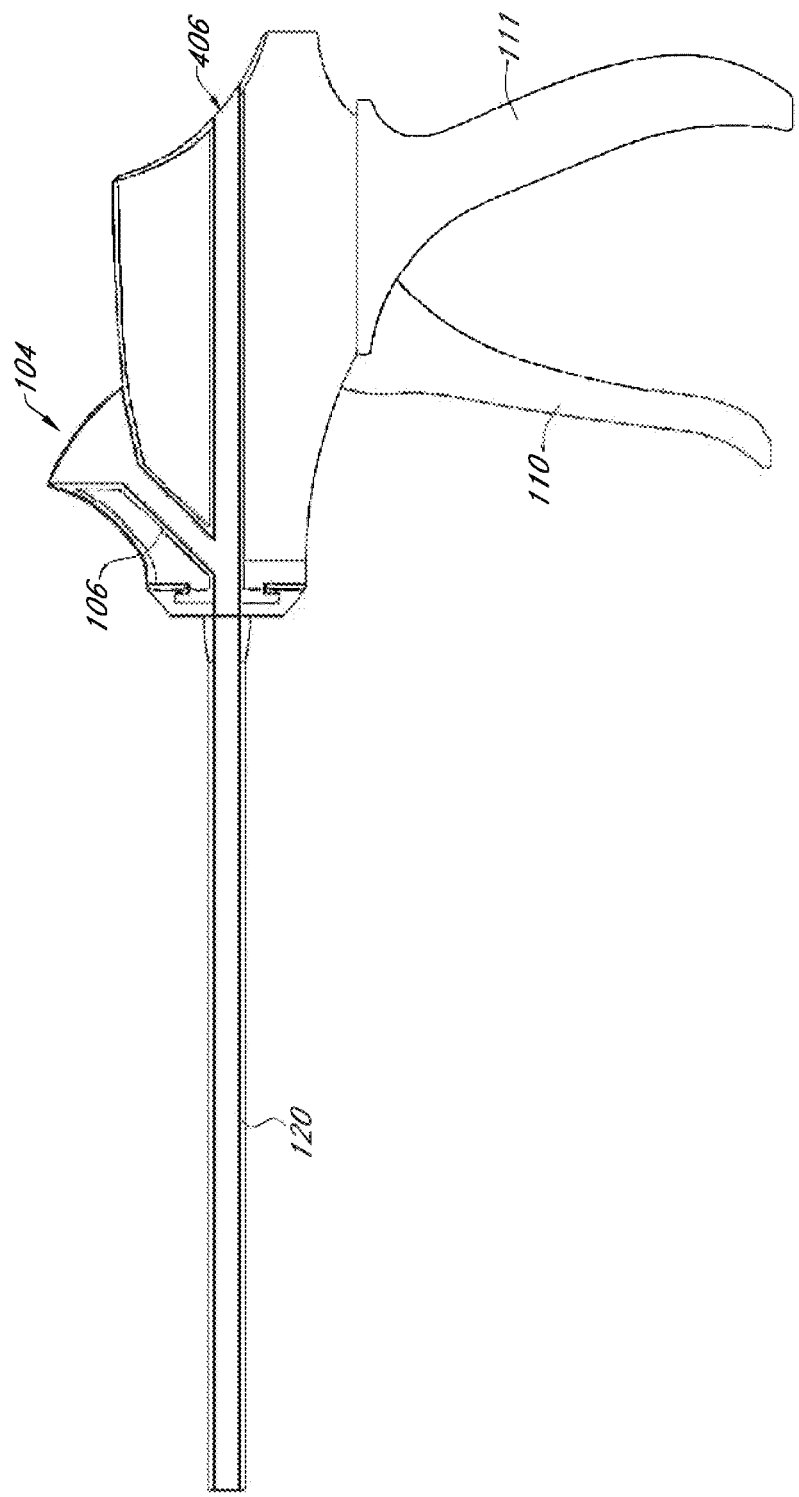
FIG. 2D illustrates a section view of the bone graft delivery device of FIG. 2C.
Figure 2E:
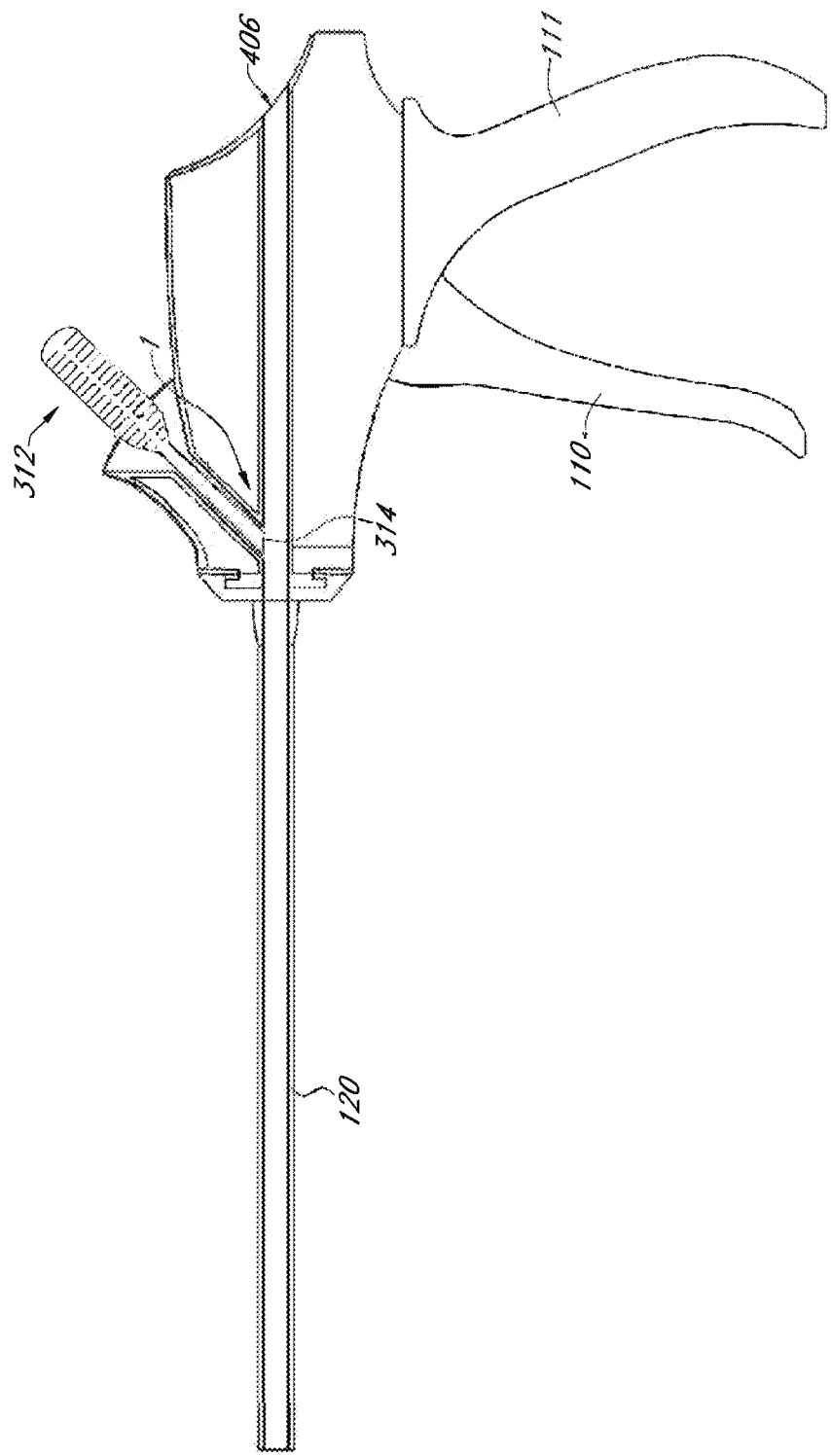
FIG. 2E illustrates a section view of the bone graft delivery device of FIGS. 2C and 2D including a pusher rod.

The handle 102 of FIGS. 2C-2E can include any of the ratcheting mechanisms described herein or any other suitable ratcheting mechanism. In use, once the bone graft material is loaded via the funnel 104, the plunger 112 is inserted from the proximal opening of the main channel 406 through the handle 102 and into the tube 120. The main channel 406 can include a window to allow the pawl to engage notches on the plunger. In use, movement of the trigger 110 toward the grip 111 can cause the pawl to advance the plunger and bone graft material distally in the tube 120. Releasing the trigger 110 to allow the trigger 110 to move away from the grip 111 causes the pawl to slide proximally along the plunger to engage a more proximal notch. If the window is located proximal to the intersection of the funnel shaft 106 with the main channel 406, the cover, sheath, or the like can be omitted from the ratcheting mechanism. In such embodiments, the bone graft material does not pass through the portion of the main channel 406 having the window, so the window can be left uncovered during loading. In some embodiments, the handle 102 of FIGS. 2C-2E does not include a ratcheting mechanism, and a plunger can be inserted into and advanced through the main channel 406 and tube 120 to advance and deliver the bone graft material.

Figure 2F:
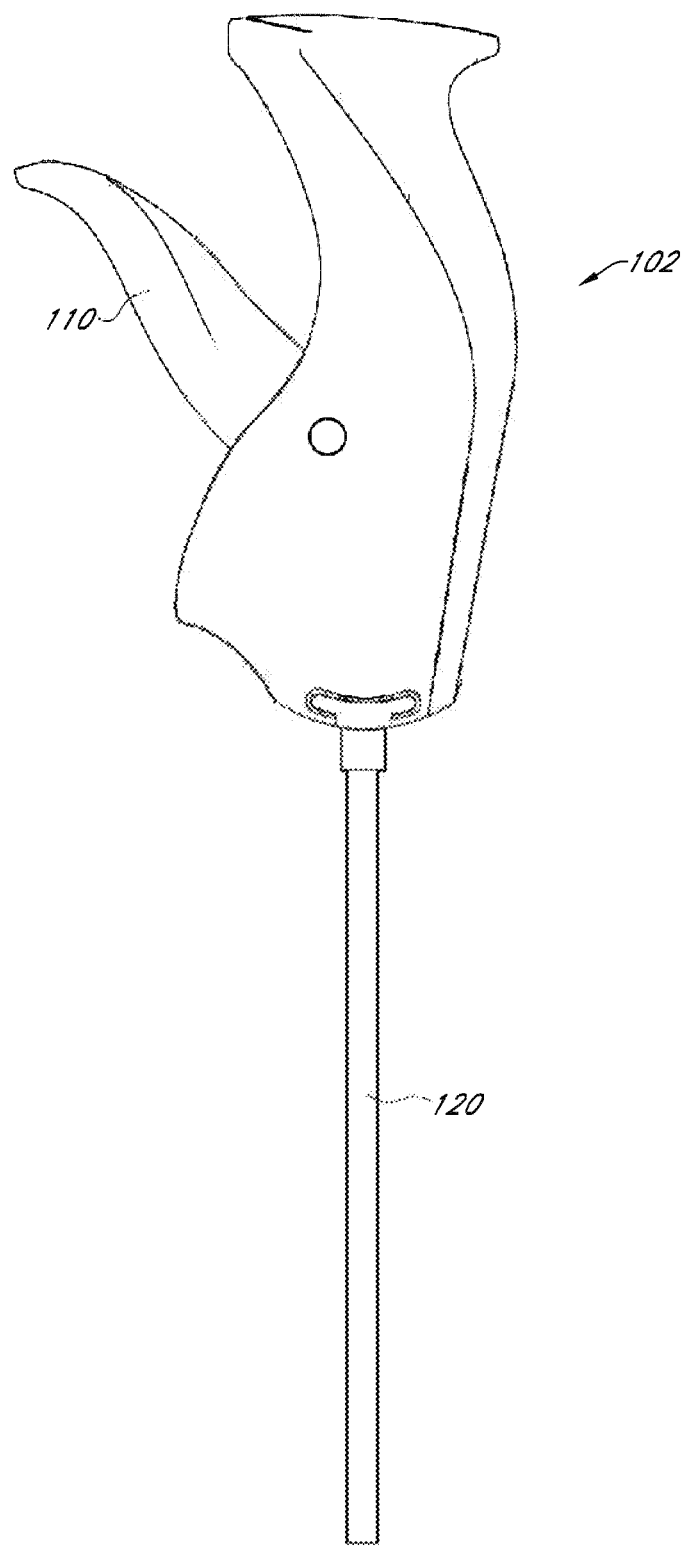
FIG. 2F illustrates a side view of another example embodiment of a bone graft delivery device.
Figure 2G:
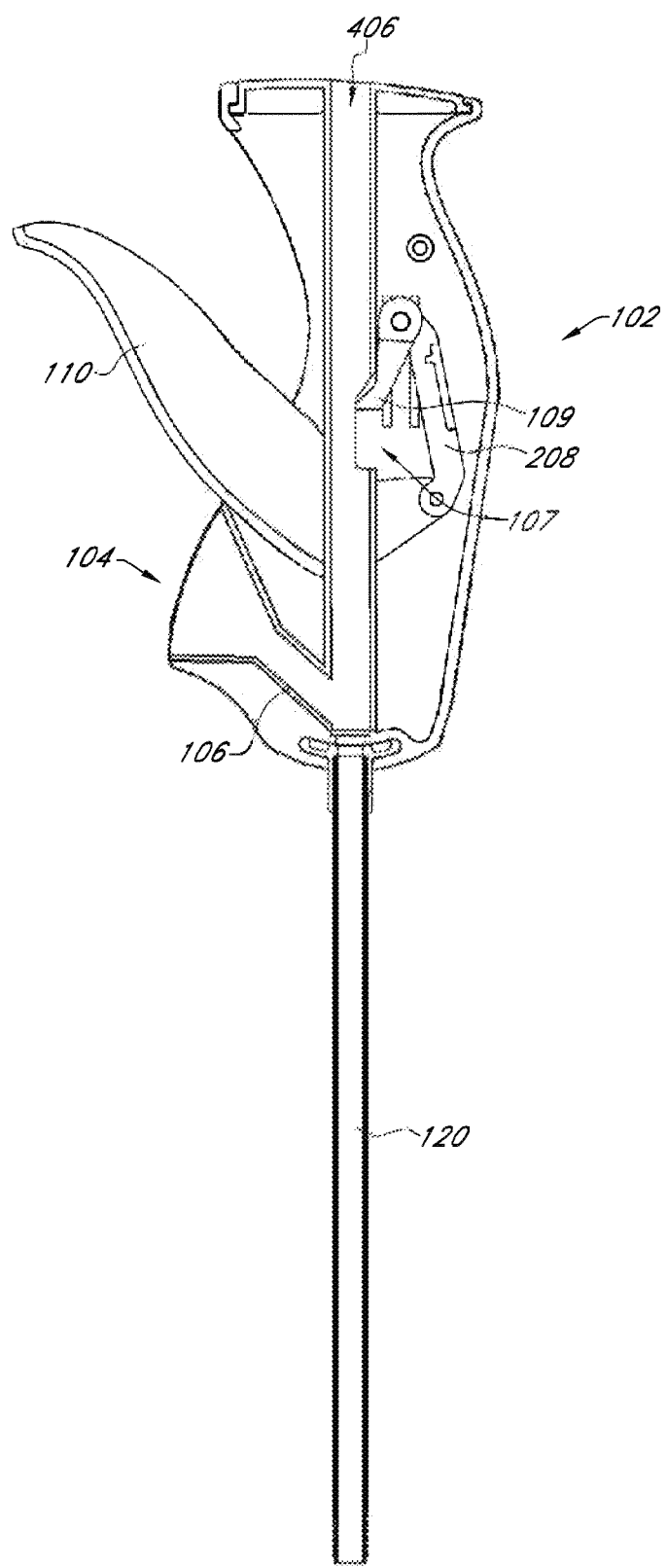
FIG. 2G illustrates a section view of the bone graft delivery device of FIG. 2F.
Figure 2H:
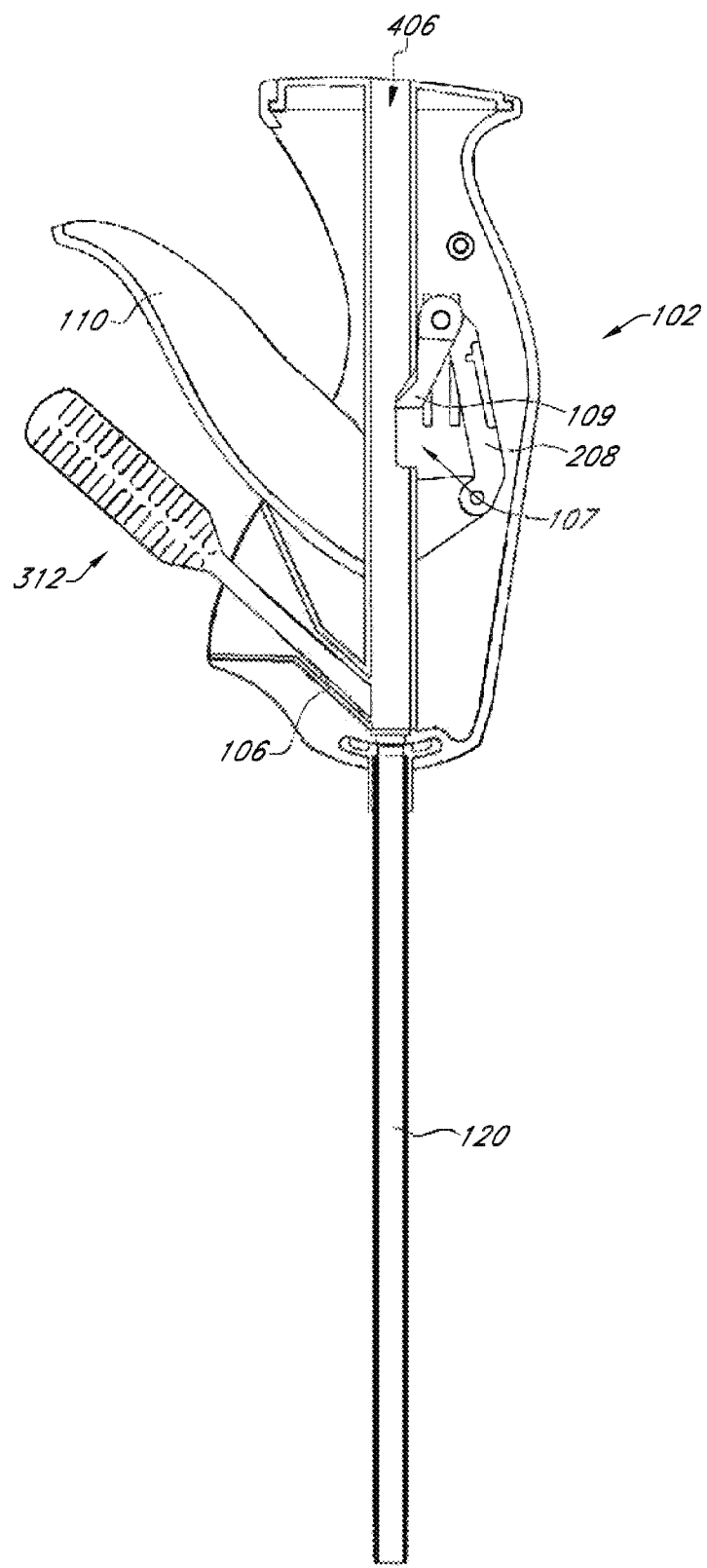
FIG. 2H illustrates a section view of the bone graft delivery device of FIGS. 2F and 2G including a pusher rod.
Figure 2I:
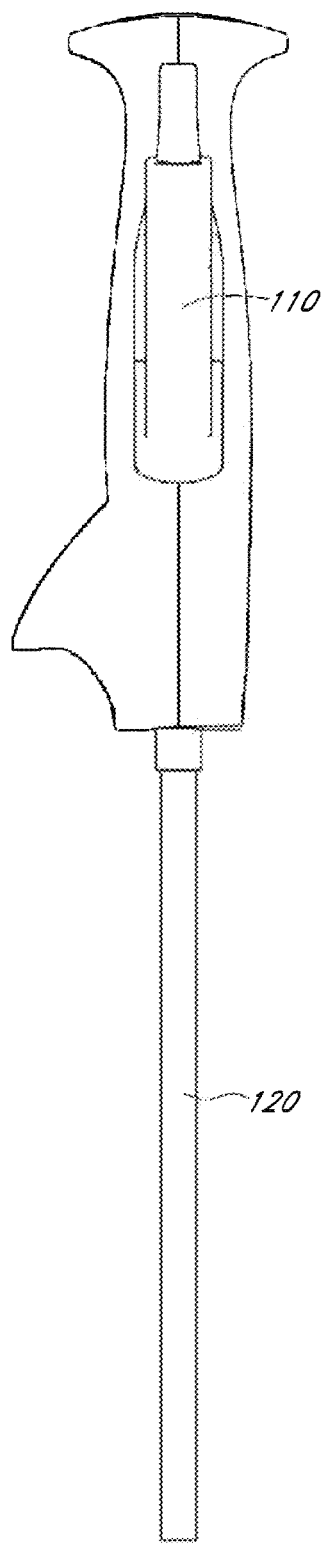
FIG. 2I illustrates a bottom view of another example embodiment of a bone graft delivery device.
Figure 2J:
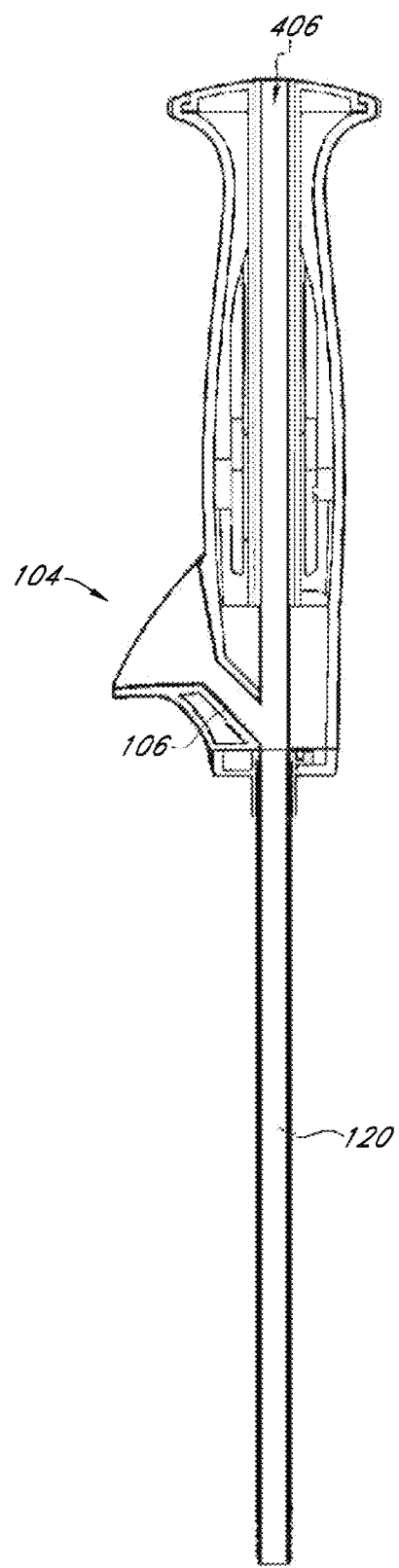
FIG. 2J illustrates a section view of the bone graft delivery device of FIG. 2I.
Figure 2K:
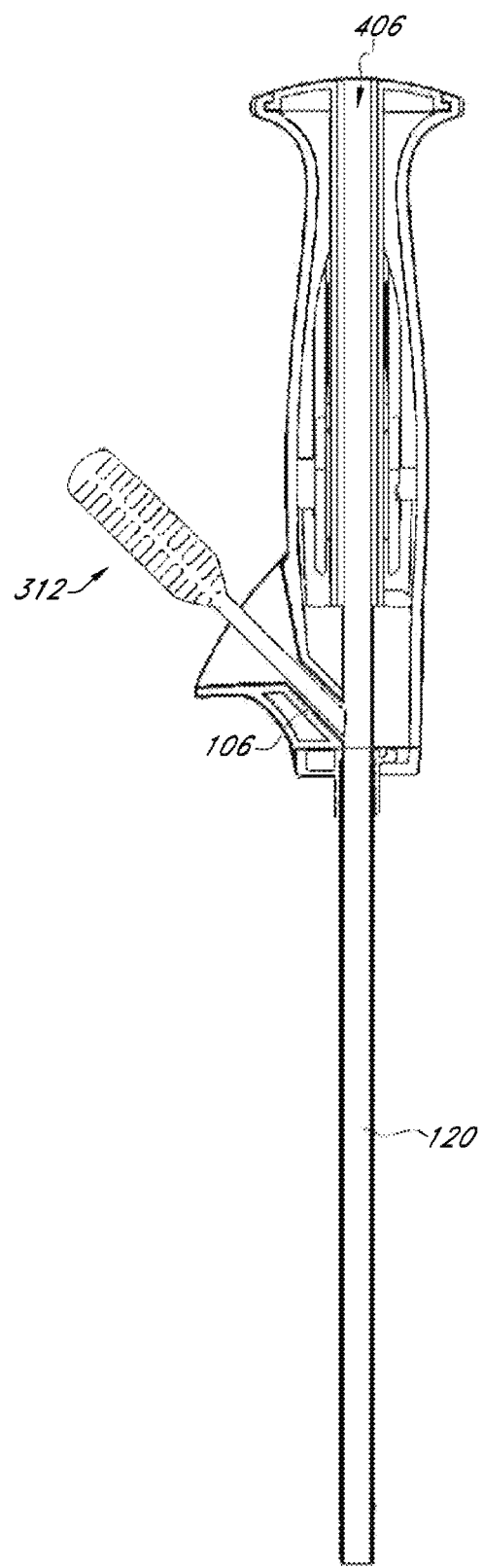
FIG. 2K illustrates a section view of the bone graft delivery device of FIGS. 2I and 2J including a pusher rod.

FIGS. 2F-2H illustrate an alternative embodiment in which the funnel 104 is located on the same side or surface of the handle 102 as the trigger 110. In the illustrated embodiment, the funnel 104 is advantageously located distal to the trigger 110 so that the pusher rod 312, when inserted into the funnel 104, does not interfere with operation of the trigger 110. The embodiment of FIGS. 2F-2H can also include a main channel 406, an angled funnel 104, funnel shaft 106, and distal end 314 of the pusher rod 312, and any suitable ratcheting mechanism similar to the embodiment shown in FIGS. 2C-2E and discussed above. In use, a plunger is inserted into the main channel 406 and tube 120. In the illustrated embodiment, the main channel 406 includes a window 107 to allow the pawl 109 to engage notches on the plunger when the plunger is inserted. Movement of the trigger 110 towards the handle 102 causes the pawl 109 to move distally within the window 107, thereby advancing the plunger and bone graft material. Movement of the trigger 110 away from the handle causes the pawl 109 to slide proximally along the plunger and engage a more proximal notch. In the illustrated embodiment, the window 107 and ratcheting mechanism are located proximal to the intersection of the funnel shaft 106 with the main channel 406, and the ratcheting mechanism does not include a cover or sheath. FIGS. 2I-2K illustrate another alternative embodiment, similar to the embodiment of FIGS. 2F-2H, with the funnel 104 positioned on a side or surface of the handle 102 lateral or generally perpendicular to the trigger 110. In other embodiments, the funnel 104 can be located on any side or surface of the handle 102, for example, opposite the trigger 110, to either side of the trigger, or any other position around the handle 102. The funnel 104 can also be located distal to, even with, or proximal to the trigger 110.

FIGS. 16A-16D illustrate another alternative embodiment of a bone graft delivery device 100 having a handle 102 including a ratcheting mechanism 508. In use, the ratcheting mechanism 508 is used to advance the plunger 112 and bone graft material through the tube 120 for delivery. As shown, the ratcheting mechanism 508 includes a pawl 509 having one or more teeth 514 that are received in the notches 113 of the plunger 112. In the illustrated embodiment, the pawl 509 includes four teeth 514, although more or fewer teeth 514 are also possible. A pawl 509 having multiple teeth 514 can engage multiple notches 113 of the plunger 112 simultaneously, which can advantageously provide a more secure engagement between the ratcheting mechanism 508 and the plunger 112, allow the pawl 509 to apply a greater advancement force on the plunger 112, and/or compensate for possible malfunctioning or manufacturing variances or defects to better ensure at least one tooth 514 engages the plunger 112.

The pawl 509 can be coupled to the trigger 110 via a pivot point 515 and/or a spring 517. The spring 517 can advantageously provide resistance to movement of the trigger 110 relative to the body of the handle 102. In some embodiments, the spring 517 can bias the trigger 110 away from the body of the handle 102 (toward the position shown in FIGS. 16A-16B).

In some embodiments, the handle 102 and tube 120 have a modular construction such that the tube 120 is removably coupleable to the handle 102 as described herein. The tube 120 can be provided preloaded with bone graft or can be loaded with bone graft prior to being coupled to the handle 102 as described in greater detail herein. In some embodiments, a handle 102, for example, a handle 102 including any of the ratcheting mechanisms described herein or another suitable ratcheting or advancement mechanism, need not include a funnel and/or a channel or funnel shaft. In use, a tube 120 loaded with bone graft is coupled to the handle 102, the plunger 112 is inserted through the handle 102 into the tube 120, and the ratcheting mechanism 508 is used to advance the plunger 112 and bone graft material through the tube 120 for delivery.

Figure 16A:
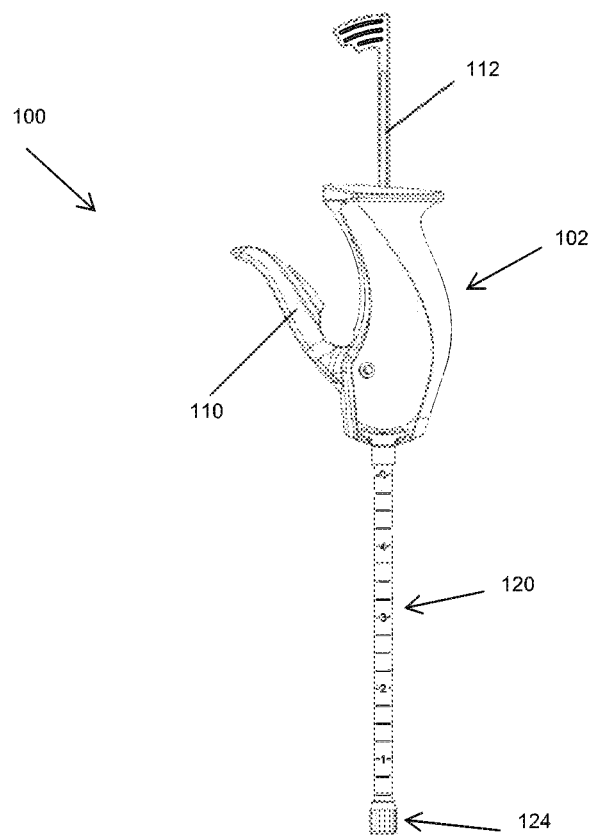
FIG. 16A illustrates a side view of an example embodiment of a bone graft delivery device having a handle including a trigger and a ratcheting mechanism with the trigger in a first position.
Figure 16B:
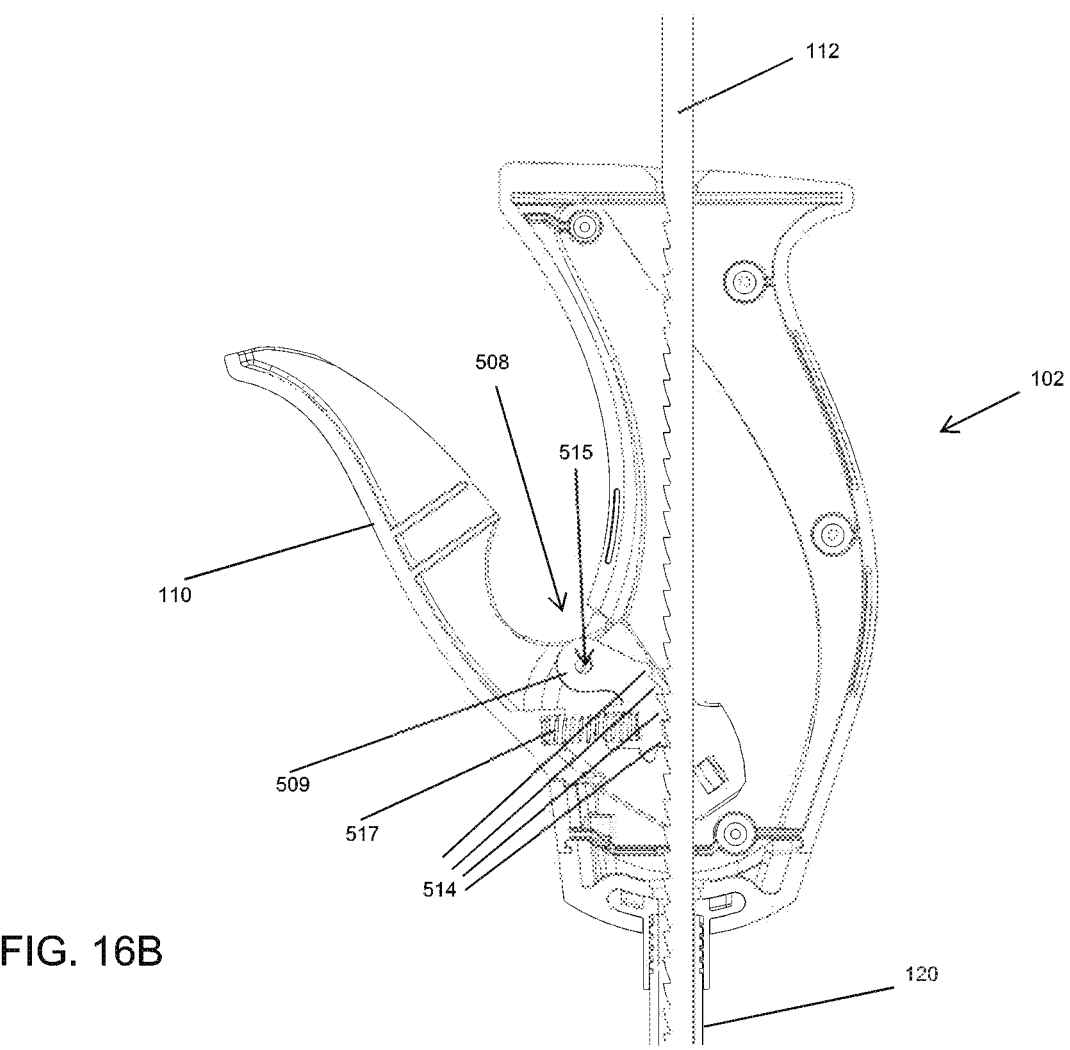
FIG. 16B illustrates a section view of the bone graft delivery device of FIG. 16A.
Figure 16C:
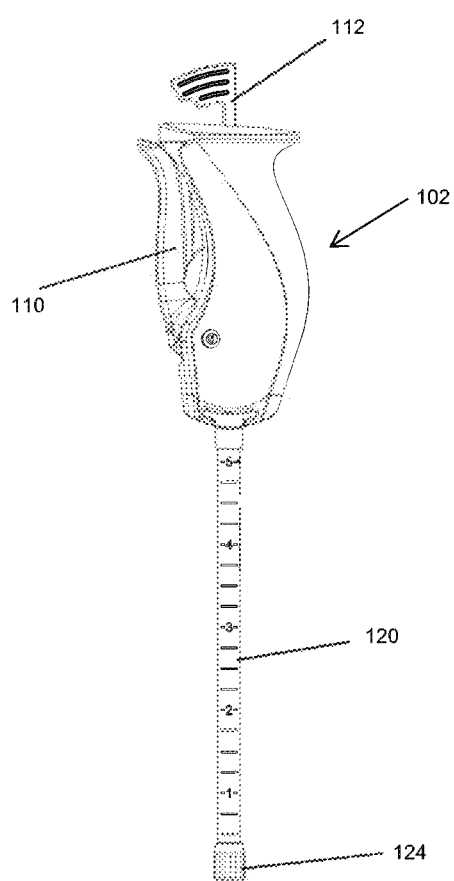
FIG. 16C illustrates a side view of the bone graft delivery device of FIG. 16A with the trigger in a second position.
Figure 16D:
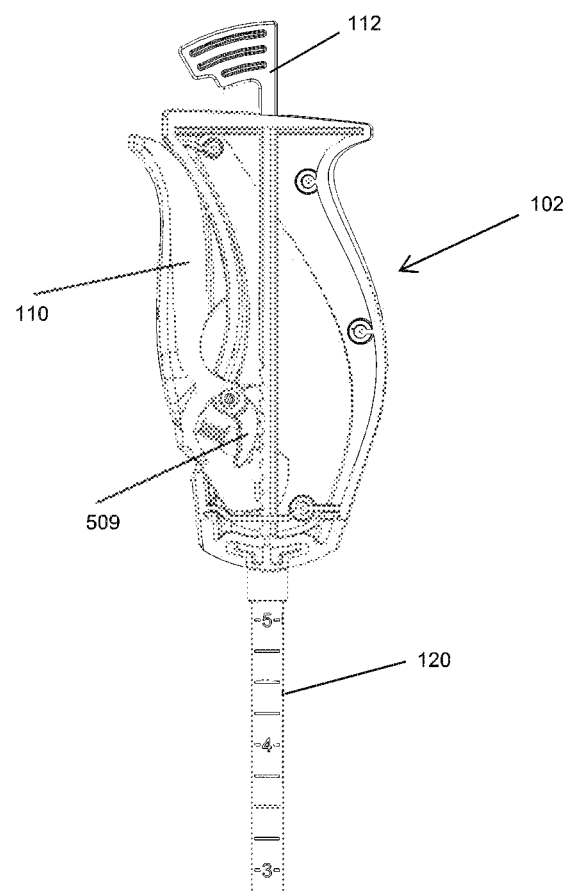
FIG. 16D illustrates a section view of the bone graft delivery device of FIG. 16C.

In use, movement of the trigger 110 from the position shown in FIGS. 16A-16B to the position closest to the handle 102 body shown in FIGS. 16C-16D causes the teeth 514 of the pawl 509 to move distally (toward the tube 120) within the handle 102, thereby advancing the plunger 112 distally within the tube 120 to force the bone graft material distally within the tube 120. Movement of the trigger 110 back to the position shown in FIGS. 16A-16B causes the teeth 514 of the pawl 509 to side proximally along the plunger 112 and over the teeth 114 to engage more proximal notches 113.

In some embodiments, the plunger 112 teeth 114 can be spaced relatively closer together (for example, as shown in FIGS. 16A-16B compared to FIG. 4I). Such closer spacing can allow the ratcheting mechanism 108, 508 to be more reliable such that in the event that the pawl 509 misses a notch 113, the pawl 509 can engage the next notch 113 more quickly, easily, and/or with less backlash. The closer spacing can also allow the user to squeeze the trigger 110 toward the handle 102 body to a lesser extent (for example, only halfway or to another intermediate point) to deliver a smaller amount of bone graft material at a particular time if desired. If the distance between the teeth 114 is less than the displacement of the plunger 112 with a full stroke of the trigger 110 and ratcheting mechanism 108, 508, the pawl 109, 509 can engage a more proximal notch 113 as long as the trigger 110 is moved toward the handle 102 body enough that the plunger 112 is displaced by a distance greater than the distance between adjacent notches 113.

As shown in FIGS. 1A and 1B, the tube 120 of any of the devices described herein can include a permanent bend or curve that may be useful in positioning the device 100 at a desired location, for example, a space between two spinal discs, transverse process, facet joint, lamina, or other target area. Alternatively, the tube 120 may be straight, for example, as shown in FIGS. 2A and 2B, to deliver bone graft material directly into a desired location such as a disc space, transverse process, facet joint, lamina, or other target area. In some embodiments, the tube 120 is somewhat flexible or repositionable and can be manipulated to bend or curve the tube 120 as needed to reach the desired location. In some embodiments, the tube 120 is made of a rigid material, for example, a plastic, composite, or metal. In some embodiments, the tube 120 can be at least partially transparent, which can allow the user to view, for example, the volume or position of the graft material within the tube 120. The tube 120 can also include volume markings to allow the user to monitor the amount of graft material delivered to the target site and remaining in the tube 120, for example, as shown in FIGS. 4N-4O. In some embodiments, the tube 120 includes one or more radiopaque markers to allow for visualization on, for example, x-ray or fluoroscopy. The tube 120 is generally hollow to allow for the passage of bone graft material through the lumen of the tube 120. The tube 120 and lumen can have various diameters, for example, for different applications and/or target locations.

Figure 5A:
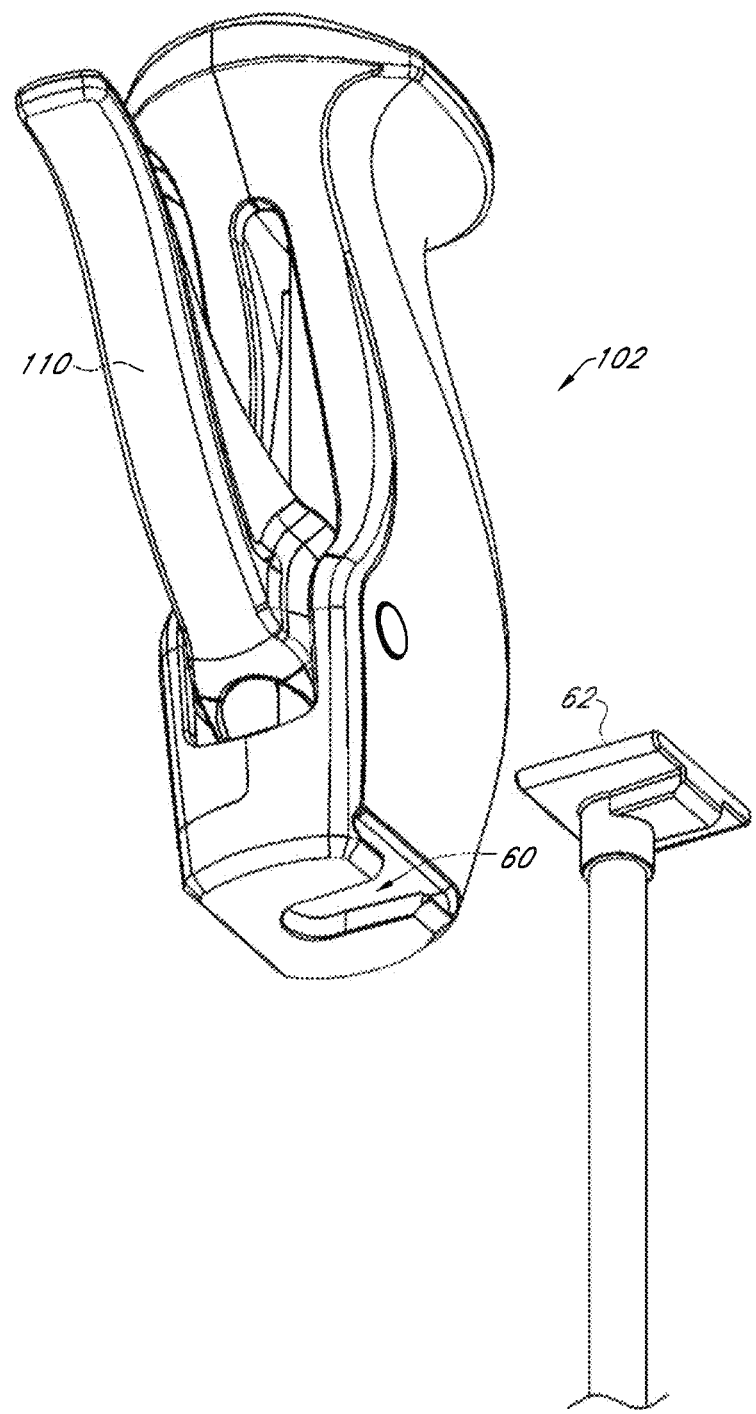
FIGS. 5A and 5B illustrate an example embodiment of a bone graft delivery device having a modular handle and tube construction.
Figure 5B:
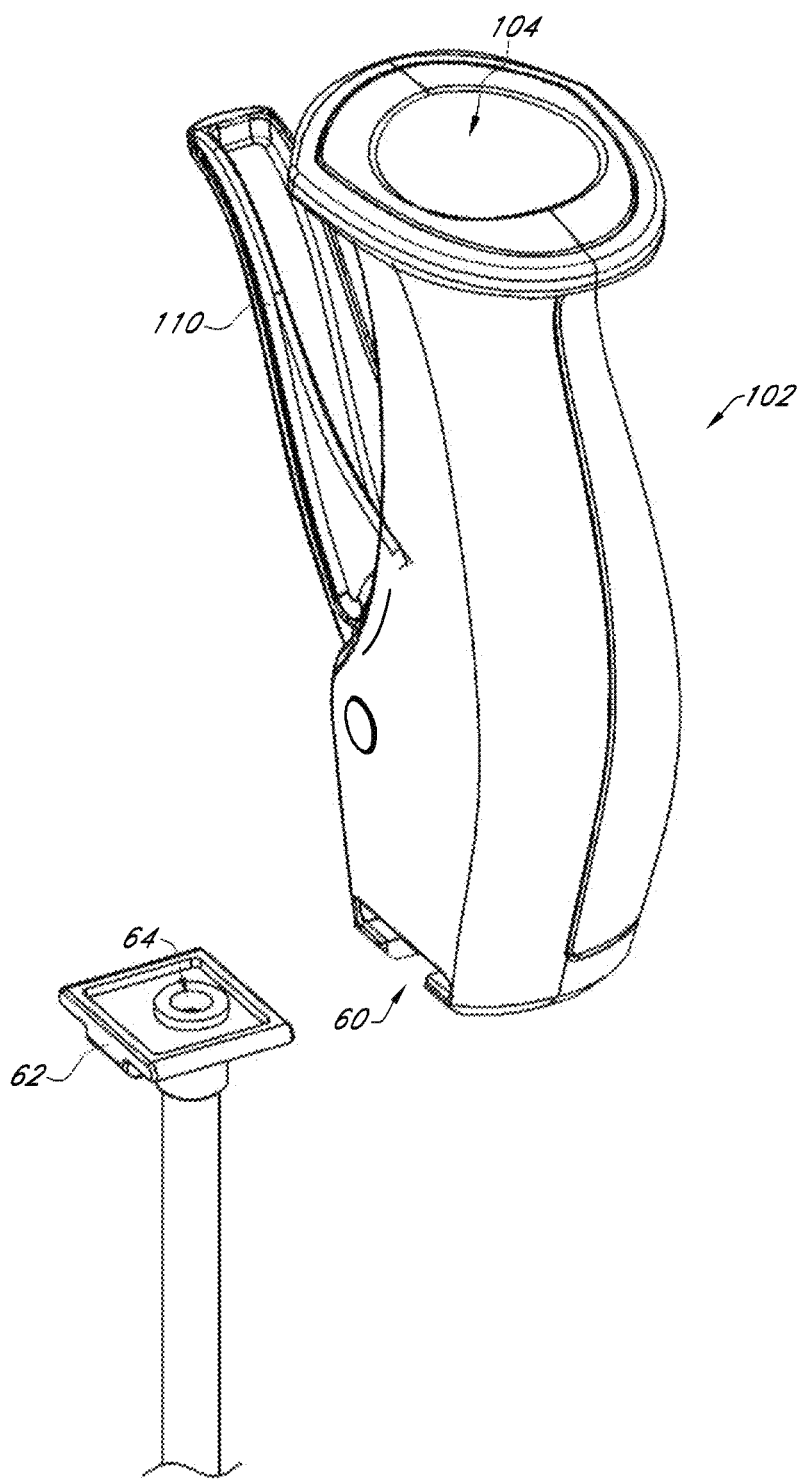

In some embodiments, the tube 120 can be integrally formed with or permanently coupled to the handle 102. In other embodiments, the bone graft delivery device 100 can have a modular construction so that various tubes 120 can be selected and coupled to the handle 102. Such a modular construction can advantageously allow the user to interchange straight and curved handles and/or handles having various other features depending on the target location, particular patient, and/or other factors. As shown in FIGS. 5A and 5B, the distal end of the handle 102 or any of the handles described herein can include a recess 60 configured to receive a base 62 coupled to or integrally formed with the tube 120. The base 62 can be coupled to the tube 120 via a threaded coupling, press fit, or any other suitable means. For example, in the embodiment shown in FIGS. 4N-4T, the tube 120 includes external threads 125a at or near a proximal end of the tube configured to mate with internal threads in the base 62. As shown in FIG. 5B, the base 62 can include an aperture to allow fluid communication between the funnel shaft 106 in the handle 102 and the tube 120. The tube 120 can also be coupled to the handle 102 by any other appropriate means.

Figure 6A:
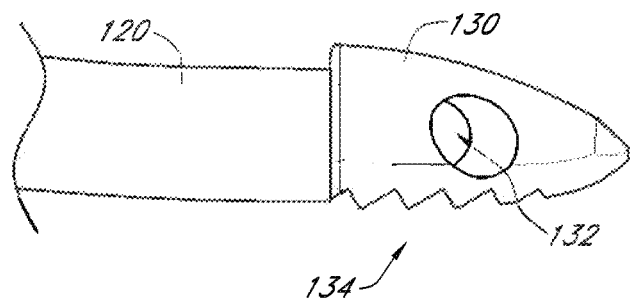
FIGS. 6A-6C illustrate various views of a distal tip of the bone graft delivery device of FIGS. 1A and 1B.
Figure 6B:
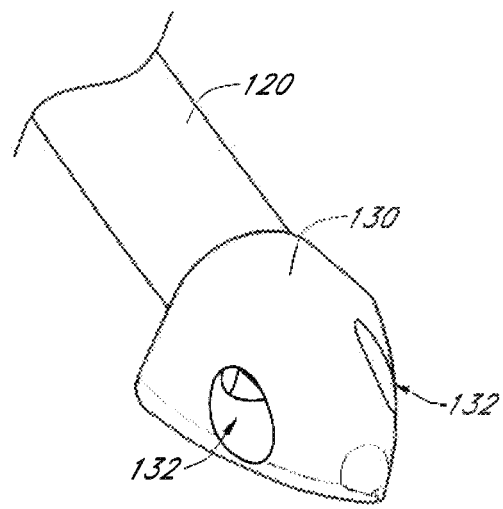
Figure 6C:
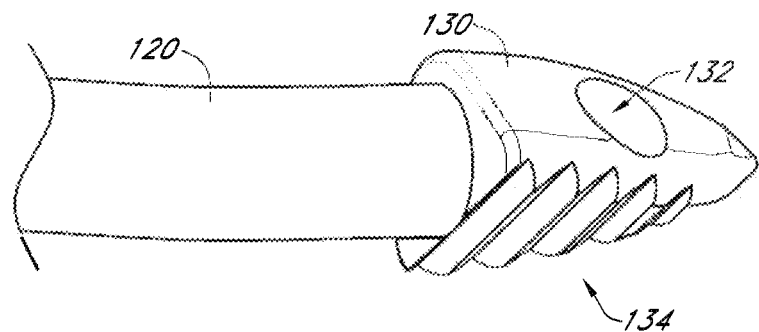
Figure 6D:
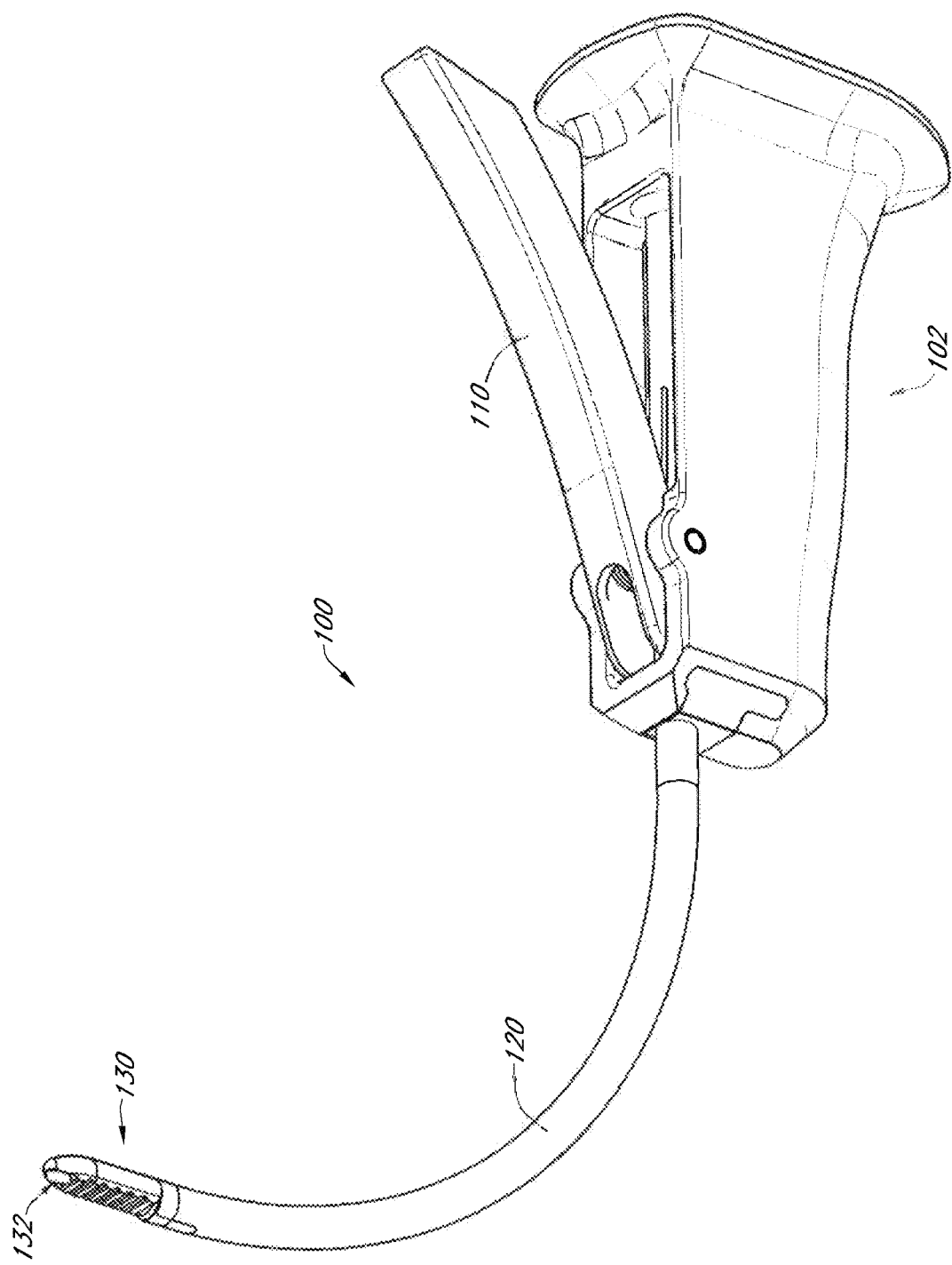
FIG. 6D illustrates a perspective view of an example embodiment of a bone graft delivery device having a curved tube.
Figure 6E:
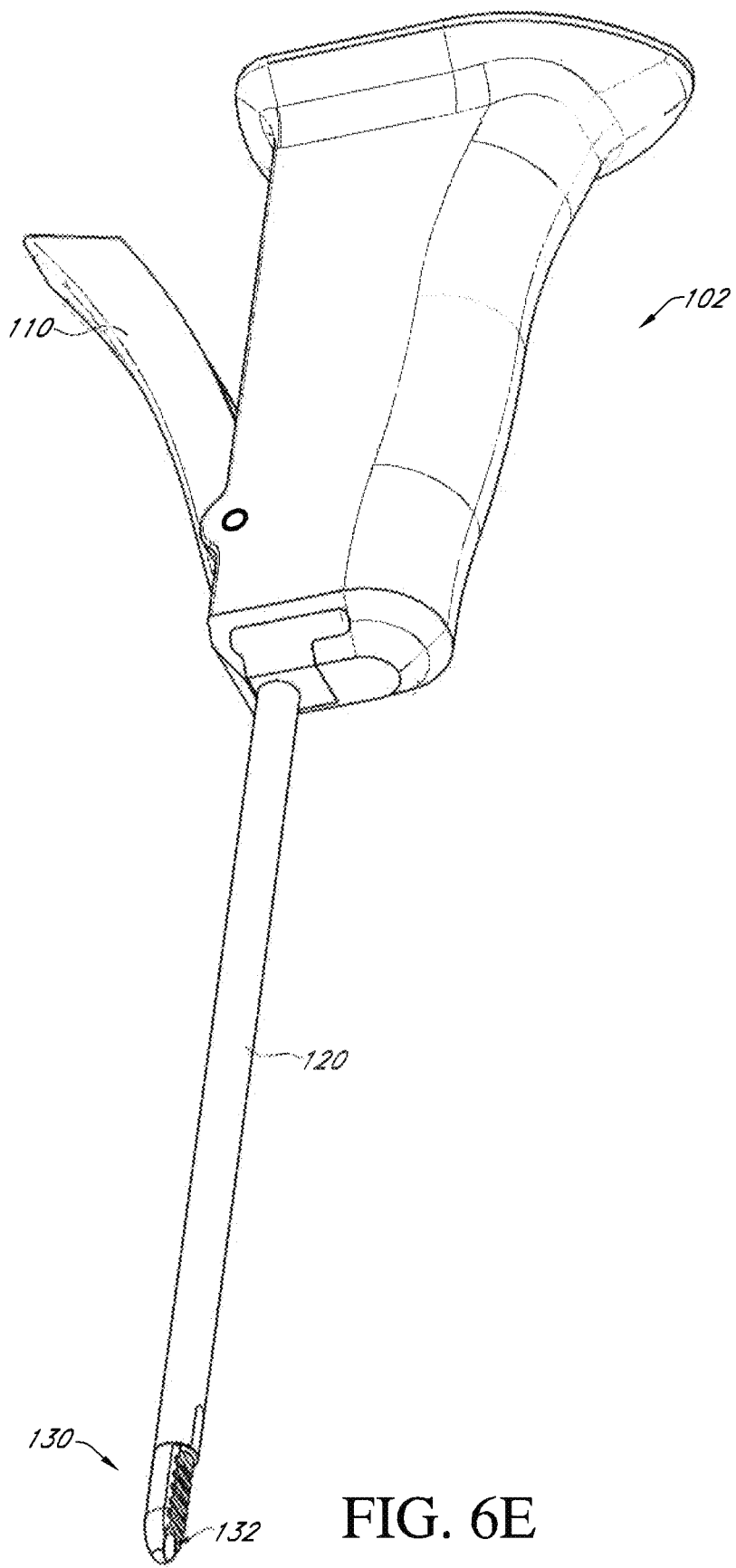
FIG. 6E illustrates a perspective view of an example embodiment of a bone graft delivery device having a straight tube.
Figure 6F:
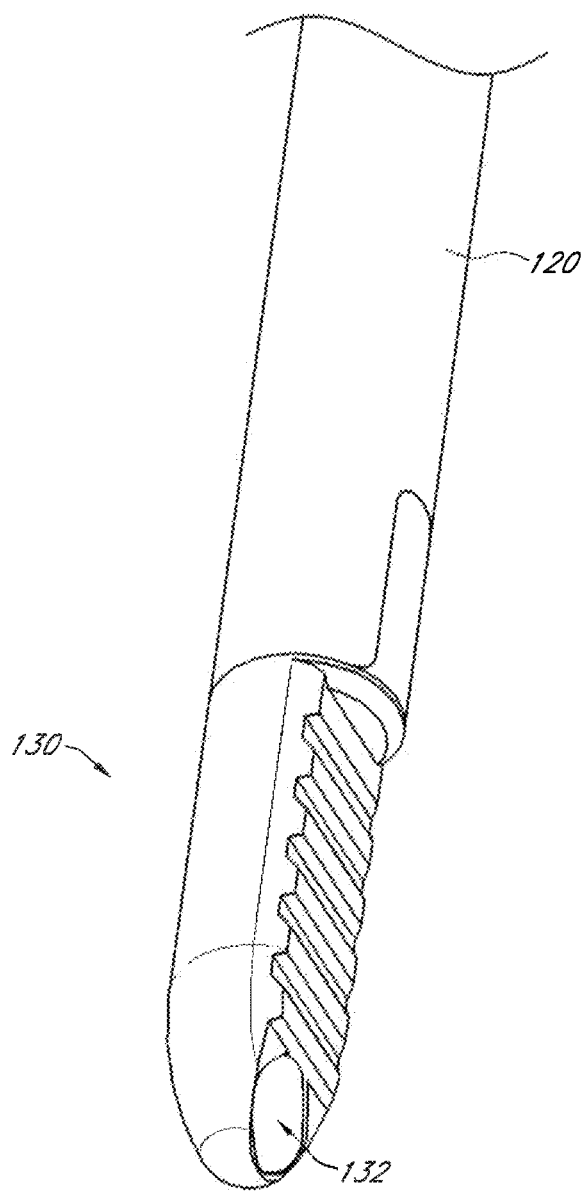
FIG. 6F illustrates an enlarged view of a rasping distal tip of the bone graft delivery device of FIG. 6E.
Figure 6G:
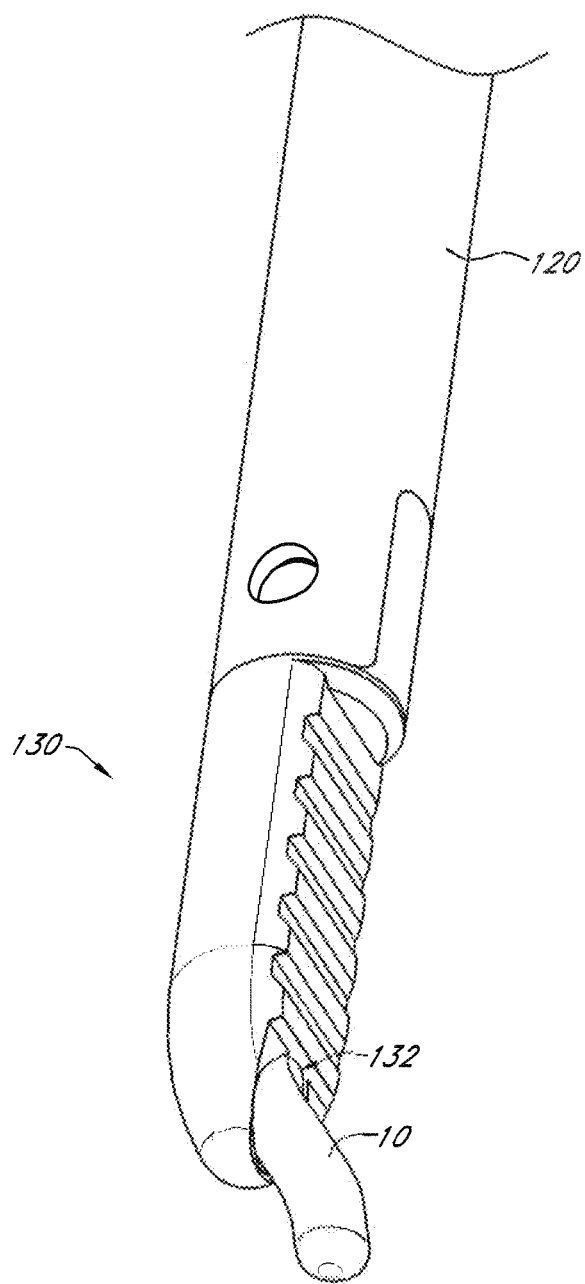
FIG. 6G illustrates the distal tip of FIG. 6F extruding bone graft material.

As shown in FIGS. 6A-6C, a distal end of the tube 120 (which may be any of the tubes described herein) can include a tip 130. The tip 130 can be integrally formed with or coupled, removably or permanently, to the tube 120. In some embodiments, the tube 120 and tip 130 can be a modular system such that different tips can be selected and coupled to the tube 120 for different procedures and/or target locations. The tip 130 can be made of a metallic, radiopaque material to facilitate visualization on, for example, fluoroscopy or x-ray. Alternatively, the tip 130 may be made of another material, for example a durable medical plastic or a composite material, and may include markers to facilitate visualization. In the illustrated embodiment, the tip 130 is somewhat bullet-shaped with a generally triangular cross-section; however, other shapes and configurations are also possible. For example, the tip 130 can be generally flat as shown in the example embodiments of FIGS. 6D-6G. In some embodiments, for example as illustrated in the example embodiment of FIG. 6H-6I, the tip 130 is generally conical. This shape can be beneficial for delivering bone graft material to, for example, a facet joint. In some embodiments, the tip 130 is pointed and/or sharp to dissect or split muscle and tissue as it is advanced through the patient's skin and body to the surgical location. Alternatively, the tip 130 can be blunt to allow for displacement of muscle without risk of cutting of nerves or other tissue. The tip may have a single or multiple openings 132 in fluid communication with the tube 120 lumen and configured to deliver the bone graft material 10 from the tube 120, as shown in FIG. 6G, to the desired location.

Figure 6H:
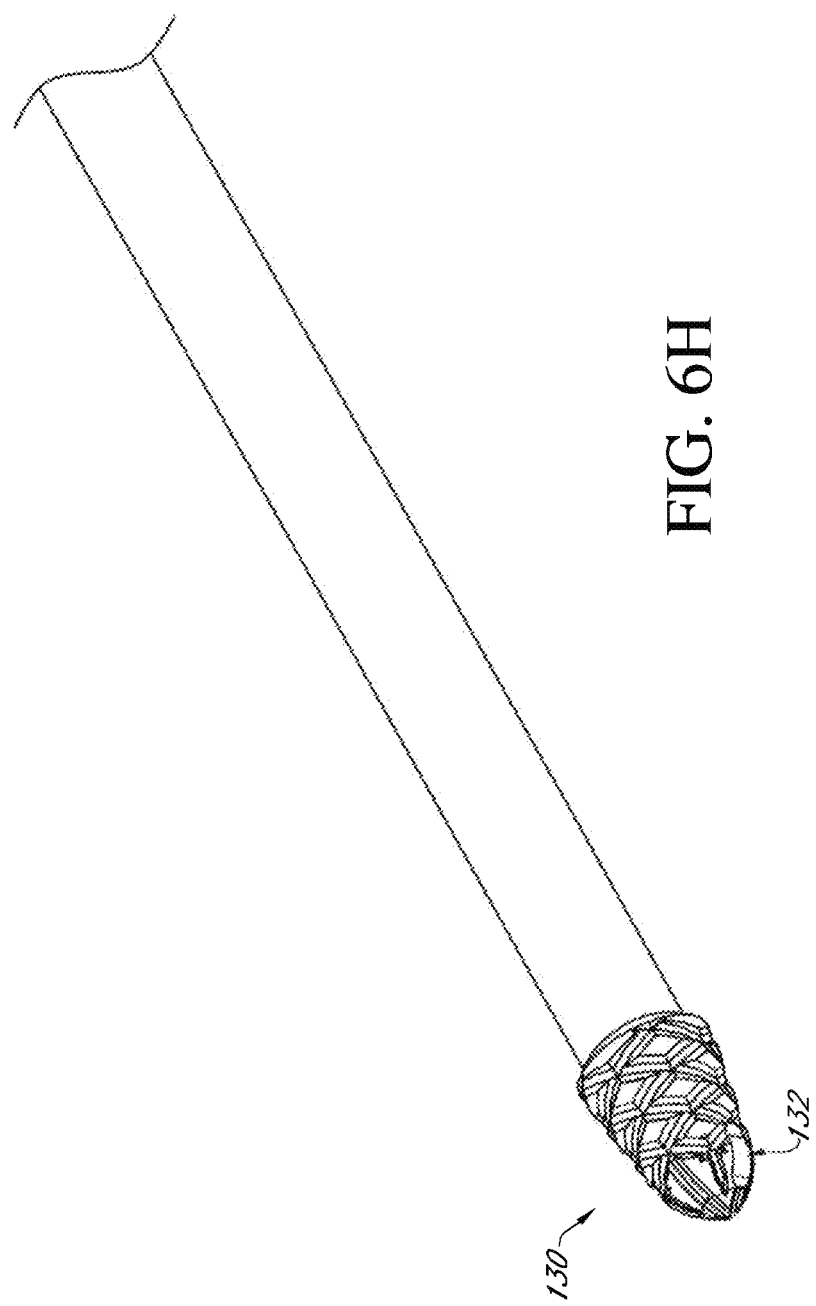
FIG. 6H illustrates an example embodiment of a rasping distal tip coupled to a tube of a bone graft delivery device.
Figure 6I:
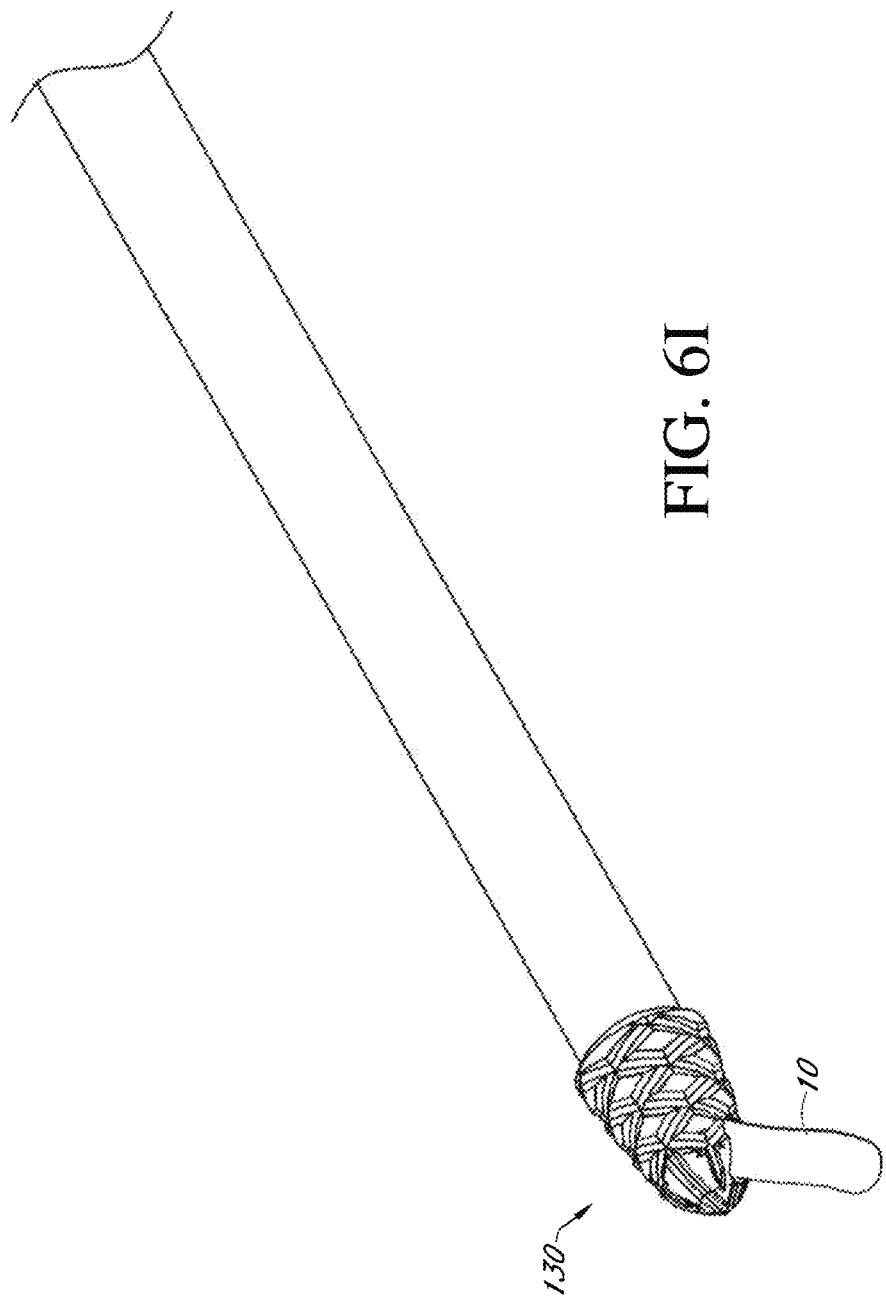
FIG. 6I illustrates the distal tip of FIG. 6H extruding bone graft material.

In some embodiments, at least one side or area of the tip 130 includes a series of jagged edges or other suitable surface 134 configured to serve as a rasp for scraping bone. As shown in FIGS. 6A and 6C, the edges may be triangular in shape, and as shown in in FIGS. 6D-6G, they may be flat. With respect to the embodiment shown in FIGS. 6D-6G, the jagged edges may form a plurality of flat surfaces parallel with each other all within the same plane. In some embodiments, for example as shown in FIGS. 6H-6I, the rasping surface 134 can include a roughened surface extending around an outer surface of the tip. The rasp may be operated manually or by mechanical, battery powered, electric, pneumatic, or any other means of force to allow for decortication of the area to receive the bone graft material. In some embodiments, the opening(s) 132 for delivering bone graft material is located on a side(s) or portion(s) of the tip 130 that does not include a rasping surface, for example as shown in FIGS. 1A-1B and 6A-6C. In some embodiments, the opening(s) 132 is located on a side(s) or portion(s) that does include a rasping surface, for example as shown in FIGS. 6D-6I and 8A.

In some embodiments, the delivery device 100 includes a sleeve slidably or telescopingly disposed over the tip 130. In some embodiments, the sleeve can extend to a proximal end of the tube 120 adjacent the handle 102 so that a user can distally advance or proximally retract the sleeve by manipulating a proximal end of the sleeve. In other embodiments, the sleeve extends over only a portion of the tube 120 or over only the tip 130 and the delivery device 100 includes an actuating mechanism that allows the sleeve to be advanced and retracted. The sleeve can be disposed over the tip 130 during insertion of the tip 130 to the target area to advantageously protect skin, tissue, and/or muscle along the insertion path from damage or injury from the rasping surface 134 and to allow the tip 130 to pass through the skin, tissue, and/or muscle more easily. Once the tip is positioned in the target location, the sleeve can be proximally retracted to expose the rasping surface 134 for decortication of the target area. After decortication and/or after delivery of the bone graft material, the sleeve can be distally advanced to cover the rasping surface 134 for withdrawal of the tip 130 from the body.

Figure 7A:
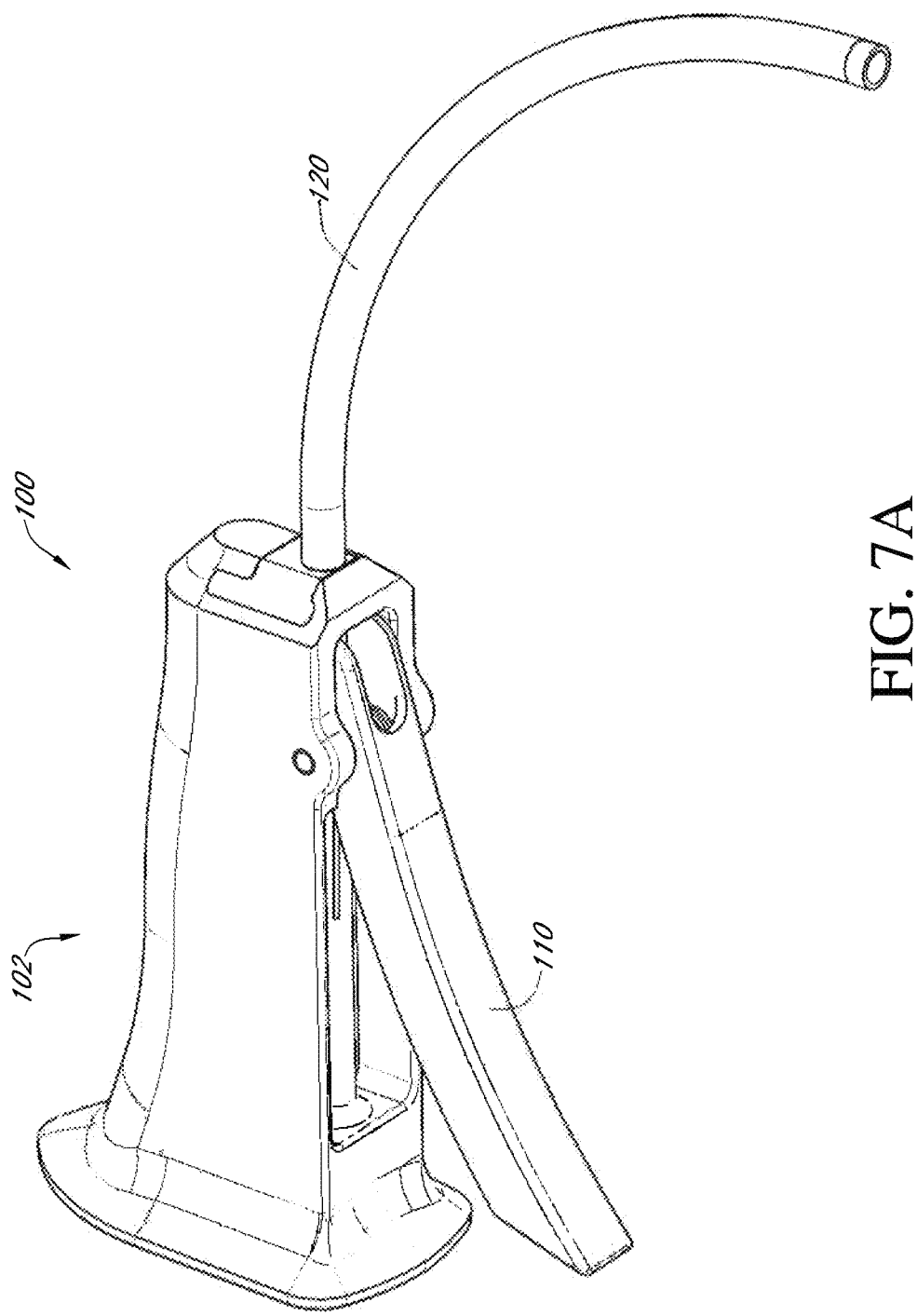
FIG. 7A illustrates a perspective view of an example embodiment of a bone graft delivery device.
Figure 7B:
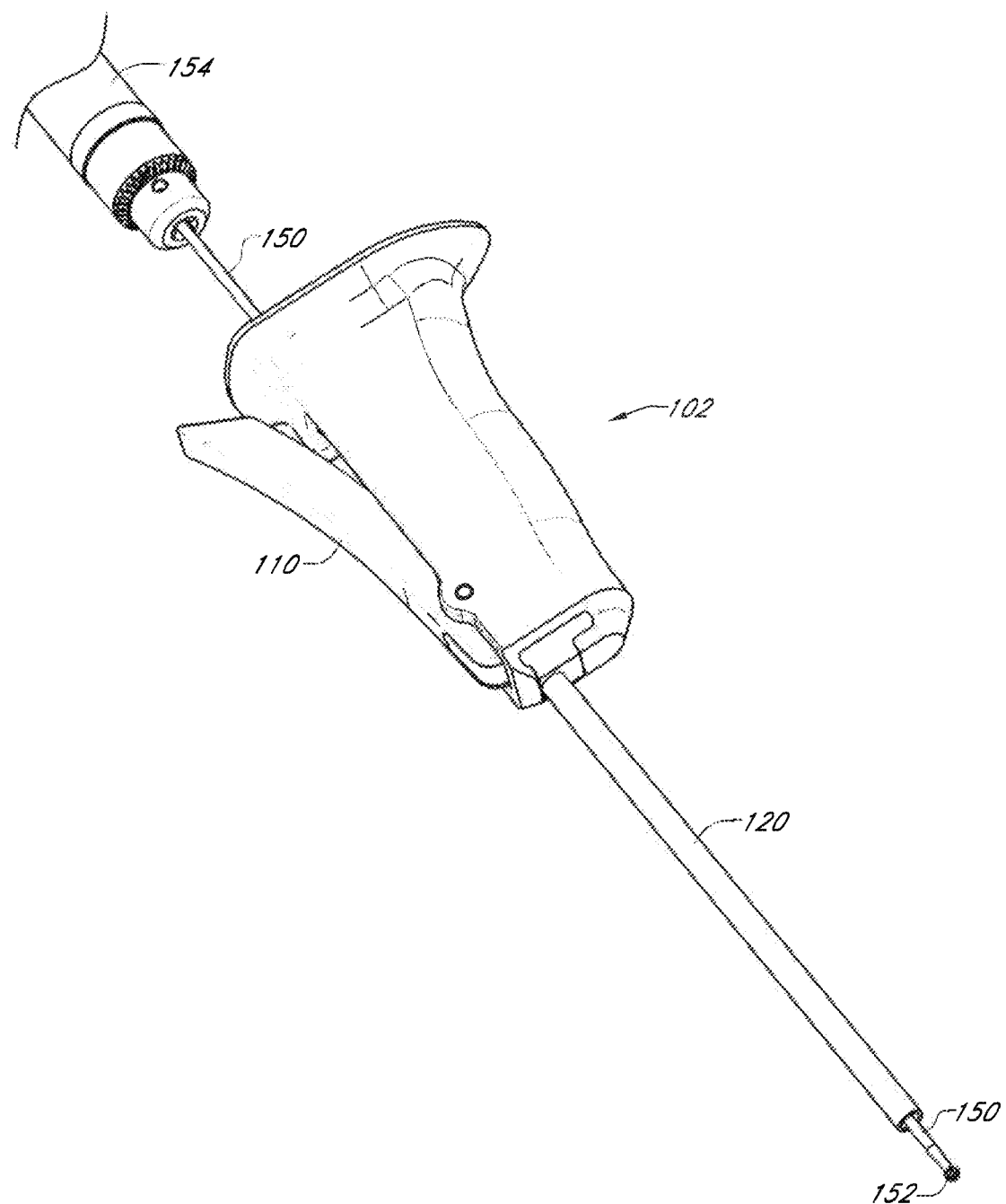
FIG. 7B illustrates a perspective view of an example embodiment of a bone graft delivery device including a shaft having a distal burr disposed therethrough.
Figure 7C:
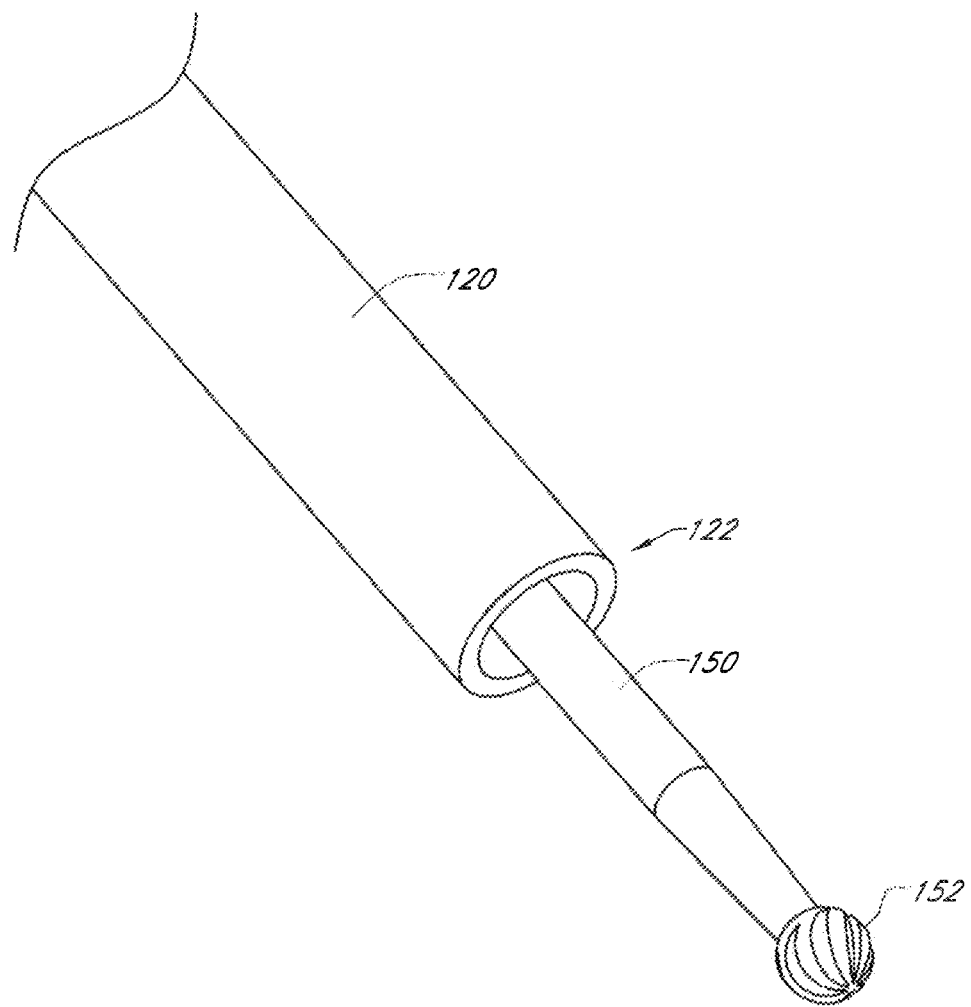
FIG. 7C illustrates an enlarged view of the distal end of the bone graft delivery device of FIG. 7B.

In some embodiments, the distal end of the tube 120 does not include a rasping tip 130, for example as shown in FIGS. 7A-7C. In some such embodiments, an elongate shaft 150 having a burr 152 at a distal end can be inserted through the tube 120 as needed or desired to decorticate a target area, for example as shown in FIGS. 7B and 7C. The burr 152 can have various shapes and configurations, for example, a generally spherical shape as shown in FIGS. 7B and 7C, a bullet shape similar to the distal tip 130 shown in FIGS. 6A-6C, a generally flat shape similar to the distal tip 130 shown in FIGS. 6D-6G, a generally conical shape as shown in FIGS. 6H-6I, or any other suitable shape or configuration. The use of a separate instrument for decortication can advantageously allow the user to select different burrs, rasps, or the like for different patients, target areas, or situations. The elongate shaft 150 and burr 152 can be operated manually. Alternatively, a proximal end of the shaft 150 can be coupled to a drill 154 or another device to provide decortication by mechanical, battery powered, electric, pneumatic, or any other means of force.

In some embodiments, the distal end of the tube 120 includes a radiopaque ring or other marker 122 as shown in FIG. 7C to allow for visualization on, for example, x-ray or fluoroscopy. In some embodiments, the radiopaque ring 122 can be used to assist the user in assessing depth during the procedure. In some embodiments, for example as shown in FIG. 4O, the radiopaque ring 122 can be press fit or snapped onto the distal end of the tube 120 during manufacturing and assembly. In some embodiments, for example as shown in FIG. 4W, the radiopaque ring 122 can be press fit or snapped into a groove 222 near a distal end of the tube 120. In the illustrated embodiment, the groove 222 is distal to the threads 125b configured to receive the tube end cap 124 and is therefore covered by the tube end cap 124 when the tube end cap 124 is coupled to the tube 120. In some embodiments, the radiopaque ring 122 can be co-molded with the tube 120 during manufacturing.

In some embodiments in which the handle 102 and tube 120 have a modular construction such that the tube 120 is removably coupleable to the handle 102, the tube 120 can be provided preloaded or can be loaded with a loading device prior to being coupled to the handle 102. FIGS. 17A-18D show example embodiments of loading devices 600 for loading bone graft material into the tube 120. Such loading devices 600 can allow the user to load the tube 120 with any bone graft material or combination of bone graft materials he or she wishes or deems appropriate. For example, the user can use synthetic, autologous, stem cell, DMB, cadaveric, and/or any other available bone graft material.

As shown in the embodiments of FIGS. 17A-17F, the loading devices 600 include a hollow tube body 602, a plunger shaft 604, a plunger 605, and a cap or coupling 608. In some embodiments, the tube body 602 can hold a volume of about 20 cc, although other sizes and volume are also possible. The tube body 602 can have a smooth or generally smooth inner wall. In some embodiments, the tube body 602 includes measurement markings to allow the user to determine the amount of bone graft material within the tube body 602. The tube body 602 includes a distal tip or end 610. As shown, the distal tip 610 has a smaller diameter than the tube body 602. The tube 120 of a bone graft delivery device 100 such as those described herein is coupled to the distal tip 610 for loading. In some embodiments, the distal tip 610 is internally threaded to receive and engage external threads 125a at or near the proximal end of the tube 120 (shown in FIG. 4O). In some embodiments, the plunger 605 is made in part or entirely of rubber. The plunger 605 is coupled, either removably or permanently, to a distal end of the plunger shaft 604. In some embodiments, the plunger shaft 604 and plunger 605 are integrally molded or formed. The plunger 605 has a greater diameter than the plunger shaft 604 and is sized and shaped to contact and seal against the inner wall of the tube body 102. In some embodiments, the loading device 600 includes a handle 606 that allows the user to better grip the plunger shaft 604. As shown, the handle 606 is integrally molded or formed or coupled, either removably or permanently, to a proximal end of the plunger shaft 604.

The handle 606 can have various shapes and configurations, for example as shown in the embodiments of FIGS. 17A-17C and 17D-17F.

As shown, the plunger shaft 604 is externally threaded. The cap or coupling 608 couples to a proximal end of the tube body 602, for example, via a threaded, snap-fit, or other suitable connection. In some embodiments, the cap 608 couples to the tube body 602 via a combined snap fit and rotational coupling mechanism whereby the cap 608 is attached to the tube body 602 by rotating the cap 608 (e.g., clockwise) until the cap 608 snaps into place; the cap 608 can be removed from the tube body 602 by rotating the opposite direction (e.g., counter clockwise) to disengage the snap fit and rotating until the cap 608 fully releases from the tube body 602. The cap 608 has a through-hole that is sized to receive the plunger shaft 604 therethrough and internally threaded to engage the external threads of the plunger shaft 604. The cap 608 can be predisposed on the plunger shaft 604. The cap 608 can be threaded along the plunger shaft 604, but can be retained on the plunger shaft 604, which has a larger diameter than the plunger shaft 604 and therefore a larger diameter than the through-hole in the cap 608 that is sized to engage the plunger shaft 604.

Figure 17A:
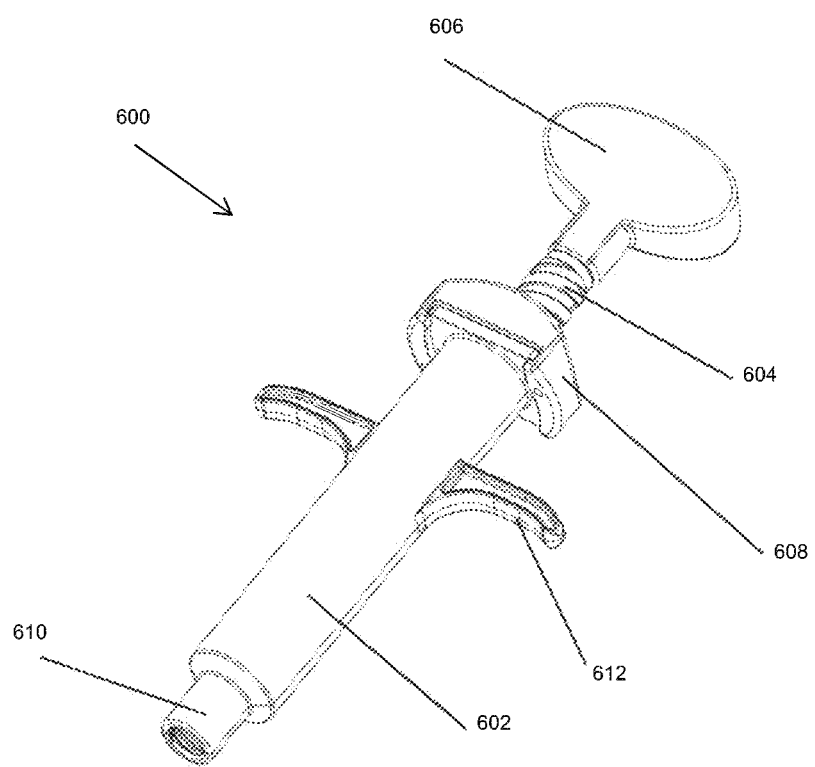
FIG. 17A illustrates a perspective view of an example embodiment of a bone graft loading device.
Figure 17B:
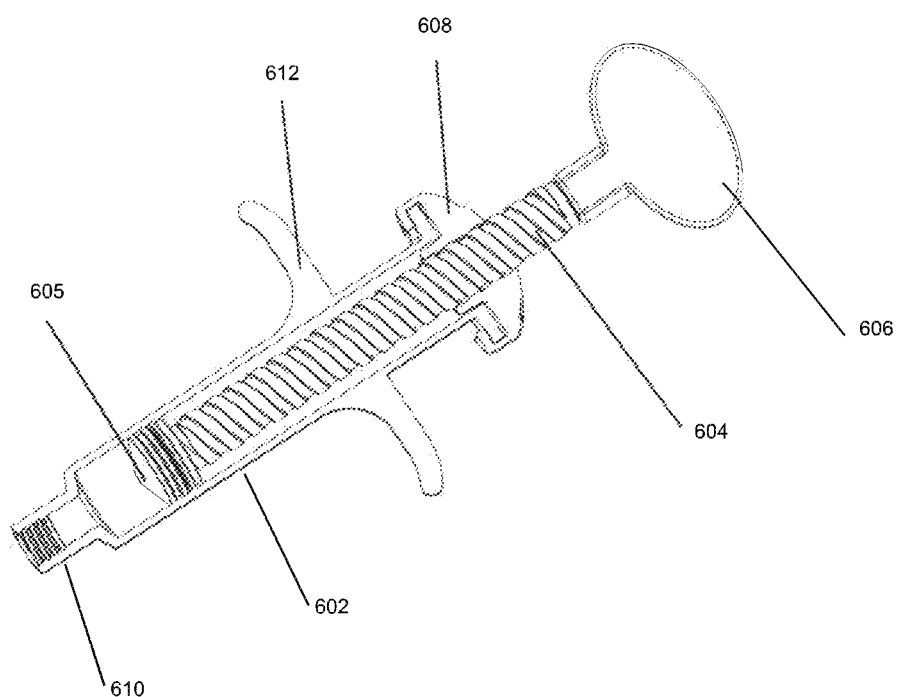
FIG. 17B illustrates a section view of the bone graft loading device of FIG. 17A.
Figure 17C:
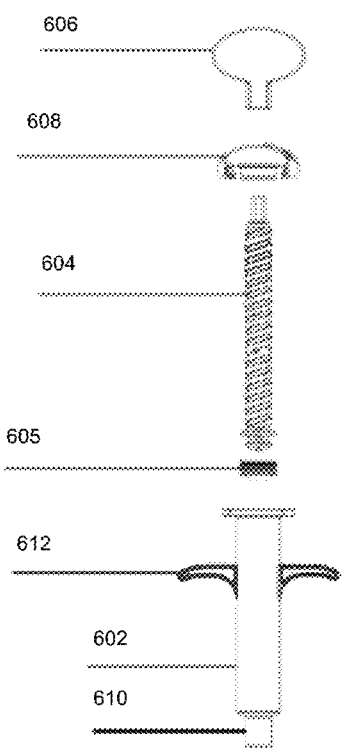
FIG. 17C illustrates an exploded view of the bone graft loading device of FIGS. 17A-17B.
Figure 17D:
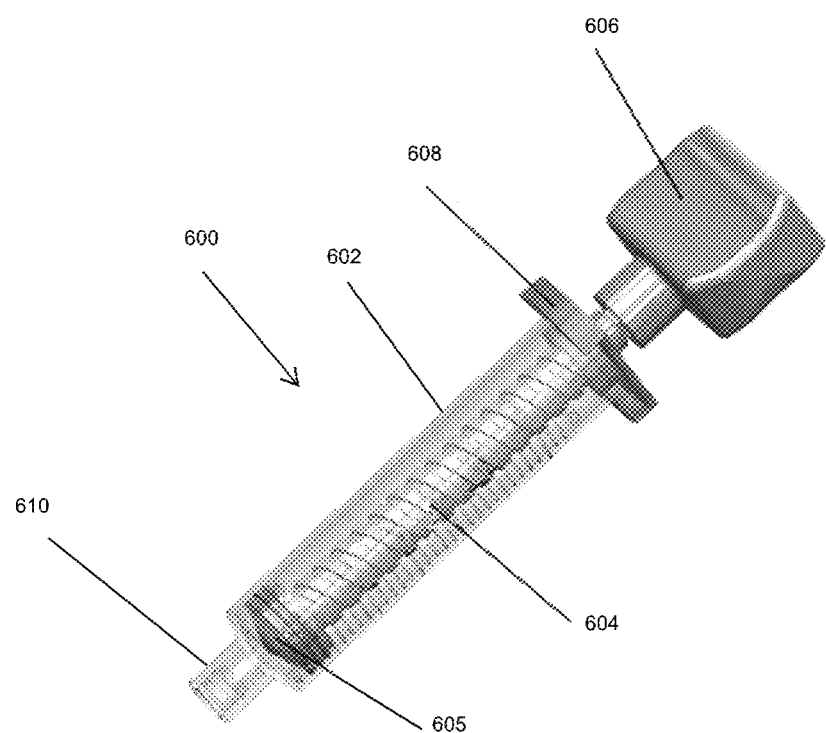
FIG. 17D illustrates a perspective view of another example embodiment of a bone graft loading device.
Figure 17E:
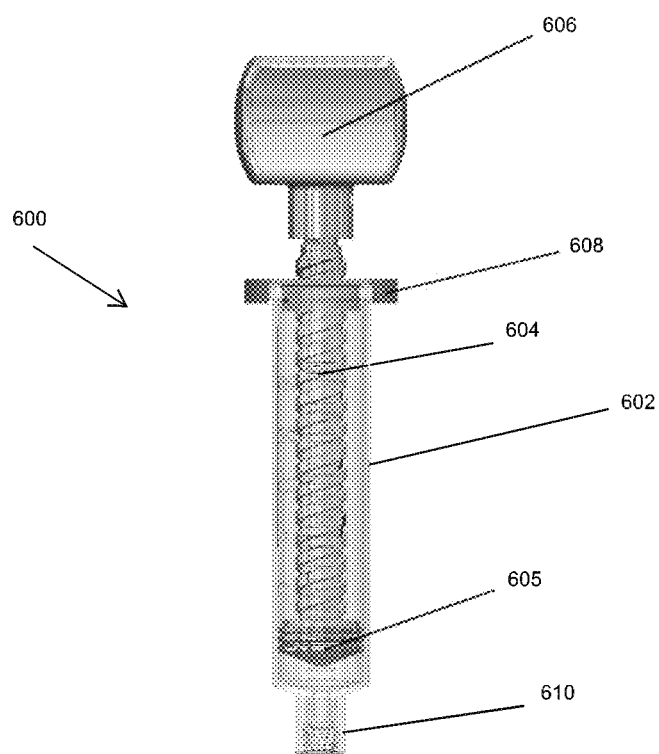
FIG. 17E illustrates a side view of the bone graft loading device of FIG. 17D.
Figure 17F:
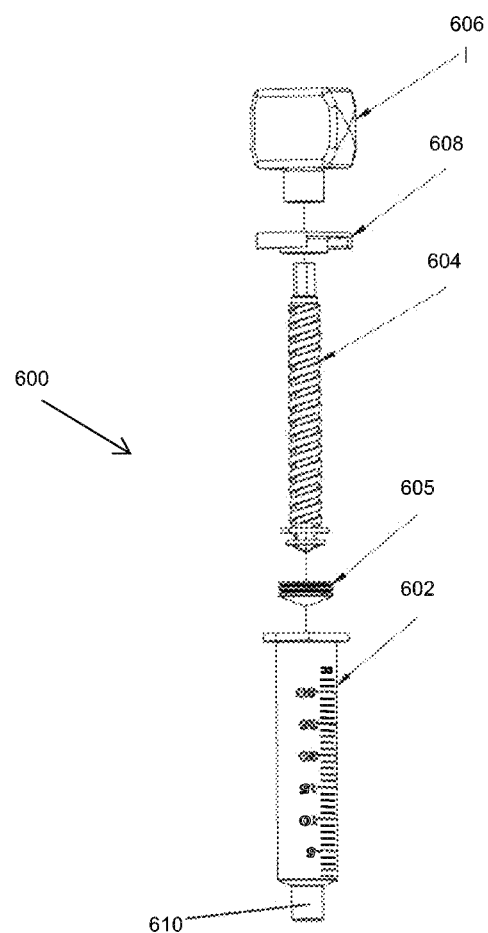
FIG. 17F illustrates an exploded view of the bone graft loading device of FIGS. 17D-17E.

In some embodiments, for example as shown in the embodiment of FIG. 17A-17C, the tube body 602 includes handles or wings 612 extending generally laterally outwardly from the tube body 602. The wings 612 can advantageously allow the user to grip the tube body 602 more easily and securely in use. The wings 612 can have various shapes and configurations as shown.

In use, the user can couple the tube 120 of the bone graft delivery device 100 to the distal tip 610 of the loading device 600 before or after loading the desired bone graft material into the tube body 602. If needed, the user threads the cap 608 to the distal end of the plunger shaft 604 proximate the plunger 605. The user then inserts the plunger 605 into the tube body 602 and couples the cap 608 to the proximal end of the tube body 602. To transfer the bone graft material from the tube body 602 to the tube 120, the user rotates the plunger shaft 604 (e.g., clockwise), for example, by rotating the handle 606, into the cap 608. The internally threaded cap 608 converts the rotational motion of the externally threaded plunger shaft 604 relative to the cap 608 into translational motion of the plunger shaft 604 and plunger 605 distally within the tube body 602. Distal motion of the plunger 605 forces the bone graft material through the distal tip 610 and into the tube 120. The threaded coupling between the plunger 605 and the cap 608 advantageously allows the user to apply greater torque compared to a syringe-type arrangement wherein the plunger is simply pushed distally within the tube body. This greater torque allows the bone graft material to be loaded into the tube 120 more easily. When a desired amount of bone graft material has been loaded into the tube 120, the user can remove the tube 120 from the loading device 600 and couple the tube 120 to a handle 102 for use. If needed during the course of a procedure, the tube 120 can be decoupled from the handle 102, reloaded with the loading device 600, then decoupled from the loading device 600 and recoupled to the handle 102 to continue the procedure.

Figure 18A:
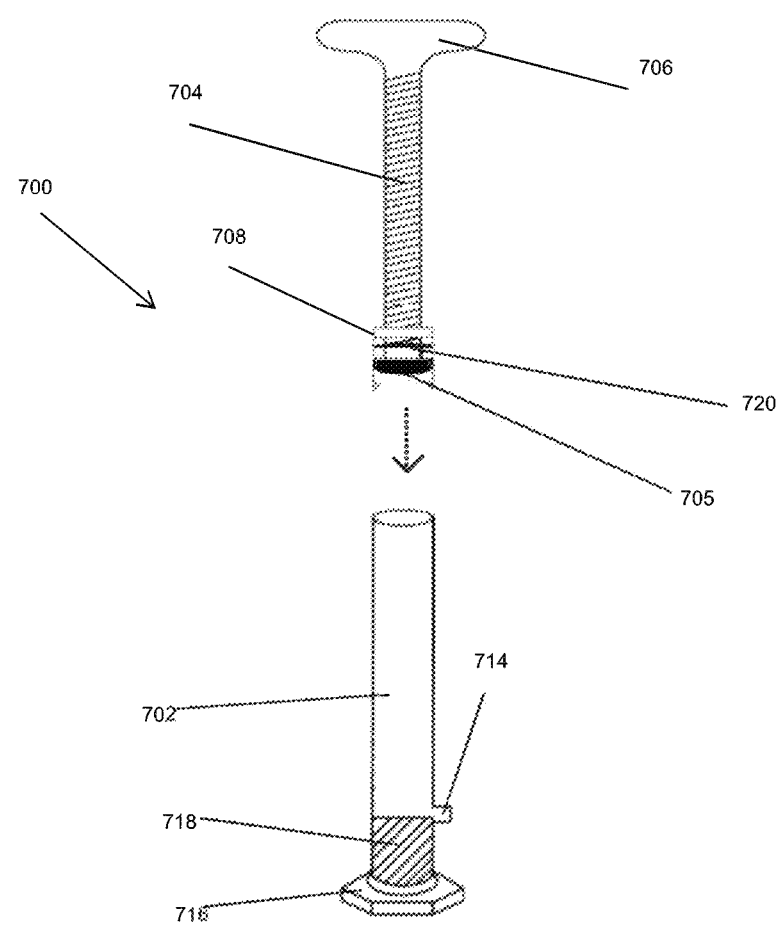
FIG. 18A illustrates an exploded view of another example embodiment of a bone graft loading device.

FIGS. 18A-18D illustrate an alternative embodiment of a loading device 700. The loading device 700 similarly includes a tube body 702, an externally threaded plunger shaft 704, a plunger 705, and an internally threaded cap or coupling 708 that couples to a proximal end of the tube body 702. As shown in FIG. 18D, the cap 608 can include an internally threaded proximal ring 722 and two arms 724 extending distally from the proximal ring 722 on opposite sides of the proximal ring 722. Distal ends of the arms 724 can include hooks to secure the cap 608 to the tube body 702. Other shapes and configurations for the cap 708 are also possible. As shown in FIG. 18C, a plunger stop 720 can be disposed about the plunger shaft 704 proximate the distal end of the plunger shaft 704 and the plunger 705. As shown in FIG. 18A, the proximal ring 722 of the cap 708 is disposed about the plunger shaft 704 proximal to the plunger stop 720. The plunger stop 720 can help prevent or inhibit the cap 708 from falling off the plunger shaft 704. In the illustrated embodiment, the loading device 700 also includes a handle 706 at the proximal end of the plunger shaft 704. The handle 706 can be integrally formed with the plunger shaft 704 as shown or can be coupled, removably or permanently, to the plunger shaft 704. In the illustrated embodiment, the tube body 702 includes a side spout 714 extending laterally from a side of the tube body 702 and in fluid communication with the internal volume of the tube body 702.

In some embodiments, the loading device 700 includes a base 716, which can advantageously allow the loading device 700 to stand on a table or other support surface before, during, or after use. In some embodiments, the loading device 700 includes a tube stop 718 that fills the internal volume of the tube body 702 between the distal end or bottom of the tube body 702 and the side spout 714. In the illustrated embodiment, the tube stop 718 extends proximally within the tube body 702 to a point proximal to a distal side of the side spout 714. This can help encourage as much bone graft material as possible to travel through the side spout 714 to the tube 120 and reduce potential waste of bone graft material settling into a distal end of the tube body 702 distal to or below the side spout 714. In some embodiments, the tube stop 718 can be made of a material that adds some weight to the bottom of the tube body 702 to advantageously provide the tube body 702 with greater stability when placed on a table or other surface.

The loading device 700 operates similarly to the loading devices 600 described above. However, in this embodiment, the tube 120 of the bone graft delivery device 100 is coupled to the side spout 714 for loading, and advancement of the plunger shaft 704 and plunger 705 distally within the tube body 702 forces the bone graft material within the tube body 702 through the side spout 714 and into the tube 120.

In some embodiments, the bone graft delivery device 100 can be configured to deliver bone graft material inside an interbody cage or other interbody device that has been disposed within a disc space. If sufficient bone graft is not applied to a disc space during a fusion procedure, there is a decreased likelihood of fusion and an increased chance of revision surgery. Some interbody implants or cages include an opening or window that can be filled with bone graft. However, this provides for limited surface area for the bone graft to contact the vertebral end plates. In some cases, surgeons use funnels or similar devices to fill the disc space prior to insertion of the implant. However, inserting an interbody cage after delivering bone graft material can disrupt the placement of the bone graft material. Furthermore, it can be difficult to deliver bone graft to the disc space in a controlled manner after the implant has been inserted, and it can be difficult for the surgeon to access the desired area to deliver the bone graft if the implant is already in place. Delivering the bone graft material after inserting the interbody cage and inserting the bone graft material within the interbody cage can help ensure the bone graft material is placed where desired or required. The bone graft delivery device 100 allows for pressurized and controlled delivery of bone graft material into the cage to maximize filling of the cage with the bone graft material.

Figure 14:
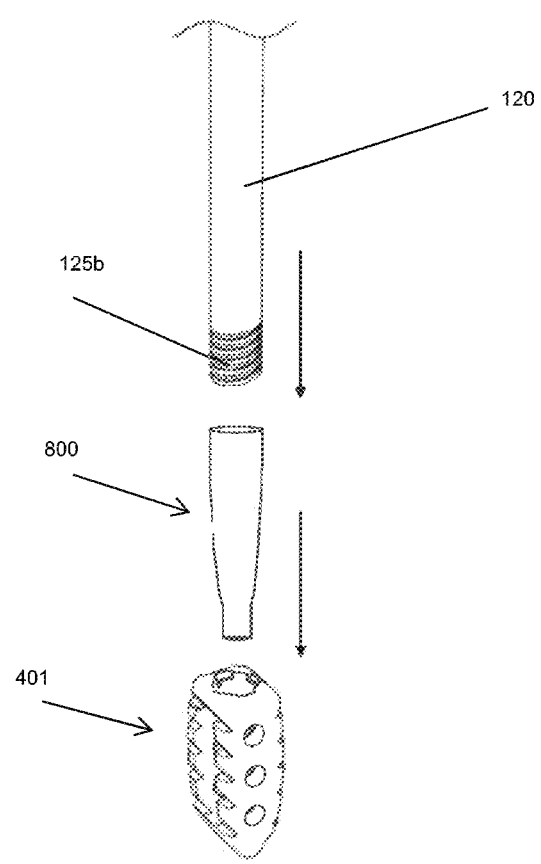
FIG. 14 illustrates an example embodiment of an attachment member coupling a tube of a bone graft delivery device to an interbody cage.

In some embodiments, an attachment member can be provided to couple the distal end of the tube 120 of the bone graft delivery device 100 to the interbody cage. Bone graft material is delivered through the tube 120 and attachment member and into the interbody cage. FIG. 14 illustrates an example embodiment of an attachment member 800 that can couple the distal end of the tube 120 to an interbody cage 401. A proximal end of the attachment member 800 is sized and configured to couple to the distal end of the tube 120, and the distal end of the attachment member 800 is sized and configured to couple to the interbody cage 401. In some embodiments, the proximal end of the attachment member 800 can be internally threaded to engage external threads 125*b* at the distal end of the tube 120. In other embodiments, the attachment member 800 can couple to the tube 120 via a snap fit or another suitable connection mechanism. Various attachment members can be manufactured and/or provided for use with various interbody cages or other interbody devices.

Figure 10A:
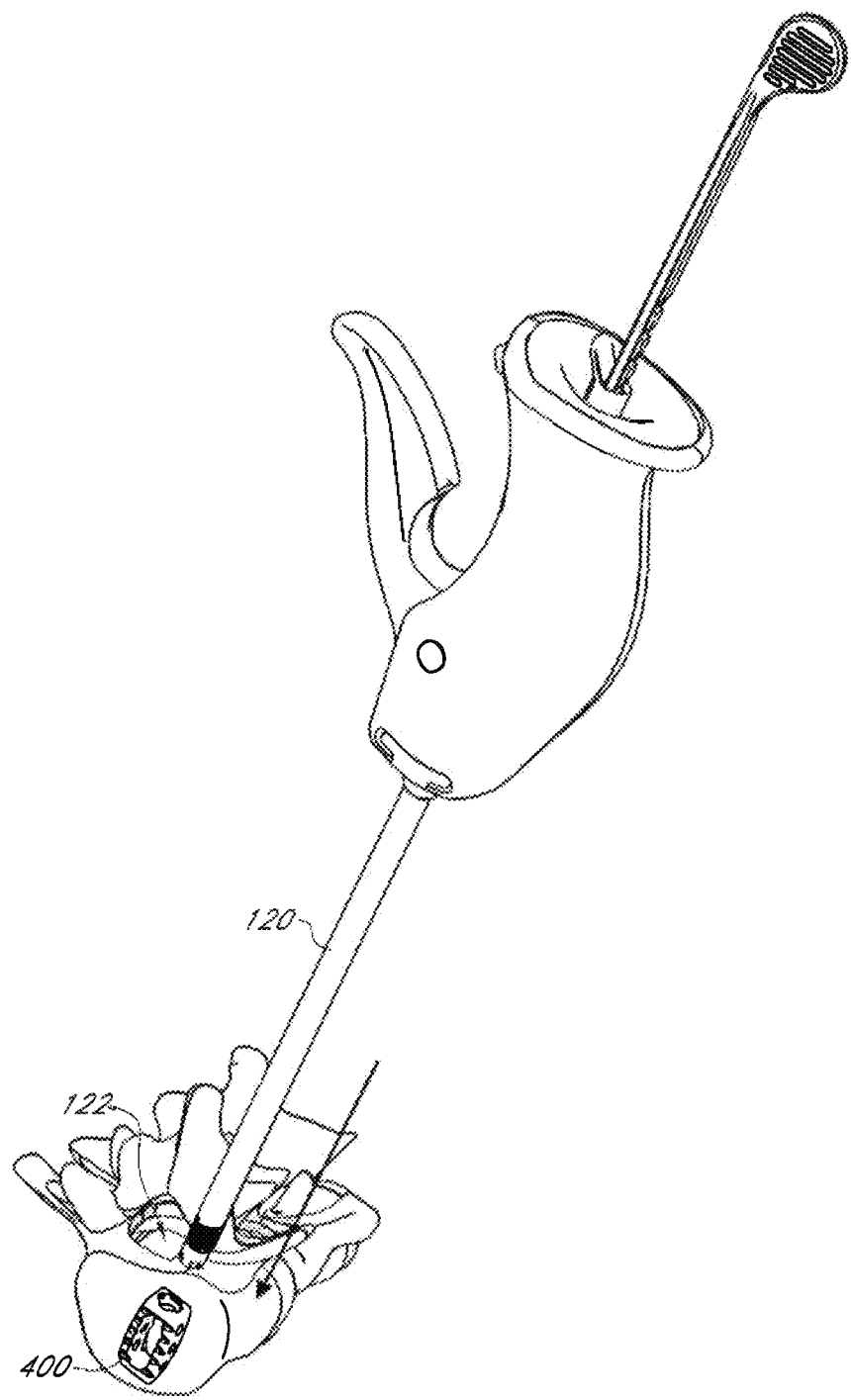
FIGS. 10A-10E illustrate a bone graft delivery device configured to deliver bone graft to an interbody device.
Figure 10B:
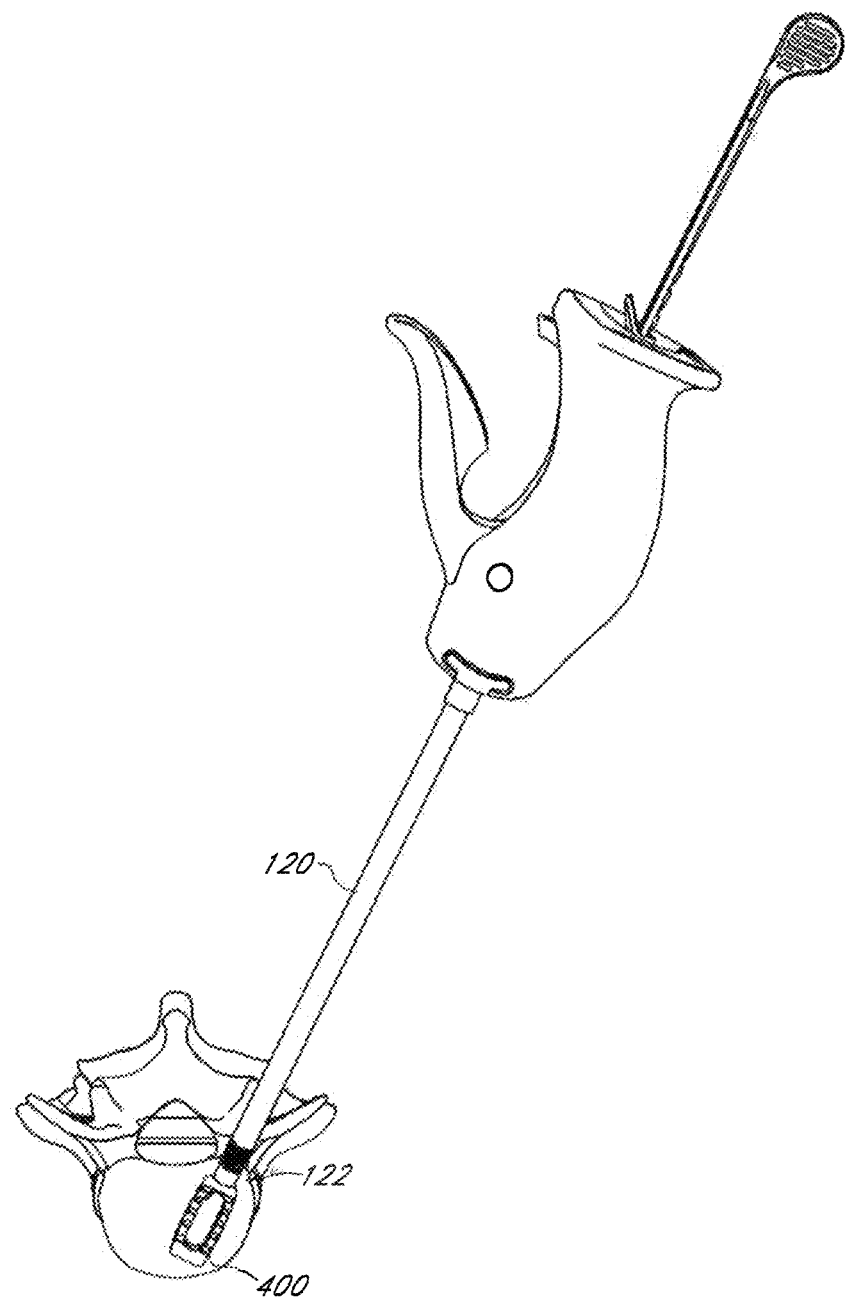
Figure 10C:
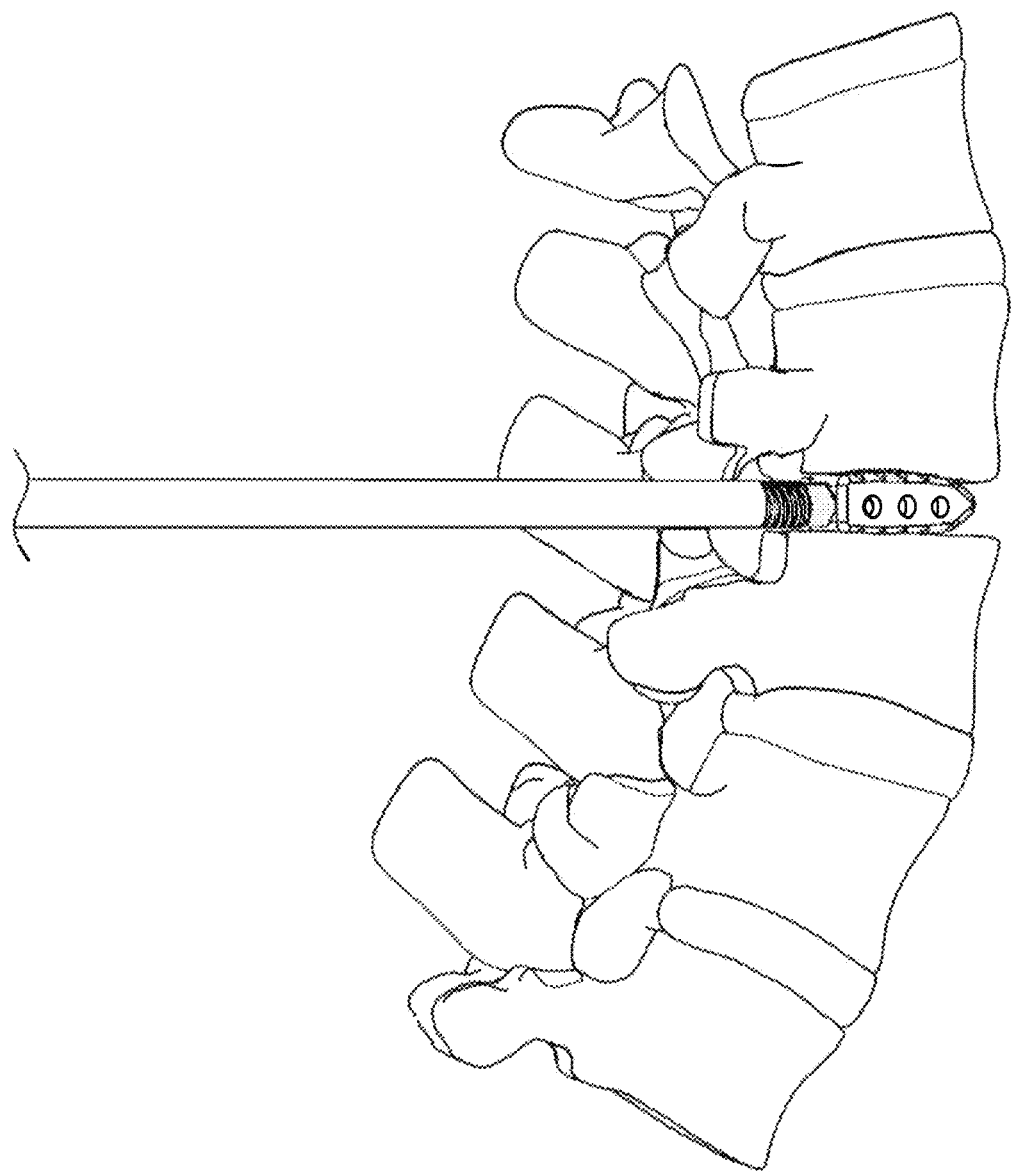
Figure 10D:
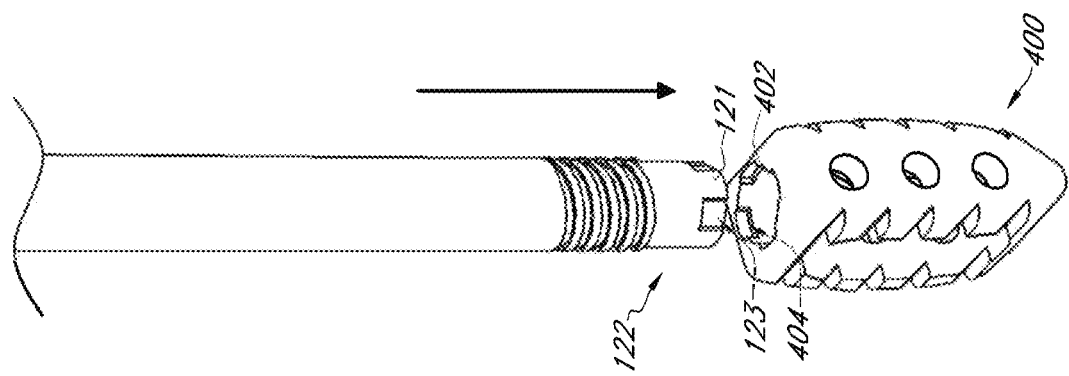
Figure 10E:
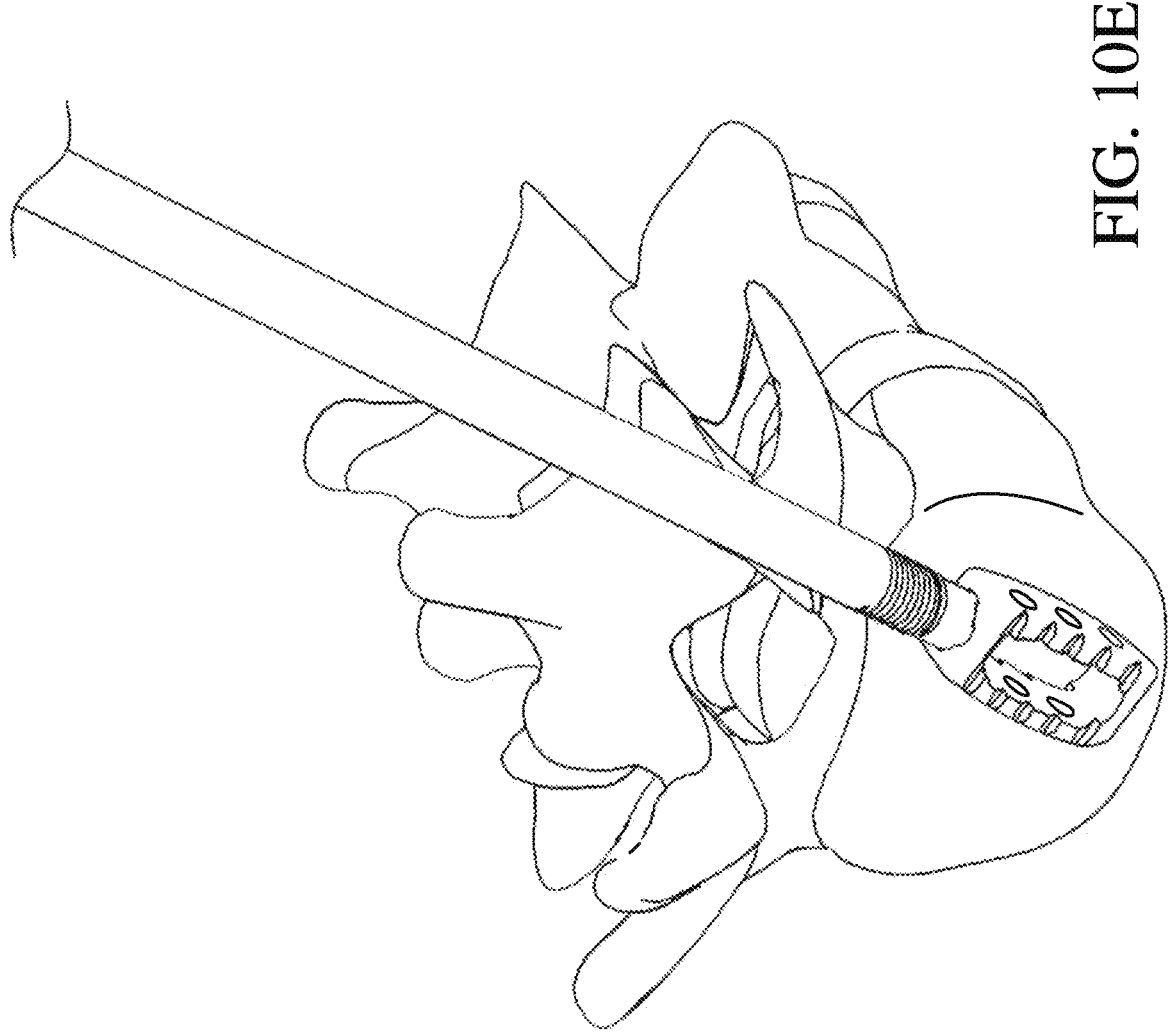

In some embodiments, the distal end of the tube 120 itself includes features configured to engage corresponding features on an interbody device. FIGS. 10A-10E illustrate an example embodiment of a tube 120 having a distal end 122 configured to engage an interbody cage 400. The distal end 122 of the tube 120 can be coupled to the cage 400 after the cage 400 has been placed in the disc space as shown in FIGS. 10A and 10B. As shown in FIG. 10D, the distal end 122 of the tube 120 includes alternating ridges 121 and recesses 123 configured to mate with corresponding recesses 404 and ridges 402 on the cage 400. In some such embodiments, various tubes 120 with different engagement features can be manufactured and/or provided for use with various interbody devices, and the user can select the appropriate tube 120 after selecting the interbody device to be used. In various embodiments, the tubes 120 and/or attachment members can be configured to couple to various cages via threaded connections, snap fit connections, clip-on connections, wedge connections, and/or any other suitable connection mechanism. In some embodiments, the tubes 120 and/or attachment members can be configured to abut one or more cages without such a connection mechanism.

Figure 15A:
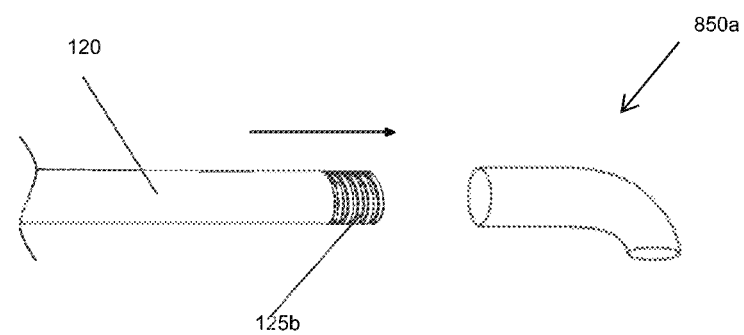
FIGS. 15A-15B illustrate example embodiments of applicators configured to be coupled to a tube of a bone graft delivery device to direct bone graft material in various directions.
Figure 15B:
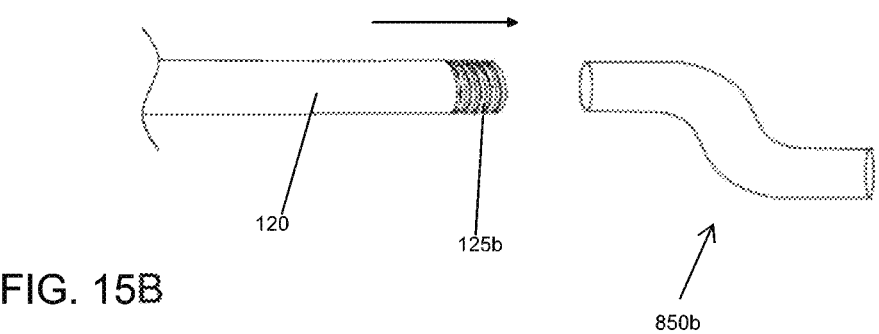

FIGS. 15A-15B illustrate example embodiments of applicators 850*a*, 850*b* that can be coupled to the distal end of the tube 120 to direct bone graft in various directions. For example, in some embodiments, the applicators 850*a*, 850*b* allow bone graft material to be directed around a cage disposed within the disc space. A proximal end of the applicator 850*a*, 850*b* couples to the distal end of the tube 120. In some embodiments, the proximal end of the applicator 850*a*, 850*b* is internally threaded to engage external threads 125*b* at the distal end of the tube 120. In other embodiments, the applicator 850*a*, 850*b* can couple to the tube 120 via a snap fit or another suitable connection mechanism. The applicators 850*a*, 850*b* can have various shapes. FIG. 15A illustrates an applicator 850*a* having an approximately 90° curve proximate the distal end such that bone graft material can be extruded in a direction approximately 90° from the distal end of the tube 120. FIG. 15B illustrates an applicator 850*b* having an S-shape or serpentine shape. In the illustrated embodiment, the applicator 850*b* allows the bone graft material to be extruded along a direction generally parallel but offset from the distal end of the tube 120. Other shapes and configurations, for example, various curved and/or angular shapes, are also possible.

Figure 11E:
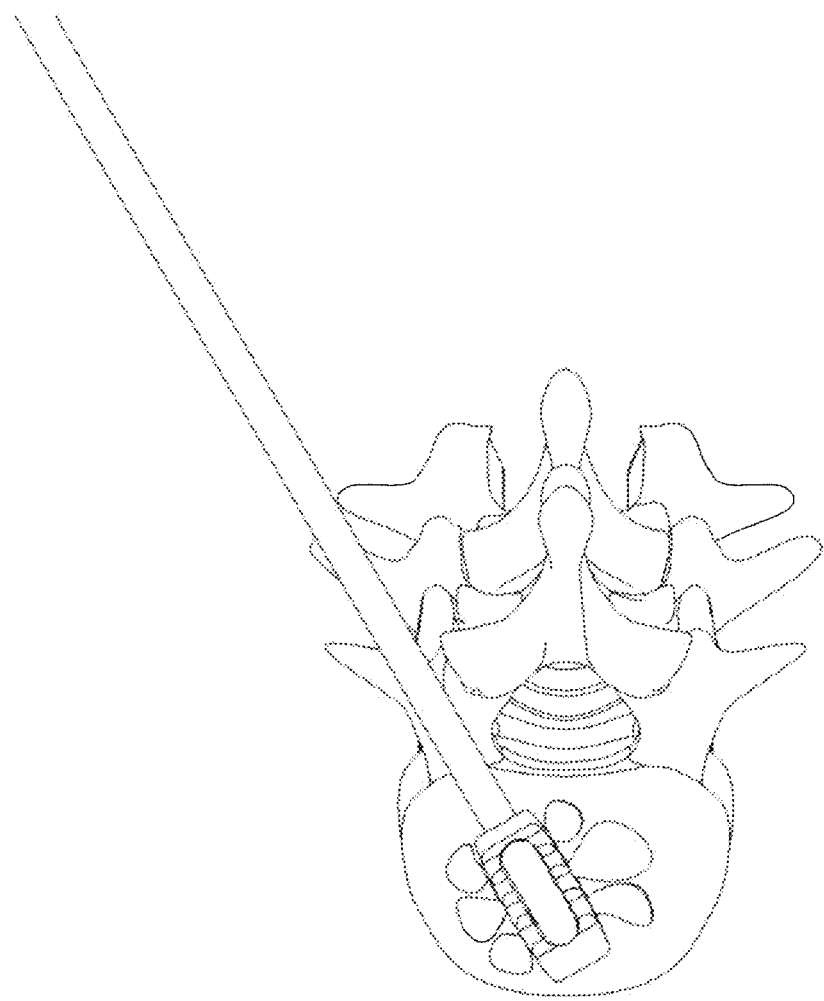
FIG. 11E illustrates a bone graft delivery device coupled to the interbody device of FIGS. 10A-10D disposed within a disc space and bone graft spreading to the surrounding disc space from inside the interbody device.
Figure 12:
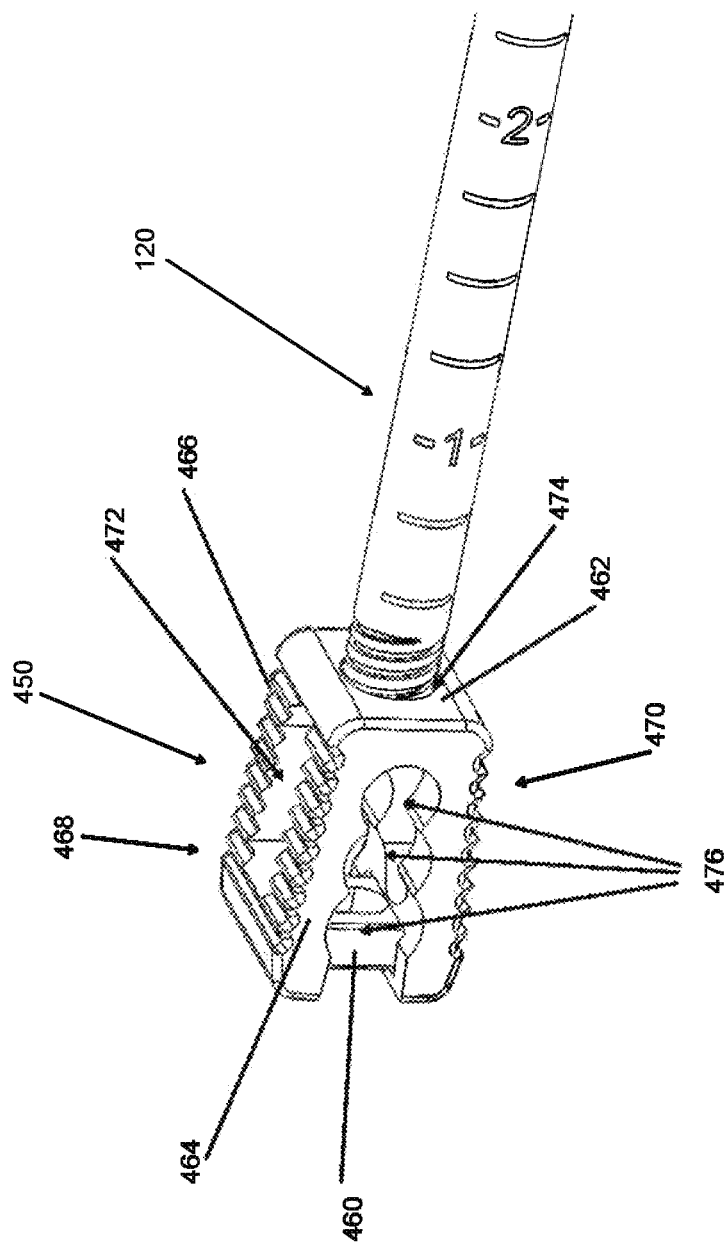
FIG. 12 illustrates an example embodiment of an expandable interbody device coupled to a bone graft delivery device.

Example embodiments of cages that can be used with the bone graft delivery device 100 are illustrated in FIGS. 11A-12. In the embodiment of FIGS. 11A-11D, the cage 400 has a leading end 410, a trailing end 412, and first and second sidewalls 414, 416 extending between the leading end 410 and trailing end 412. In the illustrated embodiment, the leading end 410 is tapered or generally wedge-shaped. The sidewalls 414, 416 have an upper bone contacting surface 418 configured to contact a superior vertebra and a lower bone contacting surface 420 configured to contact an inferior vertebra. The cage 400 also has a central opening 422 bounded by the leading end 410, trailing end 412, and sidewalls 414, 416 and an opening 424 in the trailing end that is in fluid communication with the central opening 422. A perimeter of the opening 424 in the trailing end includes the recesses 404 and ridges 402 configured to mate with the distal end 122 of the tube 120 or attachment member. In other embodiments, the opening 424 can include other engagement features configured to mate with corresponding engagement features on the distal end of the tube 120 or attachment member. The opening 424 is sized to mate with or receive the tube 120 or attachment member and can be larger than openings included in various other cages to mate with insertion instruments. When the distal end 122 of the tube 120 is coupled to the cage 400, the bone graft material can be delivered through the opening 424 into the central opening 422 to promote bone growth into and through the central opening 424 and promote fusion.

As shown, the sidewalls 414, 416 can include holes 426 that are in fluid communication with the central opening 422. The holes 426 allow bone graft material delivered into the central opening 422 from the tube 120 to spread to the surrounding disc space outside of the cage 400, for example as shown in FIG. 11E. In the illustrated embodiment, each of the sidewalls 414, 416 includes three holes 426, although more or fewer holes are also possible. In the illustrated embodiment, the holes 426 have an at least partially conical shape. As shown, a portion of the holes 426 adjacent the central opening 422 and inner surfaces of the sidewalls 414, 416 is generally circular. The perimeter of the holes 426 then flares or tapers outwardly toward outer surfaces of the sidewalls 414, 416, as shown in FIG. 11C. In other embodiments, the perimeter of the holes 426 can be flared or tapered continuously from the inner surfaces of the sidewalls 414, 416 to the outer surfaces of the sidewalls 414, 416. The holes 426 allow bone graft material to spread from inside the central opening 422 to outside of the cage 400 in the surrounding disc space. The tapered shape of the holes 426 allows or promotes dispersal of bone graft material outside of the cage 400 in multiple directions and over a greater area and can allow for a more uniform distribution of bone graft material around the cage 400 in the surrounding disc space to promote fusion.

FIG. 12 illustrates an example embodiment of an expandable cage 450 configured to be coupled to the tube 120 as shown. In some cases in which an expandable cage is used, the surgeon may fill or pack the cage with bone graft before inserting the cage in the patient, then expand the cage within the disc space. However, this then results in excess space within the cage not filled with bone graft material. Coupling the bone graft delivery device 100 to the cage 450 or another expandable cage with the cage in the disc space allows the cage to be filled as it is expanded within the disc space or after it has been expanded to maximize filling of the cage with the bone graft material.

In the illustrated embodiment, the cage 450 has a proximal wall 462, a distal wall 460, and first and second sidewalls 464, 466. The sidewalls 464, 466 have an upper bone contacting surface 468 configured to contact a superior vertebra and a lower bone contacting surface 470 configured to contact an inferior vertebra. The cage 450 also has a central opening 472 and a hole 474 in the proximal wall 462 in fluid communication with the central opening 472 and configured to receive the distal end of the tube 120. The distal end of the tube 120 can be coupled to the proximal wall 462 via a threaded connection as soon or any other suitable mechanism. Similar to the embodiment of FIGS. 11A-11D, one or both of the first and second sidewalls 464, 466 can include one or more holes 476 in fluid communication with the central opening 472. In the embodiment of FIG. 12, the holes 476 are connected to one another. In the illustrated embodiment, a distance between the upper bone contacting surface 468 and the lower bone contacting surface 470 is greater adjacent the distal wall 460 than the proximal wall 462, and a height of the cage 450 increases from the proximal wall 462 to the distal wall 460. In some embodiments, the distal wall 460 includes a mechanism that expands the distal end of the cage 450 relative to the proximal end. The distal end of the tube 120 can be coupled to the cage 450 before or after the cage 450 is expanded to allow the cage 450 to be filled with bone graft material as it is being expanded or after it has been expanded.

Figure 8A:
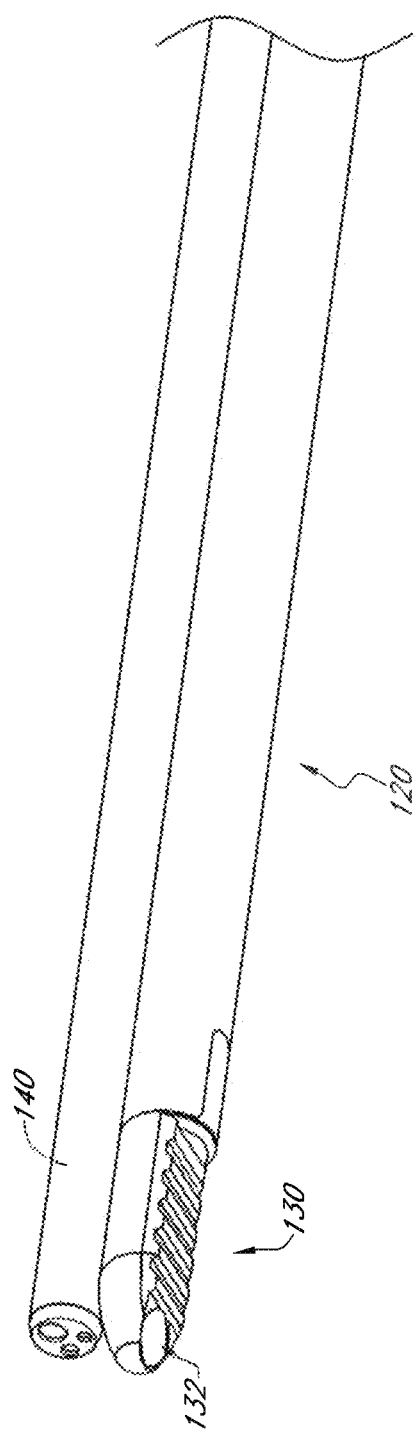
FIG. 8A illustrates a distal section of an example embodiment of a bone graft delivery device including an endoscope.
Figure 8B:
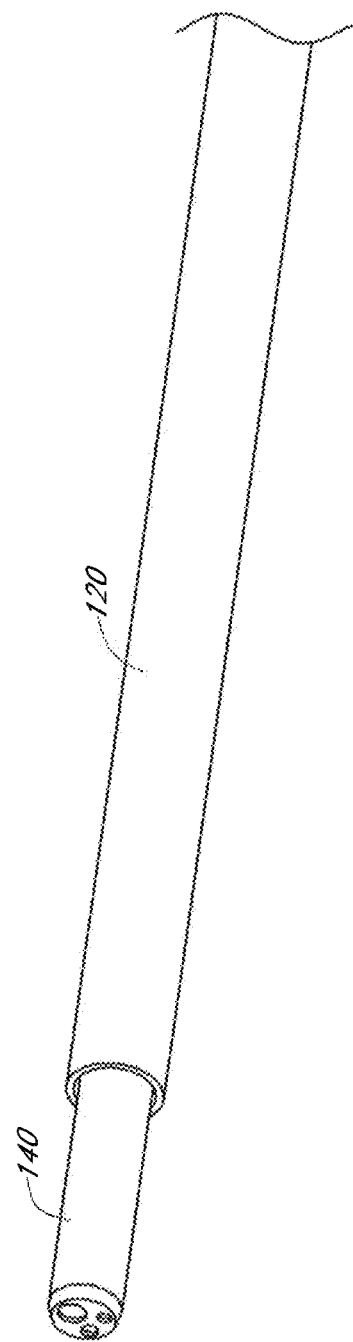
FIG. 8B illustrates a distal section of another example embodiment of a bone graft delivery device including an endoscope.

In some embodiments, the bone graft delivery device 100 can include an endoscope or endoscopic camera to allow for visualization during insertion of the tip 130 to the target area, decortication, and/or delivery of the graft material. This can advantageously allow the physician to visualize muscles, nerves, and other tissue and structures under the skin to help avoid and inhibit damage to sensitive structures. As shown in FIG. 8A, an endoscope 140 can extend along the tube 120 and can be removably or permanently coupled to the tube 120. In some embodiments, the endoscope 140 or camera can extend through the lumen of the tube 120, for example as shown in FIG. 8B.

Figure 9A:
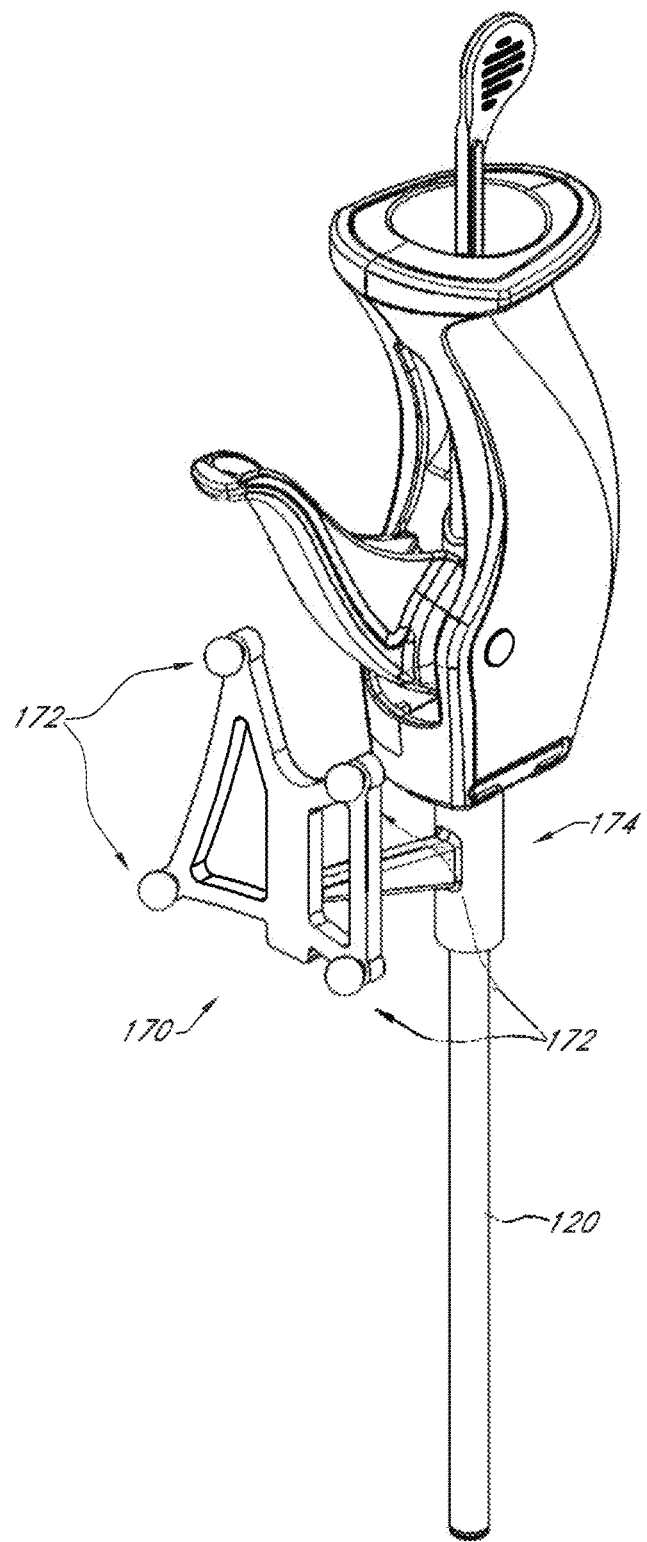
FIGS. 9A and 9B illustrate the bone graft delivery device of FIGS. 2A and 2B with a guide bracket for a surgical navigation system.
Figure 9B:
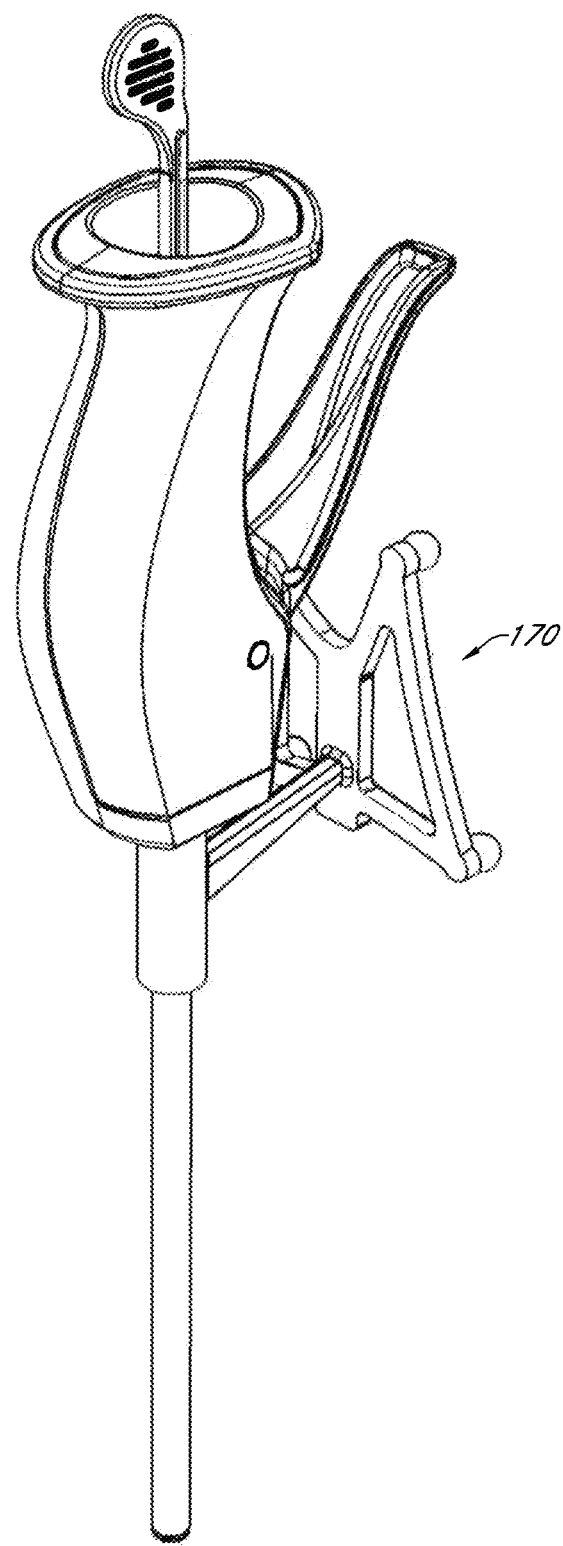

The bone graft delivery device 100 can also or alternatively be used in conjunction with various image-guided surgery systems and devices, such as, for example, Stealth-Station® Navigation Systems available from Medtronic or other navigation systems. In some embodiments, for example as shown in the example embodiment of FIGS. 9A and 9B, the bone graft delivery device includes a guide 170 having markers 172 configured to be visualized with, for example, fluoroscopy or x-ray. The guide 170 can include a sheath 174 configured to receive the tube 120 to couple the guide 170 to the bone graft delivery device. A surgical navigation system can include an imaging modality, such as an X-ray or CT scanner or fluoroscope, and a camera. In use, during preparation for an image-guided surgical procedure, a reference frame, which can include radiopaque markers, is attached to a pin positioned in a reference location in the patient's spine or other target area. Images are taken, and the image data is transferred to the navigation system for processing and registration. During the procedure, the camera can track the position of the markers 172 on the guide 170 relative to the markers on the reference frame. The navigation system can process images obtained by the camera and/or an imaging modality to display the position of the bone graft delivery device on the pre-operative images. In some embodiments, the navigation system can process images obtained by an endoscopic camera extending alongside or through the tube 120 as described herein.

In some embodiments, one or more handles 102 of a bone graft delivery device can be provided in a system or kit with one or more tips 130, tubes 120, and/or other instruments.

The kit can allow a surgeon or other medical personnel to select an appropriate tube 120 and/or tip 130 for the particular patient, procedure, and/or treatment location. As described above, certain tip 130 configurations can be suited for certain target locations. For some procedures, the surgeon may select a curved or straight tube 120 to help improve access to the particular target location and/or may select from two or more tubes 120 having different lengths. In some embodiments, the kit can include an endoscopic camera. In some embodiments, the kit can include one or more separate rasping instruments. The kit can include various other instruments that might be used during an orthopedic procedure.

Figure 13:
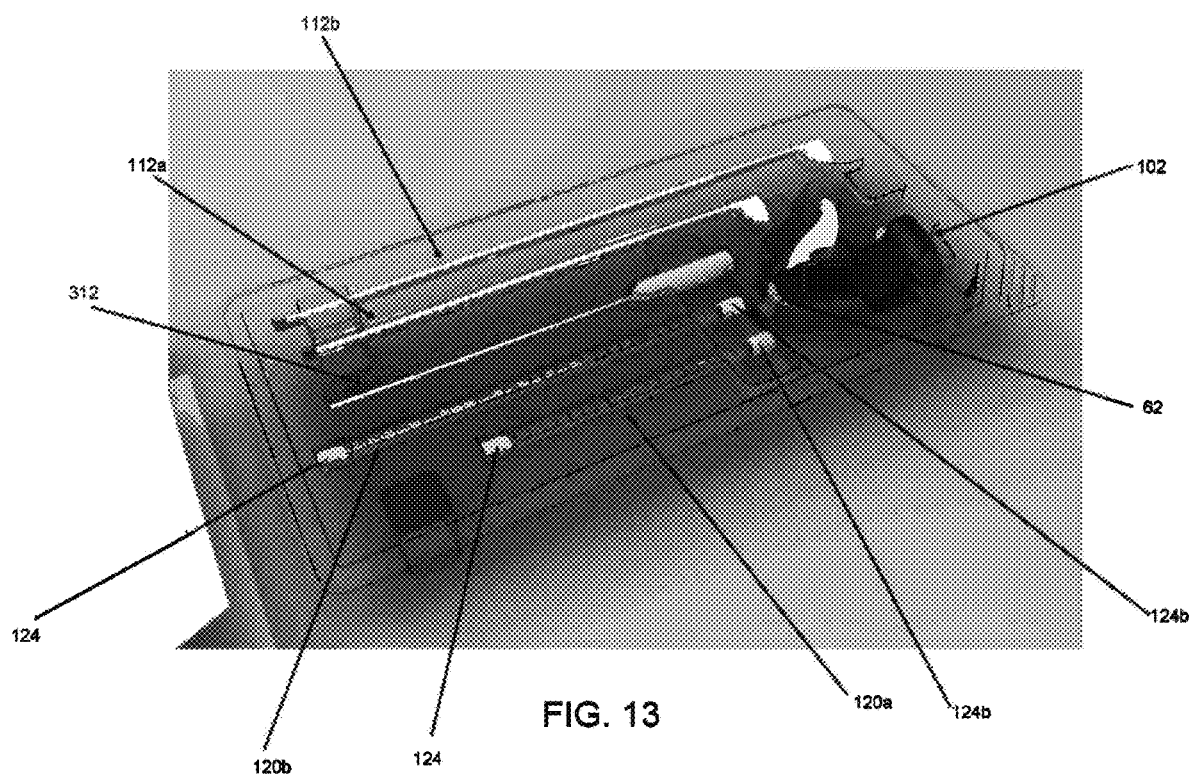
FIG. 13 illustrates an example embodiment of a bone graft delivery system kit.

For example, FIG. 13 illustrates an example embodiment of a kit that can be provided to a surgeon in a tray. In the illustrated embodiment, the kit includes a handle 102, a relatively shorter tube 120a and corresponding relatively shorter plunger 112a, a relatively longer tube 120b and corresponding relatively longer plunger 112b, and a pusher rod 312. The kit can include more or fewer tubes 120 and/or plungers 112. As shown, each tube 120a, 120b includes a tube end cap 124 on its distal end. Each tube also includes a proximal end cap 124b on its proximal end for shipping and storage. For use, the surgeon or other medical professional selects the desired tube 120a, 120b, removes the proximal end cap 124b, and couples the proximal end of the selected tube 120a, 120b to the base 62 of the handle 102. In the case of a handle 102 having a funnel 104, the surgeon or other medical professional can then proceed to load bone graft into the handle 102, use the pusher rod 312 to urge the bone graft material into the tube 120a, 120b, then remove the pusher rod 312 and select the appropriate plunger 112a, 112b for use in delivering the bone graft material using the bone graft delivery device 100. In some embodiments, one or more of the tubes 120a, 120b and/or handle 102 can be provided pre-loaded with bone graft material.

In some embodiments, a kit includes a handle 102, one or more prefilled tubes 120, and one or more plungers 112. For example, the kit can include one or more tubes 120 prefilled with a synthetic bone graft material. In some embodiments, the synthetic bone graft material prefilled in the tube(s) 120 has a composition of about 40-95% calcium phosphate and about 5-60% collagen. As another example, the kit can include one or more tubes 120 prefilled with a demineralized bone matrix material. Any prefilled tubes can be sealed in the kit or other package for shipment and storage to preserve the integrity of the bone graft material. In some embodiments, a kit can be provided including a handle 102, one or more tubes 120, one or more plungers 112, and a bone graft loading device 600, 700. The loading device 600, 700 can be used to load the tube(s) 120 with any appropriate bone graft material the surgeon desires or requires. In some embodiments, the kit can further include one or more types of bone graft material.

In one embodiment, the device 100 described herein may be used in minimally invasive spinal surgery. For example, in a conventional posterolateral spine procedure, screws and or fusion cages may be delivered to adjacent vertebrae using small incisions made in a patient's back. It may additionally be desirable to deliver bone graft material to the surgical location, e.g., to the transverse processes, disc spaces, lamina, or facet joints, through one of these small incisions. The device described herein is sized to be delivered through a minimally invasive opening made in the patient's skin (e.g., through a skin incision of 4 cm or less), and configured so that the tip can be positioned adjacent a pedicle screw or other desired location. The optional curvature of the tube 120 can facilitate positioning of the tip 130 at desired spinal locations and allows, for example, insertion of the device 100 through an incision over one vertebra, and positioning of the tip 130 at an adjacent vertebra. Alternatively, the device can be delivered through any desired opening made in the patient's skin (e.g., minimally invasive, mini-open, or open). If needed, the optional jagged edges or other surface 134 on the device can be used to decorticate desired bone locations, causing bleeding of the bone and creating a surface that promotes bone fusion. The trigger 110 or other actuation mechanism can then be actuated to deliver bone graft material through the tube 120 lumen and optional openings 132 in the tip 130 to promote fusion of the bone.

In some embodiments, an endoscope or camera can be inserted through the tube 120 and used to help guide the physician or other medical professional to the target location and/or to allow the physician to evaluate the area. If the physician wants to decorticate the bone, the physician can remove the endoscope or camera, insert the shaft 150 having the burr 152 or another suitable rasping instrument, and decorticate the target area. In some embodiments, the tube 120 can be inserted into the patient with the shaft 150 or other rasping instrument already inserted or with a rasping tip 130 attached and the physician can use an endoscope, camera, navigation system, or the like placed alongside, adjacent, or proximal the tube 120 to navigate to and/or evaluate the target area. Once the target location is ready, the physician can remove the shaft 150 or other rasping instrument if present and deliver the bone graft material, for example, using the trigger 110.

Although use of the device 100 has been described with respect to an example spinal procedure, the device 100 can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible. For example, a bone graft delivery device can include a handle and tube and may or may not include a distal rasping tip. The tube can be integrally formed with the handle and/or a distal rasping tip and/or any or all of the components can have a modular configuration such that various tubes and/or distal tips can be selected and exchanged as desired by the surgeon or other user. A bone graft delivery device can have a curved or straight tube. A distal tip can have any suitable configuration, including bullet-shaped, flat, conical, or any other configuration. A bone graft delivery device can be configured to received and/or supplied with various endoscopes, other cameras or imaging equipment, and/or guide brackets for imaging equipment. A bone graft delivery device can include any suitable ratcheting mechanism to advance bone graft material through the device for delivery and may include a plunger and/or pusher rod. Certain embodiments of the invention are encompassed in the claim set listed below.

What is claimed is:

1. A bone graft delivery system kit comprising:
a bone graft loading assembly comprising:
a first tubular body configured to be loaded with a bone graft material;
a second tubular body configured to receive bone graft material from the first tubular body; and
a first plunger comprising:
a plunger shaft configured to be advanced within the first tubular body along a first axis; and
a plunger body coupled to an end of the plunger shaft and configured to seal with an inner wall of the first tubular body so as to urge bone graft material to flow from the first tubular body into the second tubular body when the plunger shaft is advanced within the first tubular body, the second tubular body being configured to facilitate flow of bone graft material within the second tubular body along a second axis orthogonal to the first axis;
wherein the first tubular body comprises:
a proximal end configured to receive the plunger body and plunger shaft;
a distal end; and
an opening positioned between the proximal end and the distal end configured to establish fluid communication between the first tubular body and the second tubular body;
an elongate tube configured to be coupled to the second tubular body of the bone graft loading assembly to be filled with bone graft material;
a handle configured to be coupled to the elongate tube; and
a second plunger configured to be advanced within the elongate tube.

2. The kit of claim 1, wherein the second tubular body is integrally formed with the first tubular body.

3. The kit of claim 1, wherein the bone graft loading assembly comprises a tube stop filling an internal volume of the first tubular body between the distal end of the first tubular body and the opening.

4. The kit of claim 3, wherein the tube stop extends proximally to a distal end of the opening.

5. The kit of claim 1, further comprising a tip configured to be coupled to an end of the elongate tube, the tip comprising one or more openings configured to deliver bone graft material and a surface configured to decorticate bone.

6. The kit of claim 1, further comprising a pusher rod configured to be removably received in the elongate tube.

7. The kit of claim of claim 1, wherein the second plunger comprises a rubber tip.

8. A bone graft delivery system kit comprising:
a bone graft loading assembly comprising:
a first tubular body configured to be loaded with a bone graft material;
a second tubular body coupled to the first tubular body; and
a first plunger comprising:
a plunger shaft configured to be advanced in the first tubular body along an axis; and
a plunger body coupled to an end of the plunger shaft and configured to seal with an inner wall of the first tubular body so as to urge bone graft material to flow out of the first tubular body when the plunger shaft is advanced within the first tubular body;
wherein the first tubular body comprises:
a proximal end configured to receive the plunger body and plunger shaft;
a distal end; and an opening positioned between the proximal end and the distal end configured to establish fluid communication between the first tubular body and the second tubular body;

an elongate tube configured to be coupled to the bone graft loading assembly to be filled with bone graft material, the elongate tube having a longitudinal axis orthogonal to the axis along which the plunger shaft advances in the first tubular body when the elongate tube is coupled to the bone graft loading assembly, wherein the elongate tube is configured to couple to the second tubular body;

a handle configured to be coupled to the elongate tube; and a second plunger configured to be advanced within the elongate tube.

9. The kit of claim of claim 8, wherein the second plunger comprises a rubber tip.

10. The kit of claim 1, further comprising the bone graft material.

11. The kit of claim 8, further comprising a pusher rod configured to be removably received in the elongate tube.

12. The kit of claim 8, wherein the second tubular body is positioned to facilitate the flow of bone graft through the second tubular body parallel to the longitudinal axis of the elongate tube when the elongate tube is coupled to the second tubular body.

13. The kit of claim 8, wherein the second tubular body is integrally formed with the first tubular body.

14. The kit of claim 8, wherein the bone graft loading assembly comprises a tube stop filling an internal volume of the first tubular body between the distal end of the first tubular body and the opening.

15. The kit of claim 14, wherein the tube stop extends proximally to a distal end of the opening.

16. The kit of claim 8, further comprising the bone graft material.

17. A bone graft delivery system kit comprising:
a bone graft loading assembly comprising:
a tubular body configured to be loaded with a bone graft material; and
a first plunger comprising:
a plunger shaft configured to be advanced in the tubular body along an axis; and
a plunger body coupled to an end of the plunger shaft and configured to seal with an inner wall of the tubular body so as to urge bone graft material to flow out of the tubular body when the plunger shaft is advanced within the tubular body;

an elongate tube configured to be coupled to the bone graft loading assembly to be filled with bone graft material, the elongate tube having a longitudinal axis orthogonal to the axis along which the plunger shaft advances in the tubular body when the elongate tube is coupled to the bone graft loading assembly;

a handle configured to be coupled to the elongate tube;

a second plunger configured to be advanced within the elongate tube; and a tip configured to be coupled to an end of the elongate tube, wherein the tip comprises one or more openings configured to deliver bone graft material and a surface configured to decorticate bone.

18. The kit of claim 17, wherein the tubular body comprises a first tubular body, the bone graft loading assembly further comprising a second tubular body coupled to the first tubular body, wherein the elongate tube is configured to couple to the second tubular body.

19. The kit of claim 18, wherein the second tubular body is positioned to facilitate the flow of bone graft through the second tubular body parallel to the longitudinal axis of the elongate tube when the elongate tube is coupled to the second tubular body.

20. The kit of claim 18, wherein the second tubular body is integrally formed with the first tubular body.

21. The kit of claim 18, wherein first tubular body comprises:
a proximal end configured to receive the plunger body and plunger shaft;
a distal end; and
an opening positioned between the proximal end and the distal end configured to establish fluid communication between first tubular body and the second tubular body.

22. The kit of claim 17, further comprising a pusher rod configured to be removably received in the elongate tube.

23. The kit of claim 17, wherein the second plunger comprises a rubber tip.

24. The kit of claim 17, further comprising the bone graft material.

* * * * *